US008846617B2

(12) United States Patent
Luger

(10) Patent No.: US 8,846,617 B2
(45) Date of Patent: Sep. 30, 2014

(54) INFLAMMATION INHIBITING COMPOUNDS

(76) Inventor: Thomas Luger, Muenster (DE)

( * ) Notice: Subject to any disclaimer, the term of this patent is extended or adjusted under 35 U.S.C. 154(b) by 122 days.

(21) Appl. No.: 13/184,518

(22) Filed: Jul. 16, 2011

(65) Prior Publication Data

US 2012/0045462 A1   Feb. 23, 2012

Related U.S. Application Data

(63) Continuation-in-part of application No. 10/467,993, filed as application No. PCT/EP02/01323 on Feb. 8, 2002, now Pat. No. 8,003,608.

(30) Foreign Application Priority Data

Feb. 14, 2001 (DE) .................................... 10106852

(51) Int. Cl.
| | | |
|---|---|---|
| *A61K 38/34* | (2006.01) | |
| *C07K 14/68* | (2006.01) | |
| *A61K 38/05* | (2006.01) | |
| *A23L 1/305* | (2006.01) | |
| *A61K 38/06* | (2006.01) | |
| *A61K 38/04* | (2006.01) | |
| *A61K 39/00* | (2006.01) | |

(52) U.S. Cl.
CPC ............... *A23L 1/3051* (2013.01); *A61K 38/05* (2013.01); *A23L 1/3053* (2013.01); *C12N 2501/86* (2013.01); *A61K 38/06* (2013.01); *A61K 38/04* (2013.01); *A61K 2039/5154* (2013.01)
USPC ....................................................... 514/10.7

(58) Field of Classification Search
CPC ............... A23L 1/3051; A23L 1/3053; A61K 2039/5154; A61K 38/04; A61K 38/05; A61K 38/06; C12N 2501/86
See application file for complete search history.

(56) References Cited

U.S. PATENT DOCUMENTS

| | | | | |
|---|---|---|---|---|
| 4,966,848 | A | * 10/1990 | Smith et al. .................... | 435/193 |
| 5,223,421 | A | * 6/1993 | Smith et al. .................... | 435/193 |
| 5,614,520 | A | 3/1997 | Kondo et al. | |
| 5,837,218 | A | * 11/1998 | Peers et al. .................... | 424/1.69 |
| 5,939,394 | A | 8/1999 | Fleming et al. | |
| 6,117,896 | A | 9/2000 | Qabar et al. | |
| 7,960,508 | B2 | 6/2011 | Hattori et al. | |

FOREIGN PATENT DOCUMENTS

| | | |
|---|---|---|
| EP | 0934924 | 8/1999 |
| FR | 2784028 | 4/2000 |
| WO | WO/88/00833 | 9/1988 |
| WO | WO 89/09226 | 8/1989 |
| WO | WO/96/23490 | 8/1996 |
| WO | WO/96/27371 | 9/1996 |
| WO | WO 97/45117 | 12/1997 |

OTHER PUBLICATIONS

What is psoriasis? http://www.skincarephysicians.com/psoriasisnet/whatis.html.
Mesri, EA, *Blood*, Jun. 15, 1999; 93(12): 4031-3.
Portanova JP, et al, "Selective neutralization of prostaglandin E2 blocks inflammation, hyperalgesia, and interleukin 6 production in vivo," J Exp Med. Sep. 1, 1996;184(3):883-91.
Kalden DH, et al "Mechanisms of the antiinflammatory effects of alpha-MSH. Role of transcription factor NF-kappa B and adhesion molecule expression," Ann N Y Acad Sci. Oct. 20, 1999;885:254-61.
Uehara Y, et al "The dipeptide Lys-Pro attenuates interleukin-1 beta-induced anorexia," Peptides. Mar.-Apr. 1993;14(2):175-8.
Rajora N, et al, "Alpha-MSH modulates experimental inflammatory bowel disease," Peptides. 1997;18(3):381-385.
Oluyomi, A.O., et al., "Antinociceptive activity of peptides related to interleukin-1β-(193-195), Lys-Pro-Thr" European Journal of Pharmacology 1994; 258: 131-138.
Database CA Online, Chemical Abstracts Service, Columbus, Ohio, US; Suetsugu, Maseru et al, "Skin conditioners containing lysine derivatives," retrieved from STN, Database accession No. 132:339047 HCA, XP002205557.
Database WPI Week 200033, Derwent Publications Ltd., London, GB; AN 2000-382026, XP002208222 & JP 2000 128726 A (Shiseido Co. Ltd.), May 9, 2000, Zusammenfassung.
Database WPI, Section Ch, Week 200057, Derwent Publications Ltd., London, GB; Class B07, AN 2000-602052, XP002208223—& WO 00 54750 A (Starchenko D A); Sep. 21, 2000, Zusammenfassung.
Database Biosis Online, Biosciences Information Service, Philadelphia, PA, US; 1992 Palmieri G., et al., "Clinical and Immunological Effects of a Lysine Arginine Association in Atopic Dermatitis," Database accession No. PREV199293081020, XP002205558, Zusammenfassung.
Himmi, E. H., et al., "Regulatory role of a peptide from the second constant domain of immunoglobulin G—II. In vitro effect on granuloma formation around S. mansoni eggs," Int. J. Immunopharmac. 1985; 7(2): 231-237.
Patent Abstracts of Japan, vol. 1998, No. 01; Jan. 30, 1998 & JP 09 249535 A (Honen Corp.), Sep. 22, 1997, Zusammenfassung.
Database CA Online, Chemical Abstracts Service, Columbus, Ohio, US; Terai, M., "Antibacterial, low-irritation cosmetics," retrieved from STN, Database accession No. 127:336470 HCA, XP002236549, Zusammenfassung.
Database WPI, Week 199802, Derwent Publications Ltd., London, GB; AN 1998-011903, XP002236550 & JP 09 255518 A (Noevir KK), Sep. 30, 1997, Zusammenfassung.
Patent Abstracts of Japan, vol. 1998, No. 01, Jan. 30, 1998, & JP 09 255518 A (Noevir Co Ltd), Sep. 30, 1997, Zusammenfassung.
Hiltz, M. E., et al., "Anti-Inflammatory Activity of α-MSH (11-13) Analogs: Influence of Alteration in Stereochemistry," Peptides 1991; 12: 767-771.

(Continued)

*Primary Examiner* — Thomas Heard
(74) *Attorney, Agent, or Firm* — Chalin A. Smith; Smith Patent

(57) ABSTRACT

The present invention relates to the use of compounds selected from the group consisting of Lys-(D)Pro-Thr, N-acyl Lys-(D)Pro-Thr, C-amide Lys-(D)Pro-Thr, and C-esters of Lys-(D)Pro-Thr; or a pharmaceutically acceptable salt of said compound fort he treatment of inflammatory disorders. The invention also relates to the use of αMSH for inducing tolerance.

8 Claims, 54 Drawing Sheets

(56) References Cited

OTHER PUBLICATIONS

Macaluso, A., et al., "Antiinflammatory Influences of α-MSH Molecules: Central Neurogenic and Peripheral Actions," J Neurosci 1994;14(4): 2377-2382.

Richards, D. B., et al., "Effect of α-MSH 11-13 (Lysine-Proline-Valine) on Fever in the Rabbit," Peptides 1984; 5: 815-817.

Beers, M.H., et al., "The Merck Manual of Diagnosis and Therapy," 1999, Merck Research Laboratories, Whitehouse Station, NJ, XP002208945.

Thews, G., et al., "Anatomie, Physiologie and Pathophysiologie des Menschen," 1991, WVG, Stuttgart XP002236548.

Vuitton, D., "The ambiguous role of immunity in echinococcosis: protection of the host or of the parasite?" Acta Tropica 2003; 85: 119-132.

International Search Report for PCT Application No. PCT/EP02/01323 prepared by the European Patent Office, issued on Apr. 29, 2003.

Klement et al. IκBα Deficiency Results in a Sustained NF-κB Response and Severe Widespread Dermatitis in Mice, Molecular and Cellular Biology, May 1996, p. 2341-2349.

Kwon et al. Insulin-like Growth Factor II Induces Interluekin-6 Expression via NF-κB Activation in Psoriasis, Biochemical and Biophysical Research Communications 278, 312-317 (2000).

Chen et al. RAG2-/-, IκBα Chimeras Display a Psoriasisform Skin Disease, J. Invest Dermatol 115:1124-1133, 2000.

Schmidt K.N. Anti-Psoriatic Drug Anthralin Activates Transcripton Factor NFκB in Murine Keratinocytes, The Journal of Immunology, 1996, 156:4514-4519.

Robert et al. Inflammatory Skin Diseases, T-Cells, and Immune Surveilance, The New England Journal of Medicine 341(24), 1817-1828, 1999.

Wirtz S, Neufert C, Weigmann B and Neurath F; Chemically Induced Mouse Models of Intestinal Inflammation. Nature Protocols vol. 2 No. 3. 2007 541-546.

Elson C.O, Sartor R.B., Tennyson G.S. and Riddel R H.; Experimental Models of Inflammatory Bowel Disease. Gastroenterology 1995:109:1344-1367.

\* cited by examiner

Fig. 16
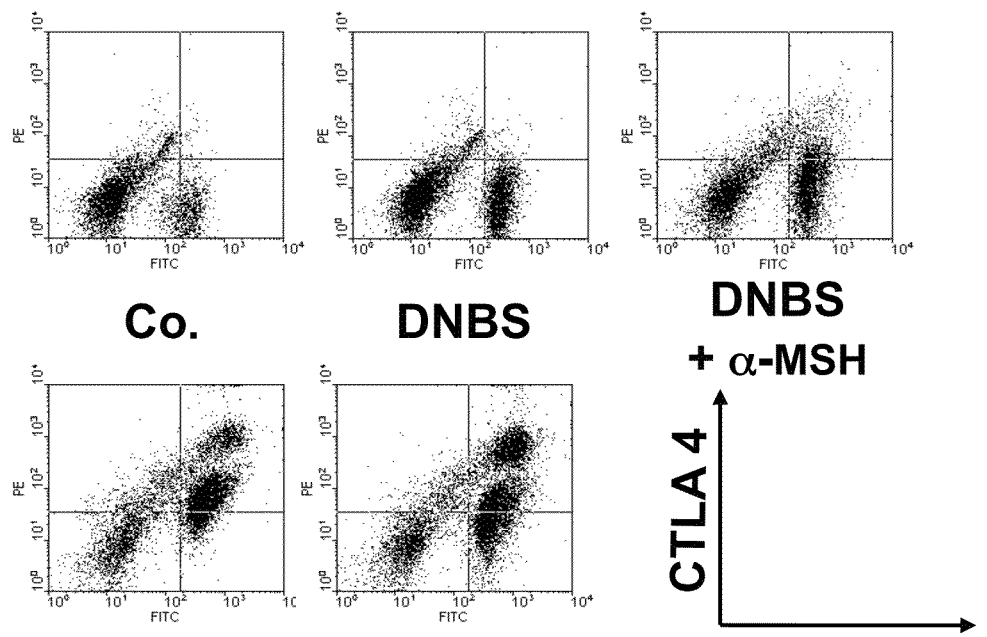
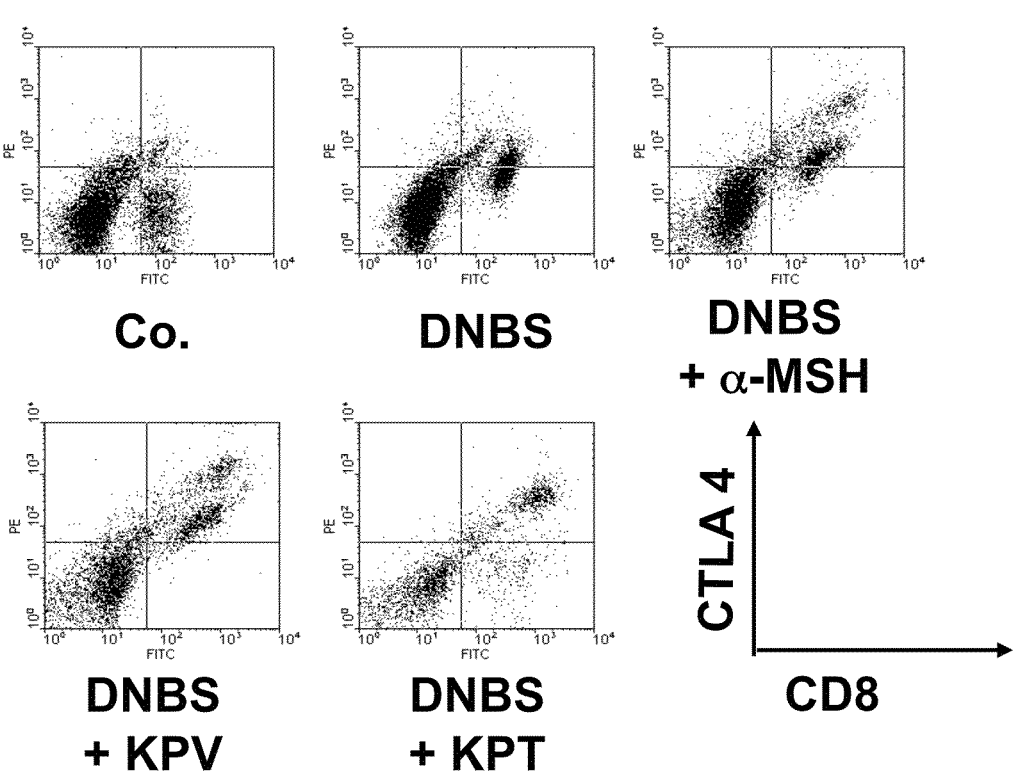

10 µg KdPT    PBS (control)

Fig. 22
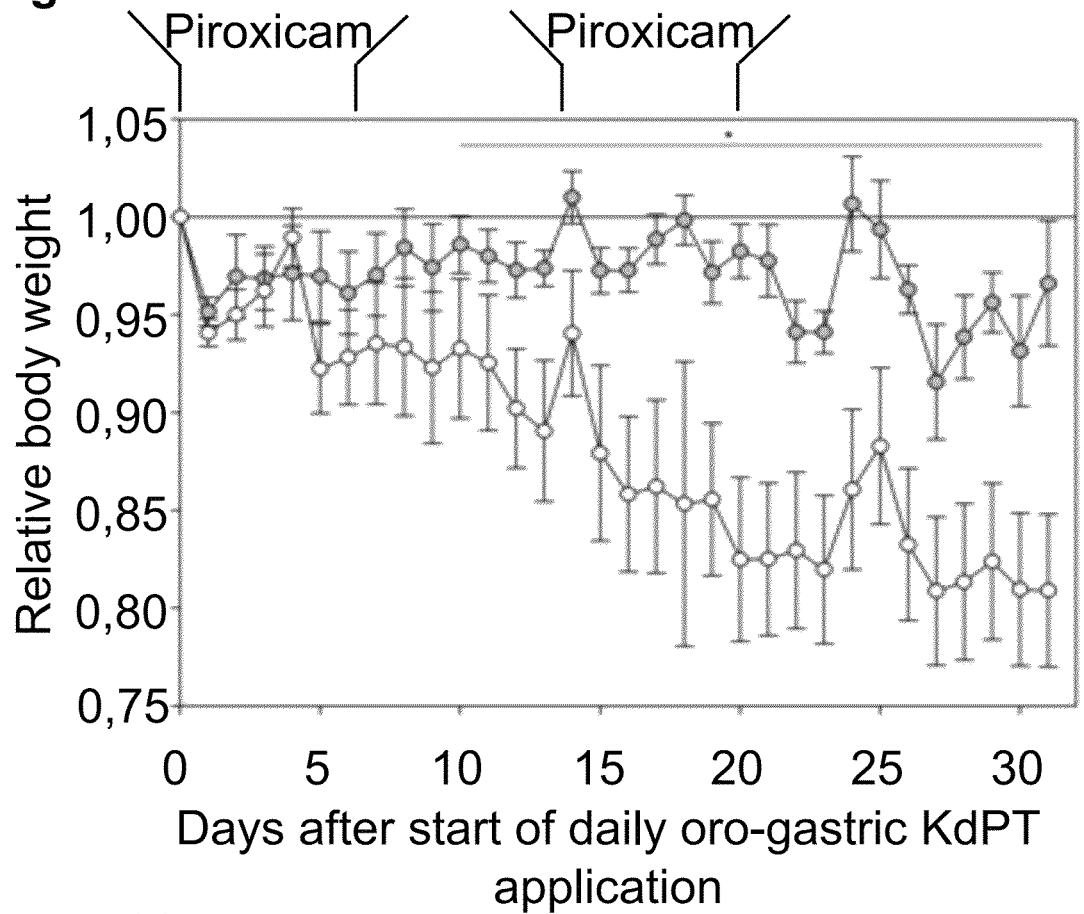
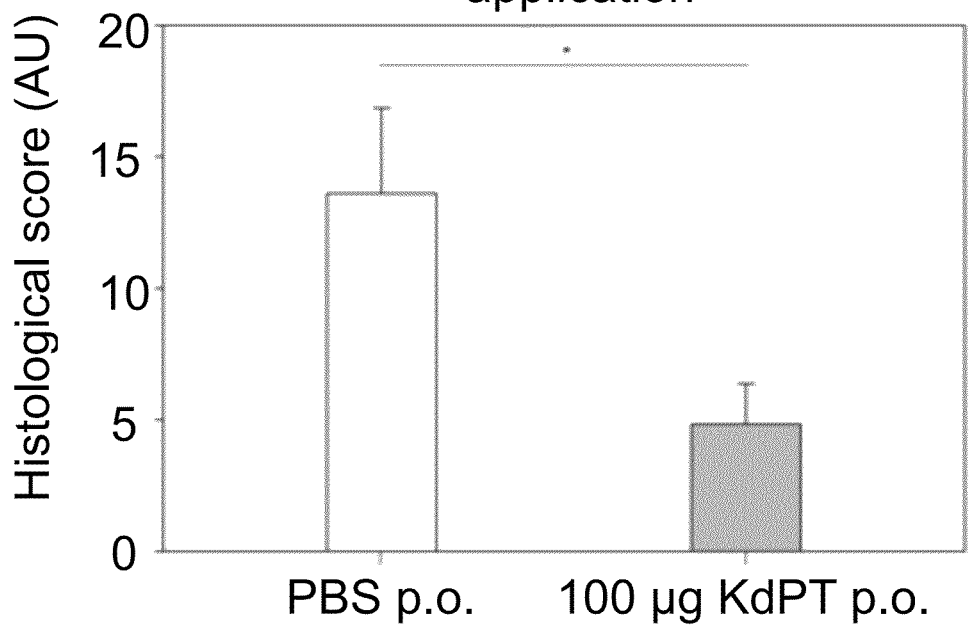

Fig. 24 continued
Group 1, no. 1.1
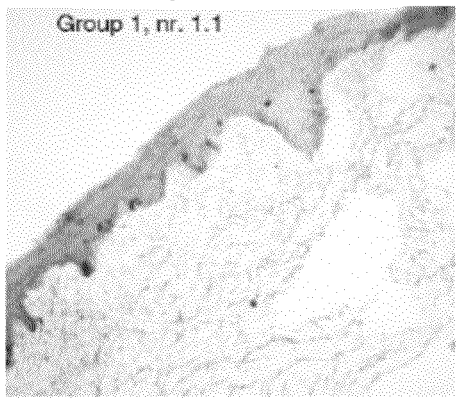
Group 2, no. 1.3
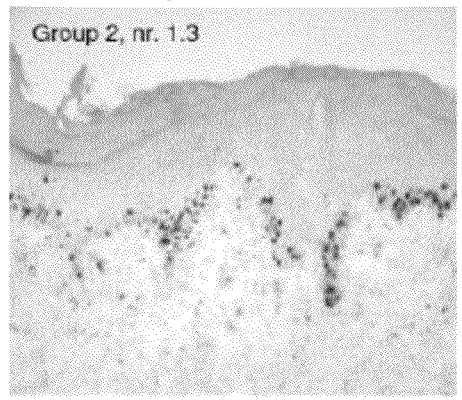
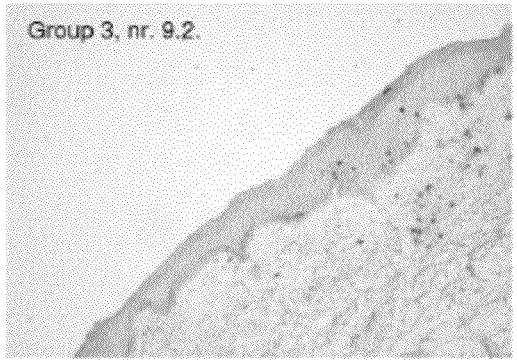
Group 3, no. 2.3
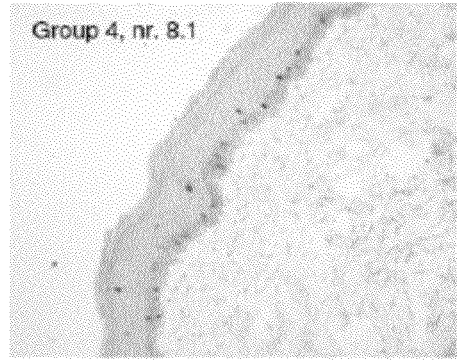
Group 4, no. 8.1

A

Fig 27 A
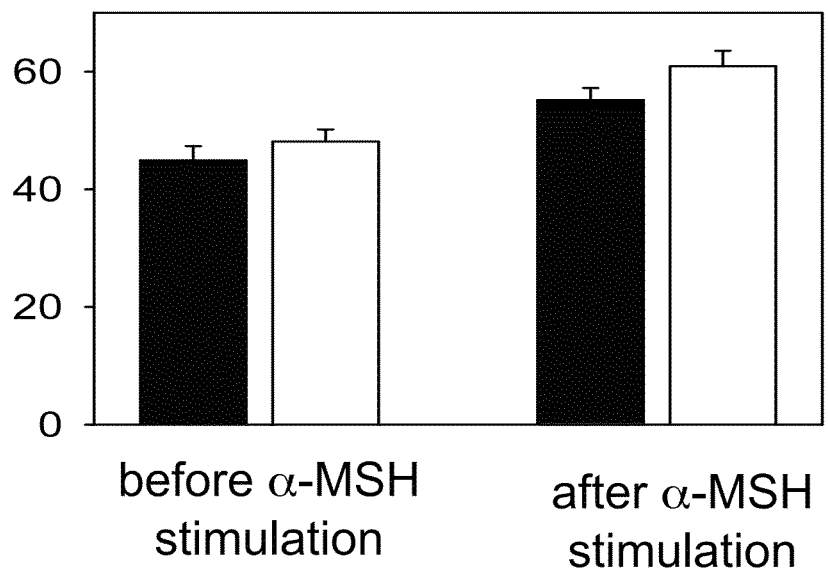
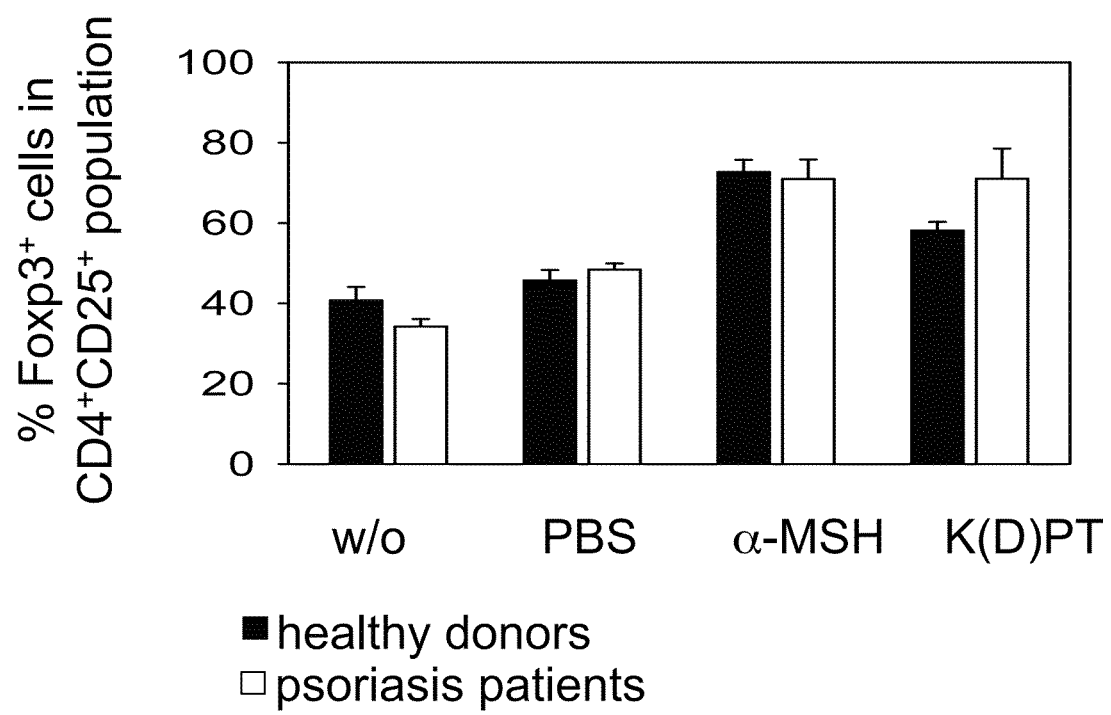

Foxp3 isotype control
— healthy donor + PBS
— healthy donor + α-MSH
— psoriasis patient + PBS
— psoriasis patient + α-MSH
(cells gated for CD4⁺CD25⁺)

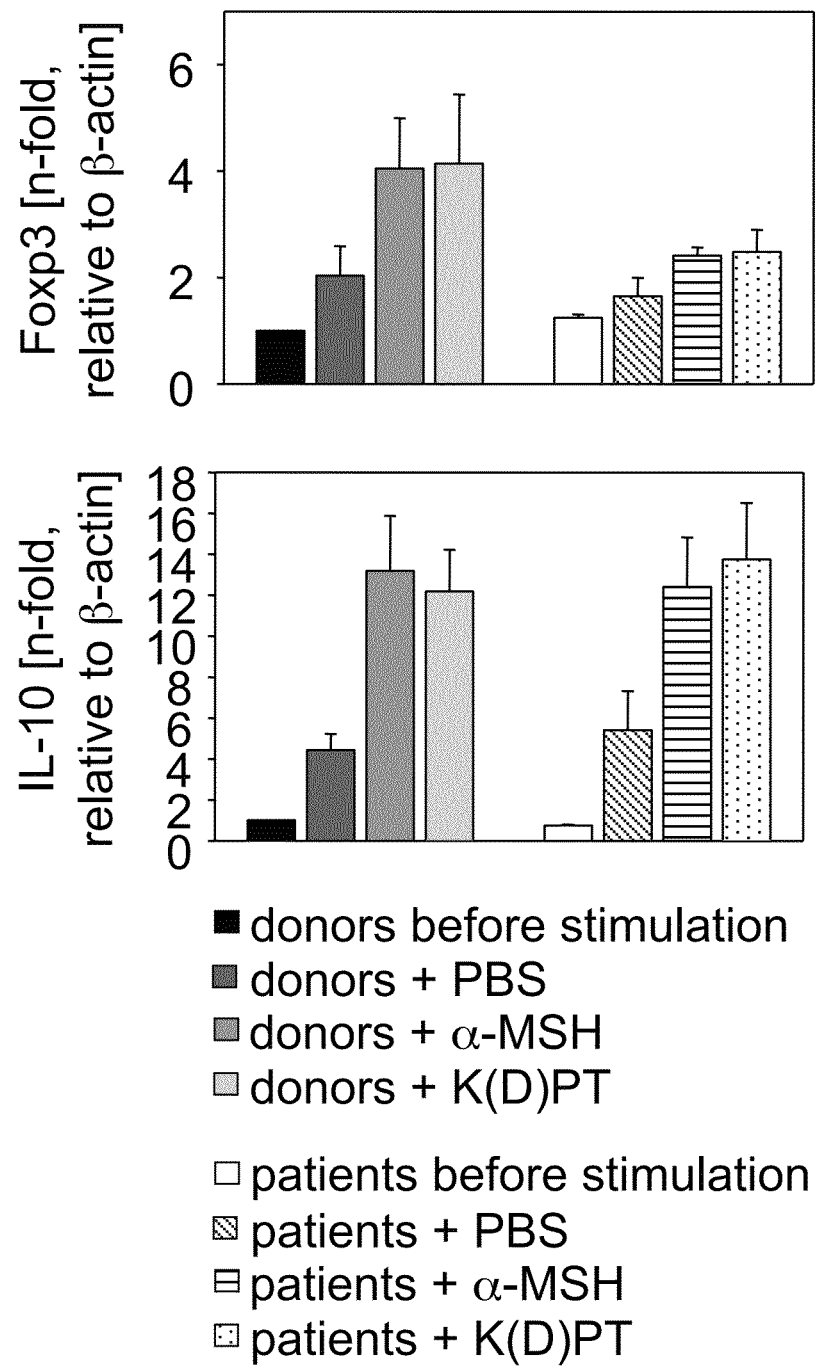

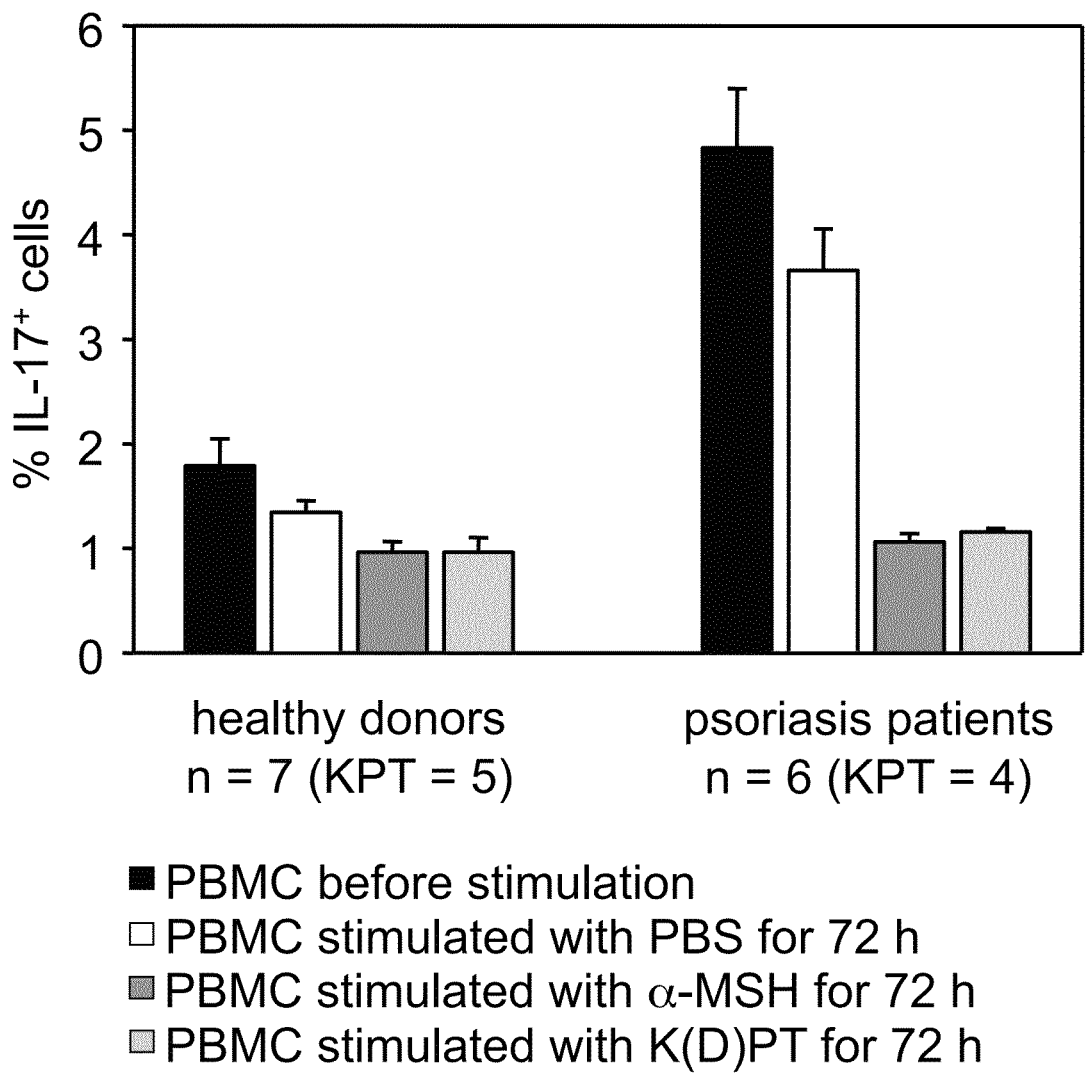

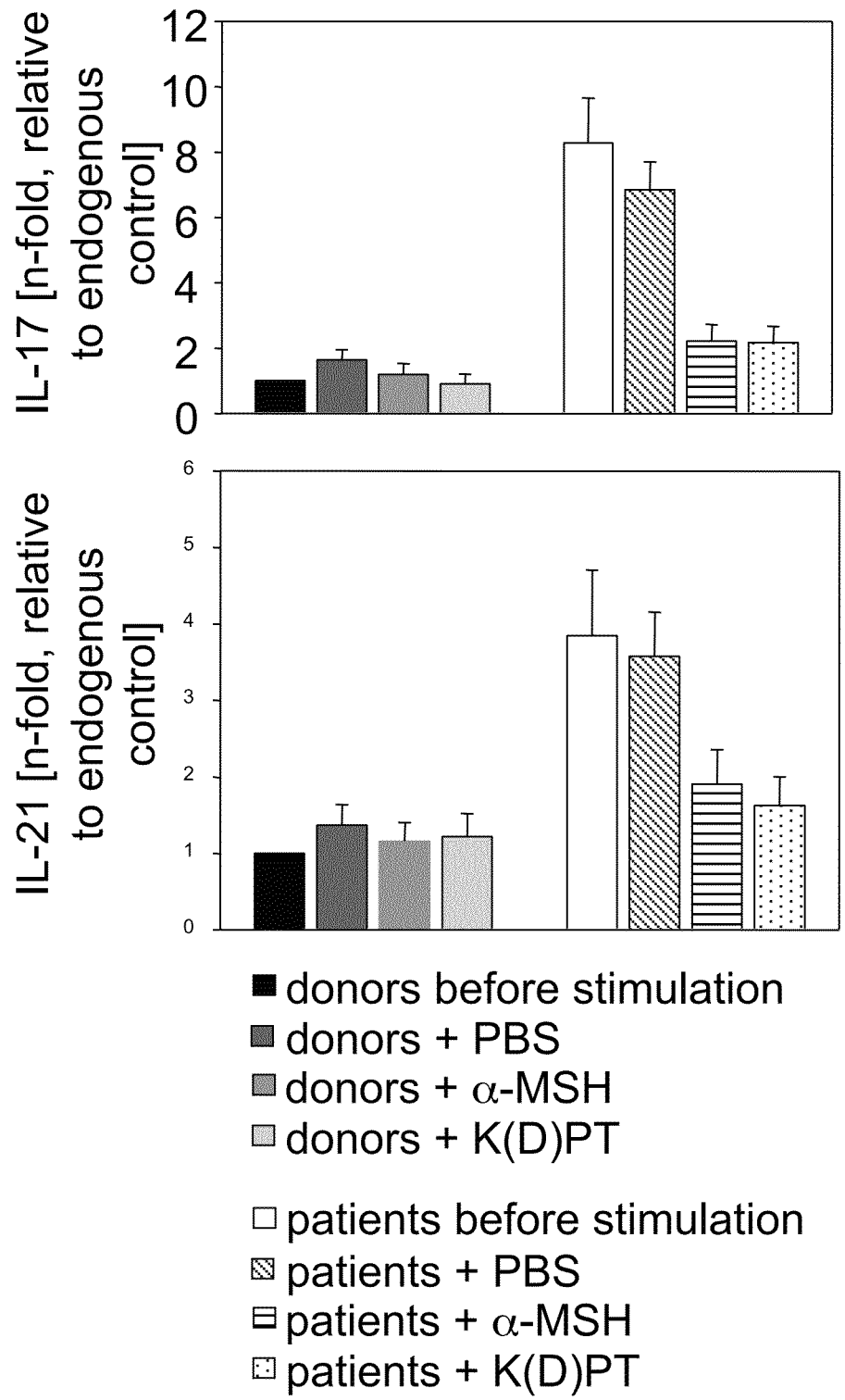

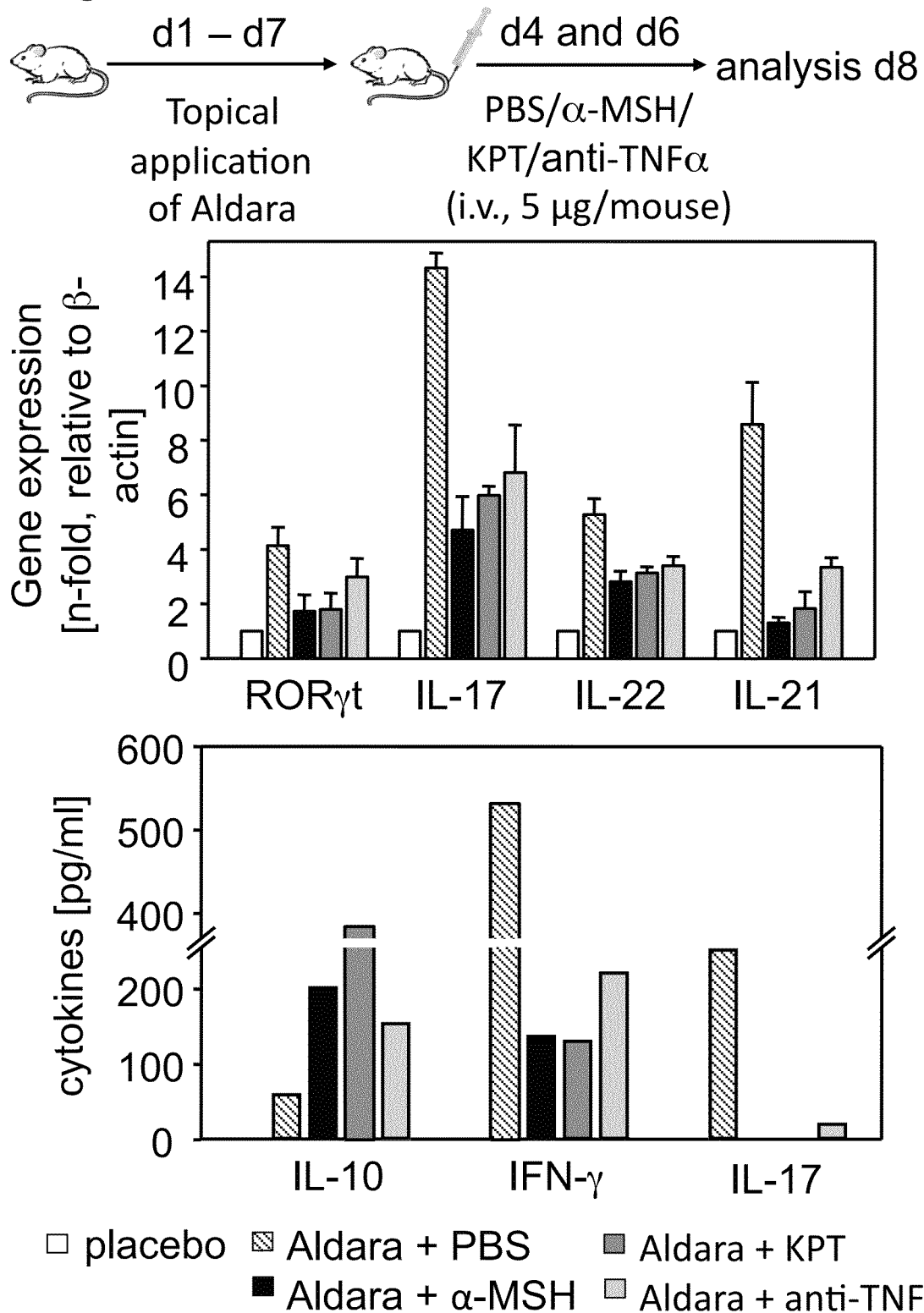

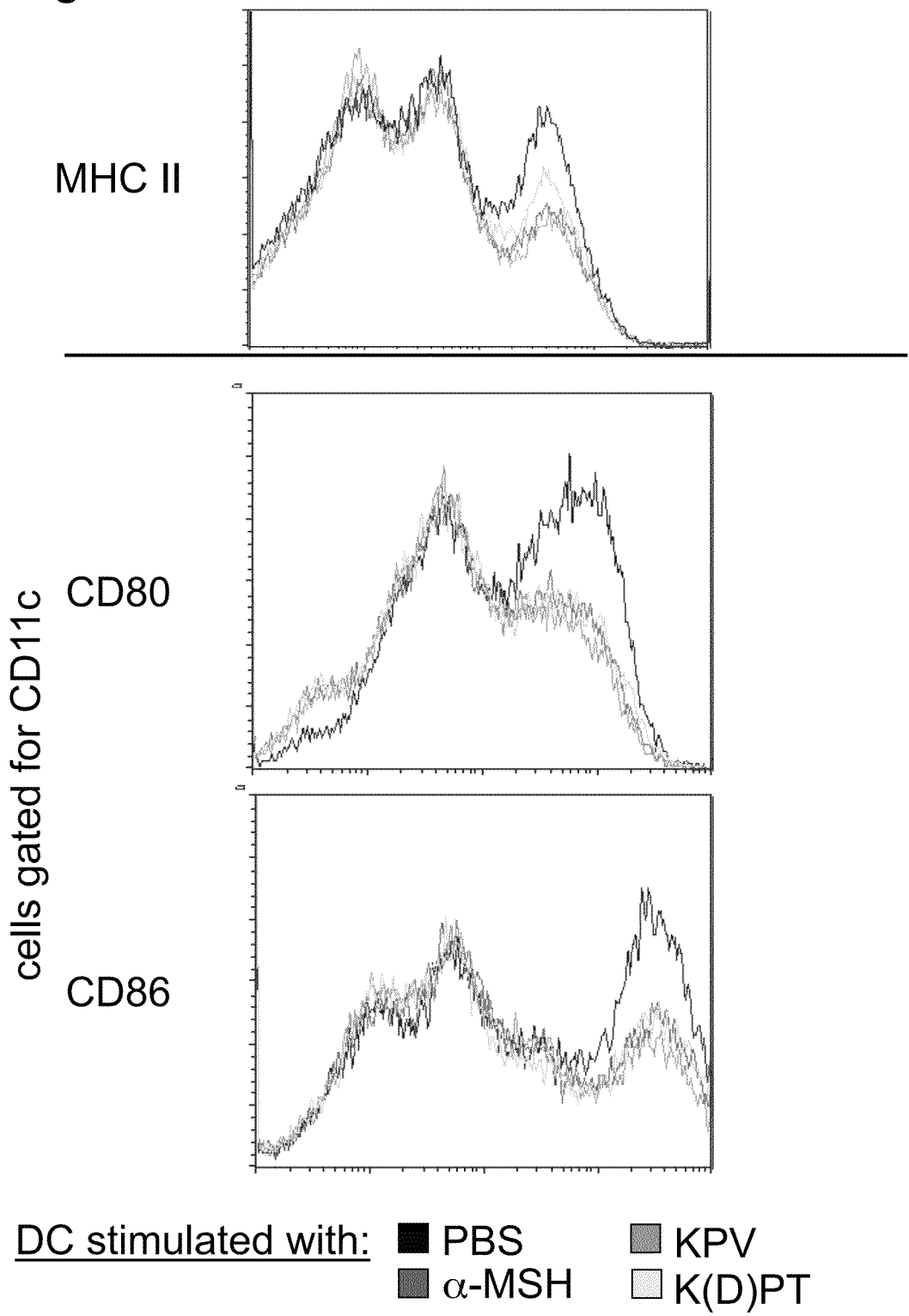

DC stimulated with: ■ PBS  ■ KPV
■ α-MSH  □ K(D)PT

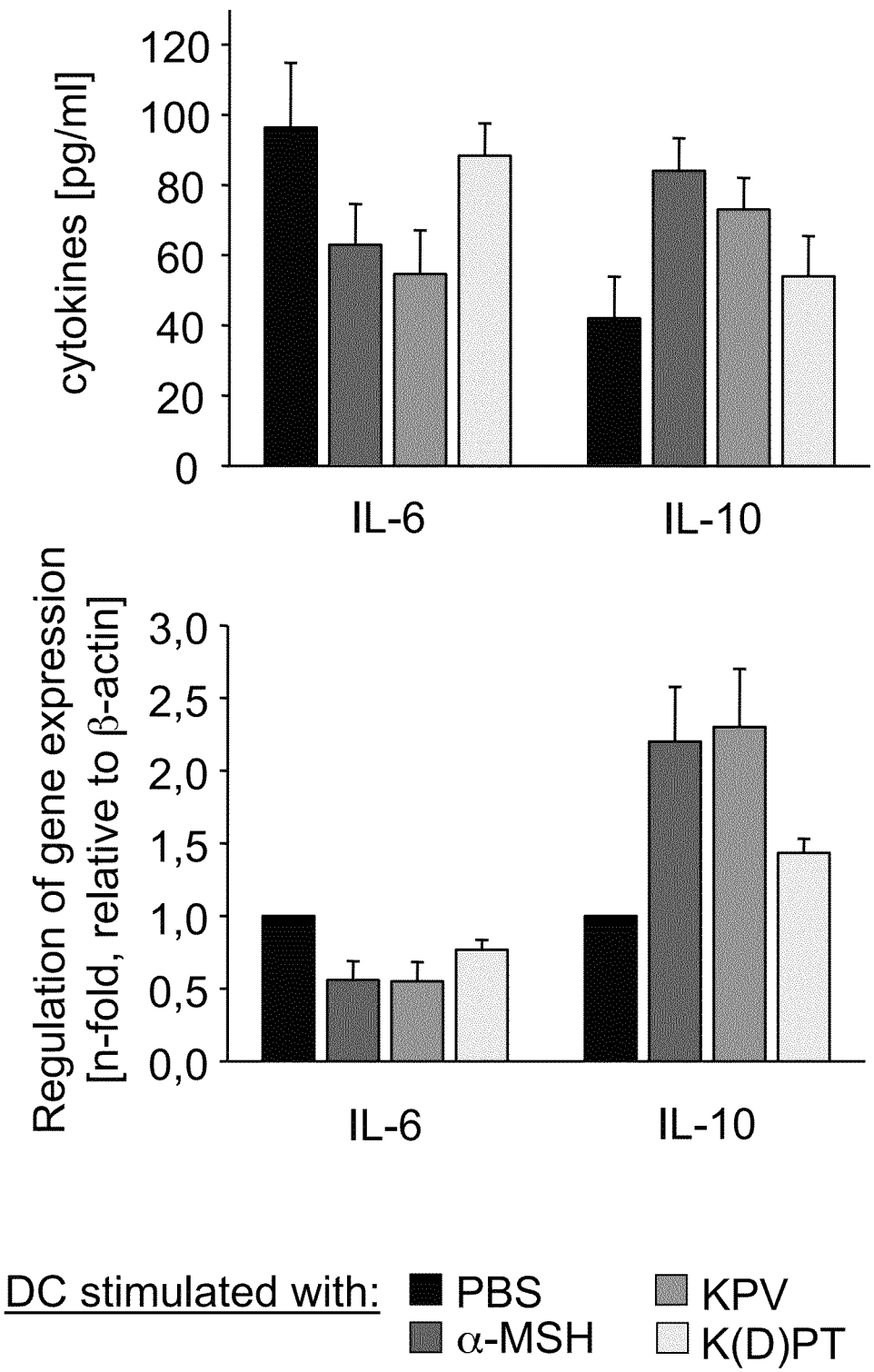

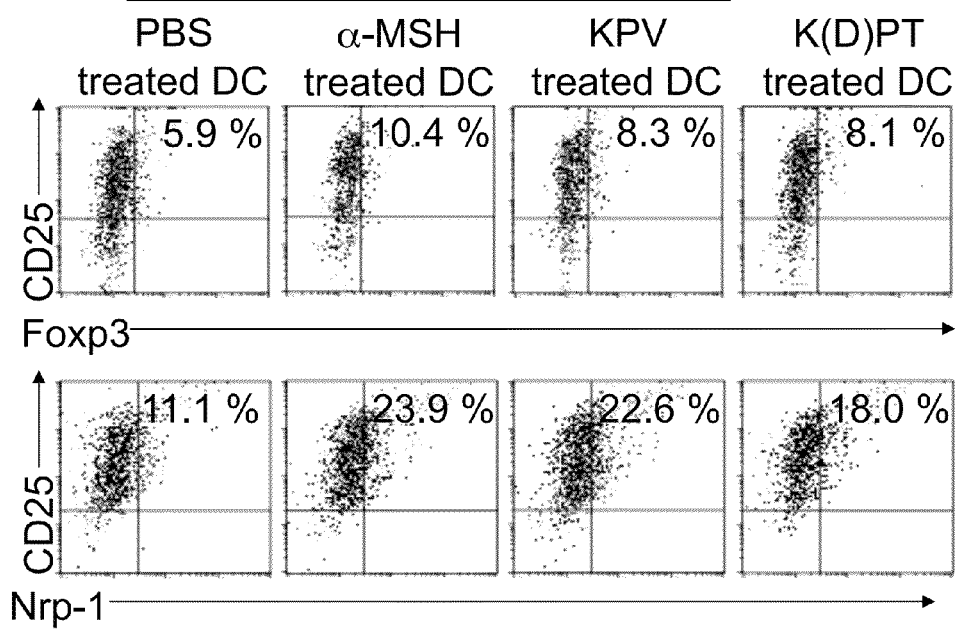

CD4+ T cells from co-cultures with
- PBS treated DC
- α-MSH treated DC
- KPV treated DC
- K(D)PT treated DC ■ Neg. co. (no sensitization)
■ Pos. Co. (no active compound)
■ 5 µg dexamethasone i.v. 2h prior to challenge
□ 1 µg KdPT i.v. 2h prior to challenge ■ Neg. co. (no sensitization)
■ Pos. Co. (no active compound)
▨ 5 µg dexamethasone i.v. 2h prior to challenge
☐ 1 µg KdPT i.v. 2h prior to challenge Green = c-KIT-staining

INFLAMMATION INHIBITING COMPOUNDS

This application is a Continuation-in-Part of U.S. Ser. No. 10/467,993 filed Sep. 26, 2003, which is based on International Application Number PCT/EPO2/01323 filed Feb. 8, 2002.

FIELD OF THE INVENTION

The tridecapeptide α-melanocyte-stimulating hormone (αMSH) is produced from the precursor hormone pro-opiomelanocortin (POMC). Several biologically active peptide hormones such as, for example, β-lipotropin, adrenocorticotropin (ACTH), β-endorphin and the melanotropins (α-, β- and γMSH) are derived from the POMC gene product. Proteolytic enzymes with various specificities are necessary for processing these peptides. In addition, post-translational modifications such as acetylations may take place.

BACKGROUND OF THE INVENTION

The effects of αMSH and other POMC peptides on the various tissues are mediated by a family of specific receptors. These melanocortin (MC) receptors belong to the group of G protein-coupled receptors. Five different melanocortin receptors (MC-1 to MC-5) have been cloned. It is assumed that αMSH is an important signal for regulating various melanocyte functions. It is thought, for example, that proliferation, differentiation and cytokine production by melanocytes are influenced by αMSH.

It has also been shown that POMC gene products are able to influence immune responses and inflammatory reactions. For example, it is assumed that αMSH down-regulates several proinflammatory cytokines, while the production of the antiinflammatory cytokine IL-10 is stimulated by αMSH. This means that αMSH has an important function in the suppression of immune responses and inflammatory reactions. Several studies indicate that the immunomodulatory and antiinflammatory effects of αMSH are mediated by the C-terminal region of αMSH (amino acids 11-13: Lys-Pro-Val) because administration of the C-terminal tripeptide is sufficient to induce these effects (Catania and Lipton, 1993, Endocr. Rev. 14, 564-576; Bhardvaj et al., 1996, J. Immunol. 156, 2517-2521). WO 88/00833 discloses the use of the tripeptide Lys-Pro-Val for producing a medicament for the treatment of inflammations. The C-terminal tripeptide of αMSH has likewise been proposed as agent to prevent loss of hair (FR 2 733 421).

SUMMARY OF THE INVENTION

One object of the present invention is to provide further inflammation-inhibiting compounds.

It has surprisingly been found that the tripeptide Lys-Pro-Thr has antiinflammatory properties. Unexpectedly, even smaller compounds such as Lys-Pro and Lys also show advantageous properties.

The present invention therefore relates to the use of a compound of the formula (I)

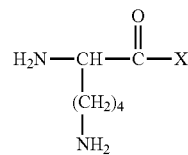

where X is a hydroxyl group, an amino group, alkoxy, Pro or Pro-Thr, or of a pharmaceutically acceptable salt thereof, for the treatment and/or prevention of inflammatory disorders. The term "inflammatory disorders" encompasses not only inflammations but also disorders in which an inflammation is involved, such as, for example, autoimmune diseases or transplant rejections.

The compound used according to the invention may be lysine or the dipeptide lysine-proline, but the tripeptide lysine-proline-threonine (=KPT) is preferably used.

Naturally occurring amino acids usually have the (L) configuration. The amino acids of the compounds used according to the invention may have either the (L) or the (D) configuration. Possible compounds of the MDT structure are thus
(L)Lys-(D)Pro-(L)Thr,
(L)Lys-(L)Pro-(D)Thr,
(L)Lys-(D)Pro-(D)Thr,
(L)Lys-(L)Pro-(L)Thr,
(D)Lys-(D)Pro-(L)Thr,
(D)Lys-(D)Pro-(D)Thr,
(D)Lys-(L)Pro-(L)Thr,
(D)Lys-(L)Pro-(D)Thr,
with the compound (L)Lys-(D)Pro-(L)Thr being most preferred. The compounds used according to the invention may also show amino acid exchanges, with one of the amino acids having been conservatively changed.

The compound of the formula (I) used according to the invention may be chemically modified at the N terminus and/or at the C terminus, for example by an acyl group, preferably an acetyl group at the N terminus and/or an amidation or esterification of the C terminus. Further protective groups known per se are likewise possible. The modifications may also affect the amino group in the side chain of lysine or the hydroxyl group of threonine. Other modifications are also conceivable on the side of the $NH_2$ group, e.g. extension by a glycine, and further amino acid residues up to the length of αMSH.

For the purposes of the present application, the term "compound of the formula (I)" also includes the pharmaceutically acceptable salts of the compound.

Said compounds can be used for the treatment of all types of acute or chronic inflammations. These include inter alia acute and chronic inflammations for example of the skin, psoriasis, atopic dermatitis, allergic reactions of all types, from rhinitis via contact allergies to asthma and food allergies, autoimmune diseases, fibroses and sclerodermas and transplant rejection but also vascular disorders. Autoimmune diseases particularly include but are not limited to multiple sclerosis, vasculitis, rheumatoid arthritis, psoriasis, Crohn's disease and ulcerative colitis. The compounds are preferably used for the treatment of inflammatory conditions of the skin. It is advantageous in this case to administer the compound as topical formulation in the form of an ointment or cream. The compound is normally present in an ointment or cream in a concentration of from 1 μM to 1 mM, preferably from 10 μM to 100 μM. Such an ointment or cream may additionally comprise conventional ingredients as described, for example, in Braun-Falco et al. (1996) Dermatologie und Venerologie, Springer Verlag, Berlin or Merk, Bickers (1992) Dermatopharmakologie und Dermatotherapie.

It is possible in a preferred embodiment for the peptides also to be used according to the invention for inflammatory bowel disorders. Examples of inflammatory disorders are, besides short-term irritations of the bowel caused by relatively mild food poisonings, also chronic bowel disorders such as Crohn's disease or ulcerative colitis.

In another preferred embodiment, the compounds can be used according to the invention for the treatment of inflammatory disorders of inflammations occurring at sites in the body which come into contact with the environment. These include in particular the mucous membrane of the mouth and gastrointestinal tract, and of the lung.

The compounds used according to the invention do, however, also have systemic activity for the treatment or prevention of inflammations. The compound is then preferably administered intraperitoneally, intravenously or orally. The dose of an administration is usually 20 µg to 10 mg/kg of body weight, preferably 100 µg to 1 mg/kg of body weight.

Further, said compounds can also be used in sprays, e.g. in nasal or oral sprays. For example they can be used for inhalation for the treatment of inflammations of the airways. Finally, in certain embodiments the compounds and pharmaceutical compositions described herein are to be administered rectally. These pharmaceutical compositions are adapted for rectal administration.

In the treatment of psoriasis, the pharmaceutical composition is preferably administered topically, orally or intravenously.

It is possible to employ a plurality of different compounds of the formula (I) for the treatment. In this embodiment, at least two different compounds of the formula (I) are used for the treatment of inflammations.

The compounds of the formula (I) can also be used to produce a medicament for the treatment and/or prevention of inflammations. All the embodiments indicated above are encompassed analogously by this use. The compound is normally mixed with a pharmaceutically acceptable carrier or diluent. Processes known per se for producing medicaments are indicated in Forth, Henschler, Rummel (1996) Allgemeine and spezielle Pharmakologie und Toxikologie, Urban & Fischer. Pharmaceutical compositions comprising the compounds described herein can be preferably manufactured as described in "Remington: The Science and Practice of Pharmacy", 20$^{th}$ edition (2000), ISBN-10: 0683306472, ISBN-13: 978-0683306477.

The compounds of the formula (I) may also be added to foods in order to reduce the allergic potential of certain food constituents. The invention therefore also relates to the use of a compound of the formula (I) as addition to foods. The concentration in foods may then be 1 µM to 1 mM.

It is also possible according to the invention to use a compound of the formula (I) as non-pharmaceutical addition in cosmetics. For example, creams comprising a compound of the formula (I) can be employed for irritated skin or after sunbathing.

Surprisingly, the inventors have likewise found that treatment of dendritic cells in vitro with a hapten and αMSH and subsequent injection of the cells into experimental animals leads to the production of haptenspecific tolerance and to suppression of the CHS reaction ("contact hypersensitivity reaction"). The present invention therefore further relates to a method for the in vitro production of cells able to confer tolerance to an antigen, which comprises provision of antigen-presenting cells, bringing the cells into contact with αMSH or a biologically active derivative or fragment thereof, and bringing the cells into contact with the antigen, where the last two steps can be carried out in any sequence or simultaneously.

There are various types of antigen-presenting cells. Dendritic cells or Langerhans cells are preferred according to the present invention. It is unnecessary for the antigen-presenting cells to be present in a preparation which is free of other constituents or cells. The antigen-presenting cells can also be provided mixed with other cells. A preferred example is the provision of epidermal cells in which Langerhans cells are present as antigen-presenting cells. It is also possible to isolate dendritic cells from bone marrow or produce dendritic cells from precursor cells such as, for example, PBMC by in vitro culture known per se. Methods for providing antigen-presenting cells are described for example in Labeur et al. J. of Immunol. 162(1):168-175 (1999).

The cells are then brought into contact in vitro with αMSH or a biologically active derivative or fragment thereof. Biologically active derivatives or fragments of αMSH are, for example, chemical modifications of αMSH, fragments of αMSH including Lys, Lys-Pro, Lys-Pro-Val or Lys-Pro-Thr, or compounds comprising one of said substances. A wide variety of modifications is conceivable as long as the biological activity of αMSH—the ability to induce tolerance—is substantially retained. Normal concentrations of αMSH or said derivatives on being brought into contact with the cells are $10^{-6}$ M to $10^{-16}$ M, preferably $10^{-8}$ M to $10^{-12}$ M.

After the cells have been brought into contact with αMSH or a biologically active derivative or fragment thereof, or previously or simultaneously, the cells are brought into contact in vitro with the antigen against which tolerance is to be induced. The antigen may in this case be a protein against which there is the risk of an allergic reaction. If, for example, it is known against which hapten of the antigen the immune response is directed, the cells can also be brought into contact only with the specific hapten. Possible examples in this connection are peptides with a length of from 7 to 20 amino acids, preferably from 7 to 15 amino acids.

The antigen-presenting cells can be washed after said steps and be mixed with a pharmaceutically acceptable or carrier or diluent. The cells can then be introduced into a patient or into a mammal, whereupon tolerance is produced against the hapten or antigen used.

A further aspect of the invention is the use of αMSH or of a biologically active derivative or fragment thereof for producing a medicament for inducing tolerance to an antigen. The produced medicament preferably comprises cells which are, obtainable by the method described above for the in vitro production of cells able to confer tolerance.

The peptide Lys-Pro-Thr prevents the activation of the transcription factor NF-κB by TNFα, IL-1 or LPS in endothelial cells and in keratinocytes. The consequence is a reduced expression of cell adhesion molecules (endothelial cells) and chemokines (keratinocytes). The inventors have also been able to show that, for example, the KPT peptide prevents the occurrence of contact allergies (contact hypersensitivity reactions, CHS reactions) and induces an allergen-specific, long-lasting tolerance. Two sections are to be distinguished in CHS reactions: initial contact (induction phase) with an antigen lays the foundation for the later CHS reaction, and a further contact with the antigen leads to the occurrence of the reaction (contact dermatitis, i.e. swelling, itching, etc.). The compounds used according to the invention can be employed before both sections, and when employed (injection or topical application) before the initial contact there is suppression of the CHS and induction of tolerance, and when employed at the time of induction of the contact dermatitis the compounds prevent the occurrence of the dermatitis. In all these applications there is substantially complete inhibition of the allergic reaction.

It has likewise been found that Lys-Pro-Thr reduces the expression of costimulatory molecules on dendritic cells. This is most likely part of the mechanism associated with the suppression of the CHS and the induction of tolerance. At the same time, the compounds increase the secretion of the anti-inflammatory IL-10 by monocytes. This effect is likewise part of the mechanism associated with the allergic contact dermatitis.

Without wishing to be bound in any way to one theory, the compounds of the invention might bind to β-adrenergic receptors. It can additionally be assumed that the peptides employed according to the invention are capable of binding to the type I IL-1 receptor. Nor can it be precluded that the peptides of the invention also bind to other receptors such as, for example, the opioid receptor. Based on this assumption, it is presumed that the peptides of the invention are able to bind to a plurality of receptors which, after activation by their original ligands, would all intervene in a proinflammatory way in, the inflammatory event. The binding of the peptide of the invention to these receptors prevents the binding of the original ligands to these receptors, and thus the induction of the proinflammatory effects is prevented. On the other hand, the binding of the peptides of the invention to the receptors of their initial substances (αMSH) activates these receptors and thus induces a further component of the mechanism of action, which is overall antiinflammatory.

BRIEF DESCRIPTION OF THE DRAWINGS

FIG. 16 shows the up-regulation of CTLA-4 on T cells after contact with antigen-loaded and αMSH or derivative-treated DC. A: CD4 positive T cells; B: CD8 positive T cells.

FIG. 22 shows the effect of KdPT on colitis in IL-10 deficient mice.

FIG. 30 shows the effect of KdPT on the expression of murine Th17-typical parameters.

DETAILED DESCRIPTION OF THE INVENTION

Figure 1:
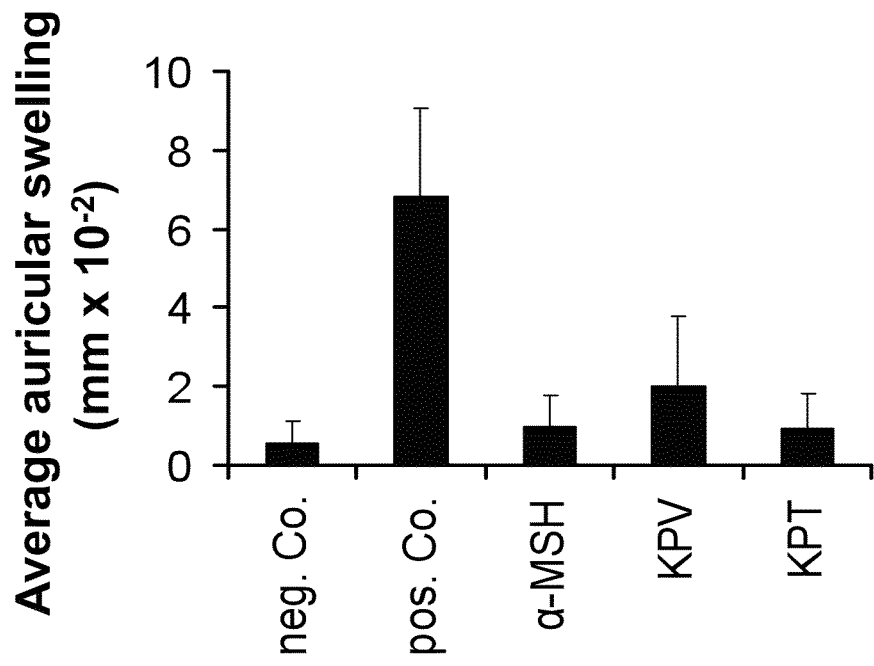
FIG. 1 shows that intravenous injection of αMSH, KPV or KPT suppresses the CHS sensitization phase.

The following examples are intended to explain the invention in more detail. As used herein, the term "KdPT" or "KPT" refers to the isomer (L)Lys-(D)Pro-(L)Thr.

The experimental data below shows that the peptides KdPT and KP are effective in the treatment of multiple inflammatory disorders as they interfere with basic mechanisms of inflammation. In particular, Examples 7 and 8 make it plausible that KP and KdPT are effective against various autoimmune disorders. Examples 7 and 8 show that KdPT and KP lead to the induction of tolerant dendritic cells and subsequently to the generation of regulatory T cells. Antigen recognition by the dendritic cells and the resulting activation of T cells is of central importance for autoimmune disorders. KdPT and KP influence these steps such that the result is not an immune activation but a tolerance induction.

Furthermore, KdPT has the effect that activation of transcription factor NF-κB (which is relevant for many inflammatory and immune reactions) is reduced, see Example 5. Also, this aspect supports the notion that KdPT is effective in the treatment of various different autoimmune disorders as well as allergies including enterocolitis, Crohn's disease, ulcerative colitis, psoriasis, rheumatoid arthritis, multiple sclerosis, vasculitis, allergic reactions, food allergies, asthma, contact allergies, rhinitis, atopic dermatitis, transplant rejection, scleroderma, fibroses and inflammatory disorder of the blood vessels. Autoimmune diseases particularly include but are not limited to multiple sclerosis, vasculitis, rheumatoid arthritis, psoriasis, Crohn's disease and ulcerative colitis.

EXAMPLE 1

Mice:

7 to 10 week old female Balb/C mice were obtained from Charles River (Sulzfeld, Germany) and kept in compliance with government regulations.

Administration of αMSH or KPV or KPT or KP:

αMSH and the peptides were stored as aliquots at −20° C. until used. Before the injection, the particular compound was dissolved in PBS, 0.1% mouse serum, and stored on ice until injected i.v. into the tail vein of the mice. 5 μg of αMSH or 1.5 μg of peptide (KP: 50 μg) per mouse were injected 2 hours before the sensitization.

Determination of CHS and Tolerance:

The mice were sensitized by spreading 75 μl of 0.5% DNFB in acetone/olive oil (4:1) on the shaven abdomen of naive mice. CHS was induced by applying 10 μl of 0.3% DNFB to the ears of the mice on both sides of one ear. CHS was determined by the degree of auricular swelling of the hapten-exposed ear compared with the other, control-treated ear and was measured using spring-loaded dividers 24 hours after hapten exposure. Mice whose ears were exposed to hapten without previous sensitization served as negative controls. In order to determine whether the injection of αMSH or peptides before hapten administration leads to induction of tolerance, mice underwent i.v. injection (abdomen) or exposure (left ear) as described with αMSH or peptides 2 hours before the sensitization. To confirm the αMSH-induced suppression of CHS, mice were exposed to hapten on one ear 7 days after the sensitization, and the auricular swelling response was determined 24 to 36 hours later. 14 days later, the same mice were sensitized once again on the shaven back (now in the absence of exogenous αMSH), and investigated for their ability to induce a CHS response by a second exposure to hapten on the right ear one week later.

Topical preparations of αMSH were used in some experiments. In these experiments, application to the mice took place at the sensitization site (abdomen) immediately before or 3 hours or 24 hours before the sensitization.

Result:

i.v. injection of αMSH and of KPV or KPT or KP inhibits the ability of the mice to induce a CHS response to DNFB exposure taking place 7 days later. These mice thus developed no DNFB-specific sensitization. KPT suppressed the CHS response most effectively (see FIGS. 1 and 13b).

Figure 2:
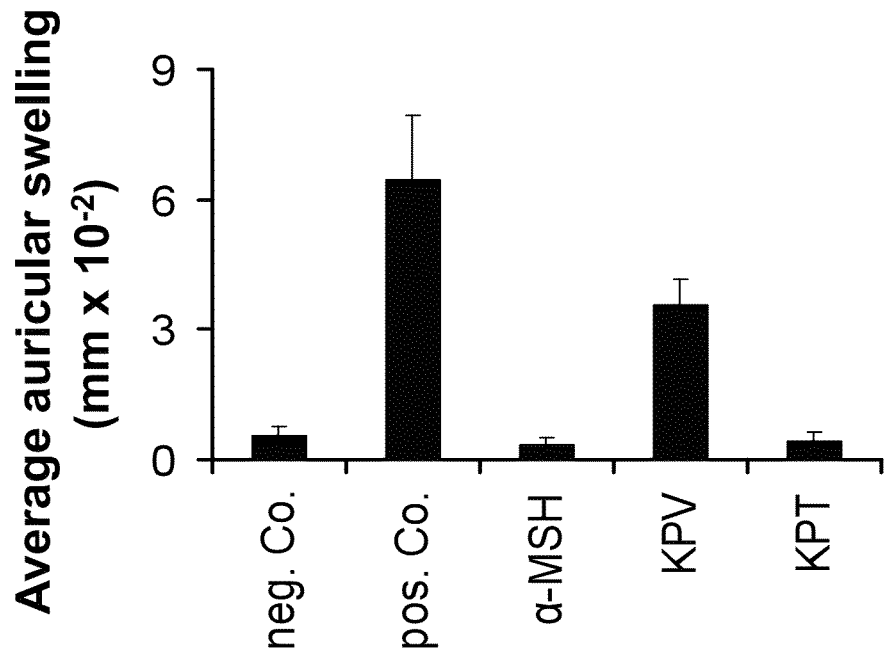
FIG. 2 shows that intravenous administration of αMSH, KPV or KPT is able to induce tolerance.

In order to distinguish between temporary immunosuppression and specific immunological tolerance, mice were sensitized a second time and exposed to hapten. Mice injected with αMSH or KPV or KPT before the first sensitization could not be sensitized even by administration of a second sensitizing dose of hapten, which indicates that these mice have developed tolerance to DNFB. KPV showed a weak effect, whereas αMSH and KPT and KP inhibited the auricular swelling response very greatly (see FIGS. 2 and 13b).

EXAMPLE 2

Material and Methods:

Mononuclear cells (PBMC) were separated from human buffy coats by Ficoll Hypaque density gradient centrifugation. Cells (1×106 per ml), cultivated in RPMI 1640 with antibiotics and 10% FCS, were either not treated or stimulated with αMSH or the peptides KPV or KPT with or without IL-1β (10 U/ml). The supernatants of the PBMC cultures were collected after incubation for 24 or 48 hours and stored at −20° C. until used further. A commercially available ELISA was employed to detect IL-10.

Figure 3:
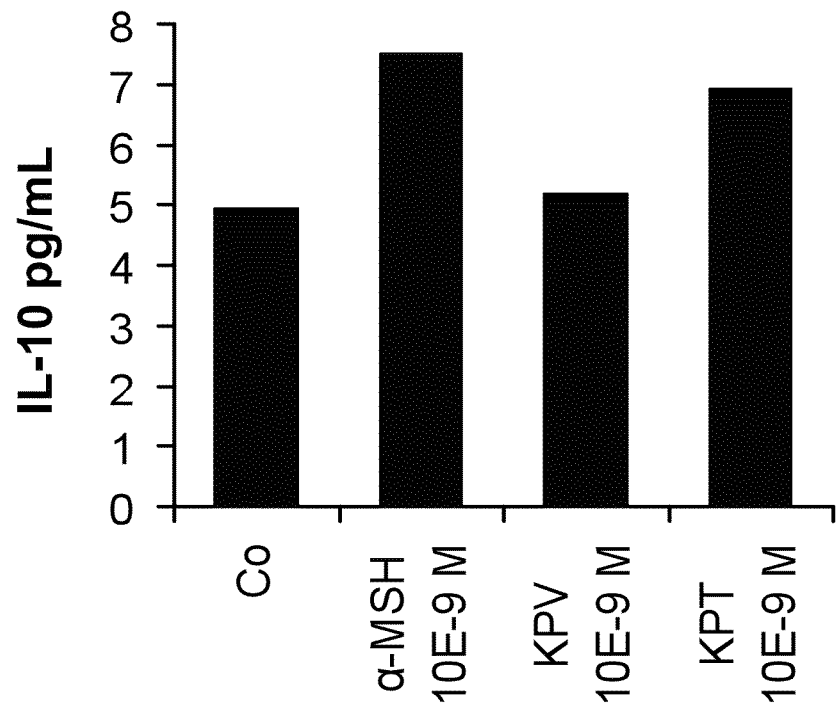
FIG. 3 illustrates IL-10 secretion by human PBL 24 hours after treatment with αMSH, KPV or KPT.

Results:

Human PBMC which were untreated or had been treated with various concentrations of αMSH or peptides produced only low concentrations of IL-10 (5-10 pg/ml) after incubation for 24 hours. αMSH ($10^{-11}$ M), KPV ($10^{-8}$ to $10^{-9}$ M) and KPT ($10^{-8}$ to $10^{-9}$ M) evidently induced IL-10 production (see FIG. 3).

Figure 4:
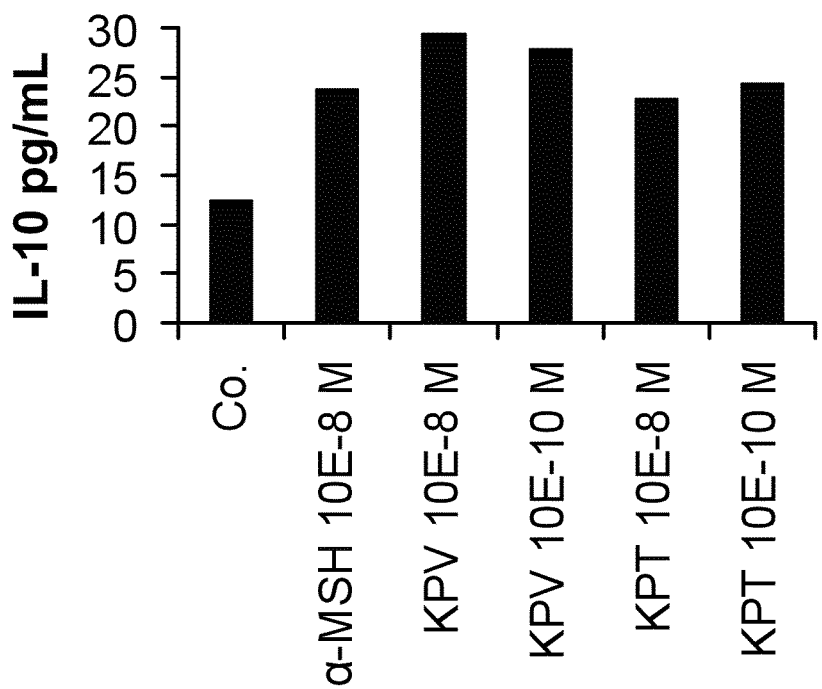
FIG. 4 illustrates IL-10 secretion by human PBL 48 hours after treatment with αMSH, KPV or KPT.

The human PBMC produced significant amounts of IL-10 after incubation for 48 hours. αMSH, KPV and KPT significantly increased the production of IL-10 by human PBLC. There was no essential difference between αMSH and the peptides (see FIG. 4).

The results which are shown prove that the peptide KPT is able, like αMSH and KPV, to inhibit the sensitization of CHS after intravenous administration and to induce hapten-specific tolerance. KPT is also able to induce IL-10 in vivo and in vitro. The data also make it probable that the immunosuppressant effect of αMSH in vivo depends not just on IL-10 induction.

EXAMPLE 3

Material and Methods:

All the steps were carried out at 0 to 4° C. The monocytic cell line THP-1. was washed once in PBS, once one acidic glycine buffer (50 mM glycine, 100 mM sodium chloride, pH 3) and three times with RPMI. The cells 2.5×$10^6$ per ml) were then resuspended in 100 μl of RPMI/1% BSA and transferred into 96-well microtiter plates. After addition of biotin-labeled αMSH ($10^{-10}$ M), the cells were incubated at 4° C. for 1 hour, washed once with PBS, resuspended in 100 μl of PBS/1% BSA and incubated with FITC-labeled streptavidin (40 μg/ml) in the dark at 4° C. for 30 minutes. After a last washing step, the cells were resuspended in PBS. The amount of bound biotin-labeled αMSH was analysed using a flow cytometer. In control experiments, the cells were incubated without biotin-labeled αMSH but in the presence of FITC-streptavidin. Dead cells were excluded by adding propidium iodide shortly before the FACS analysis. The specificity of the binding of the biotin-labeled MSH was determined by adding unlabeled αMSH ($10^{-6}$ to $10^{-12}$ M) or KPV or KPT ($10^{-6}$ to $10^{-12}$ M)

Figure 5:
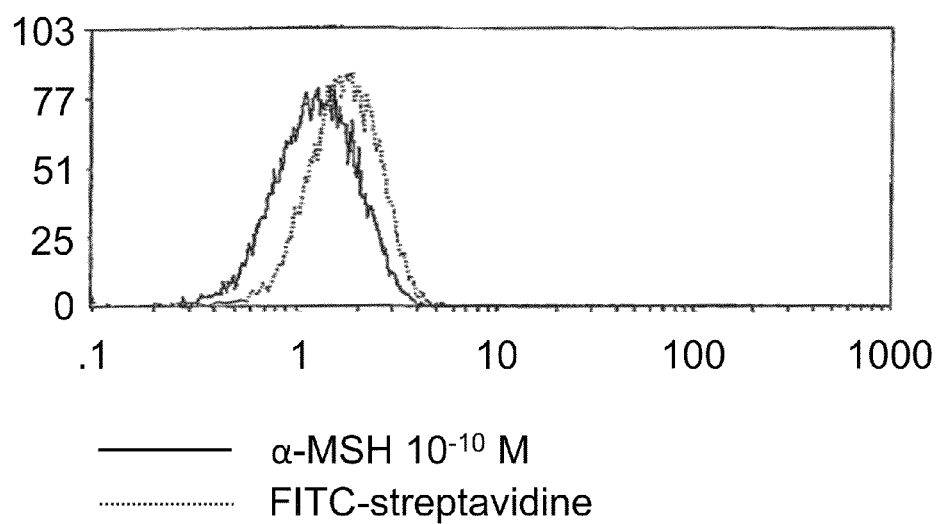
FIG. 5 shows that THP-1 cells express receptors for αMSH.
Figure 6A:
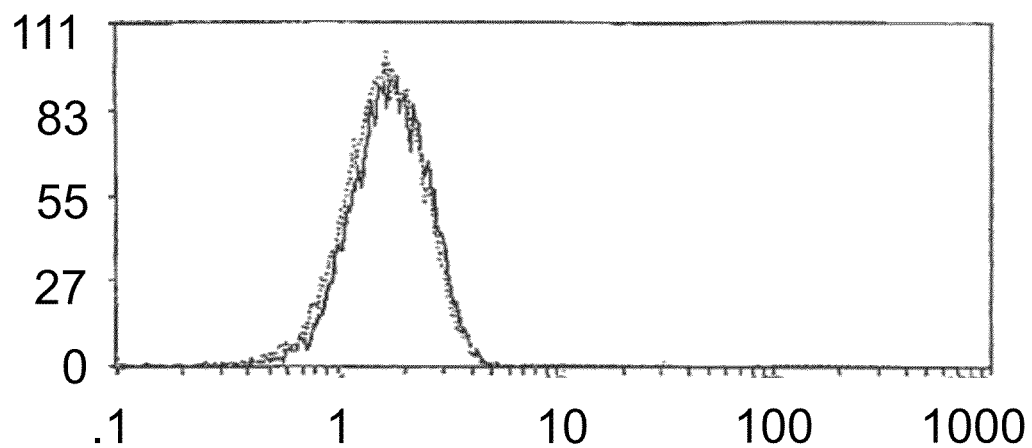
FIGS. 6a to d, 7a to d, and 8a to d, show that unlabeled αMSH, KPV or KPT are able to displace biotin-labeled αMSH from binding sites on THP-1 cells in a competitive assay.
Figure 6B:
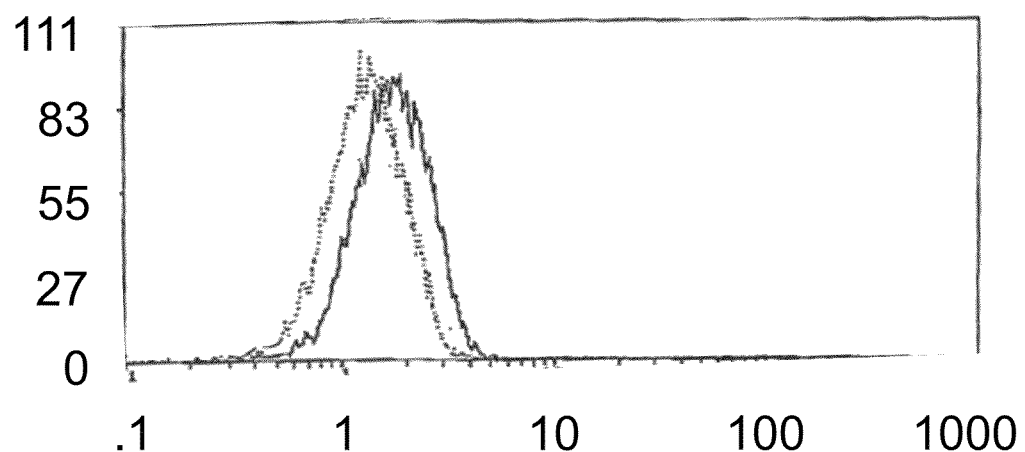
Figure 6C:
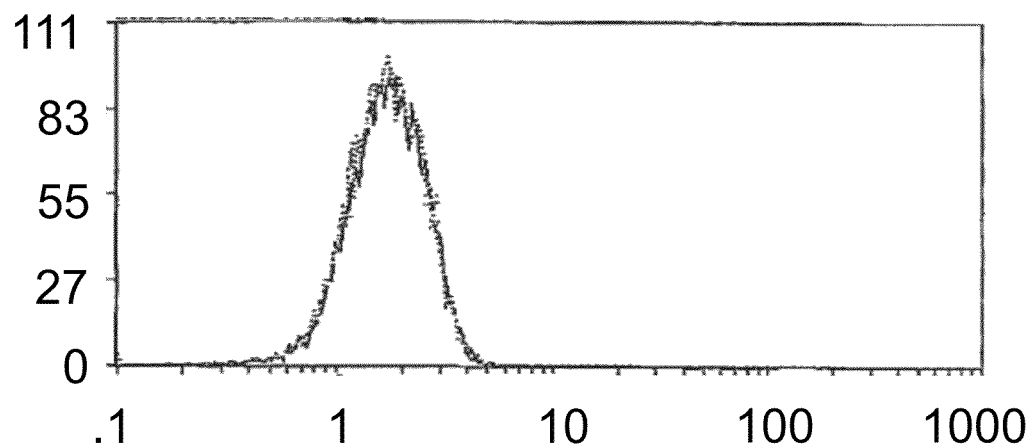
Figure 6D:
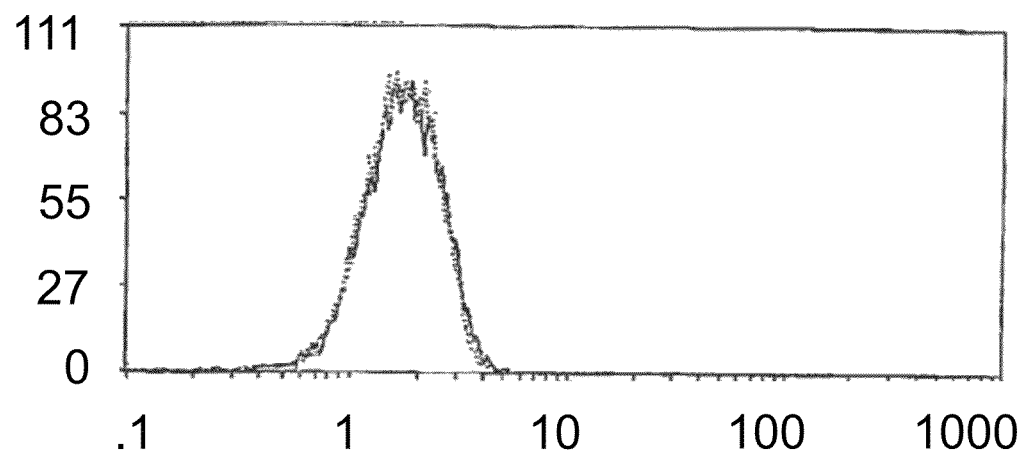
Figure 7A:
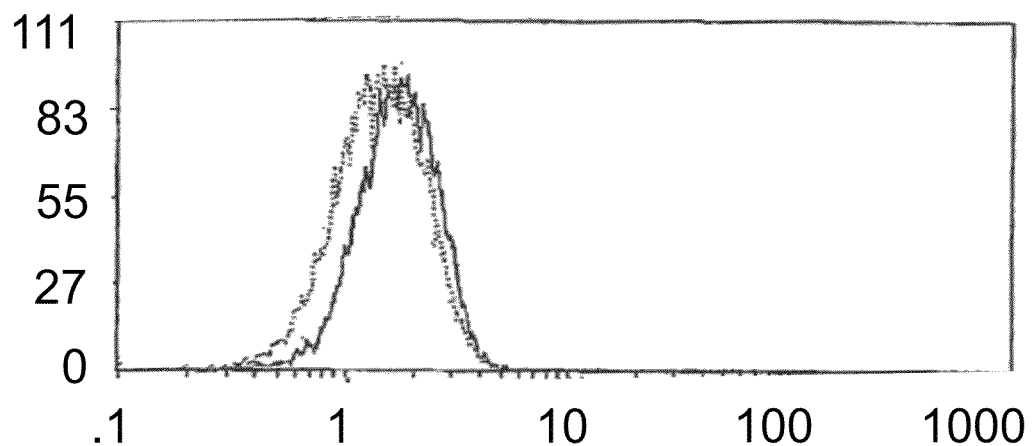
Figure 7B:
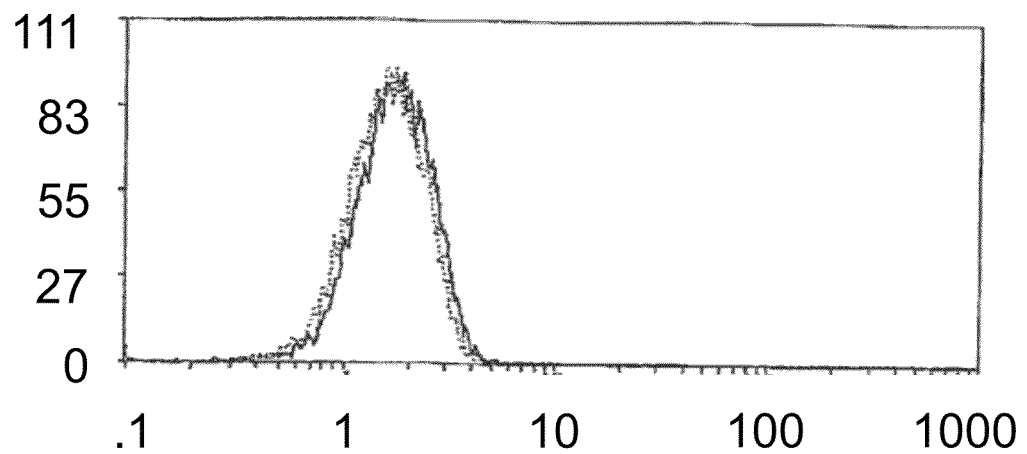
Figure 7C:
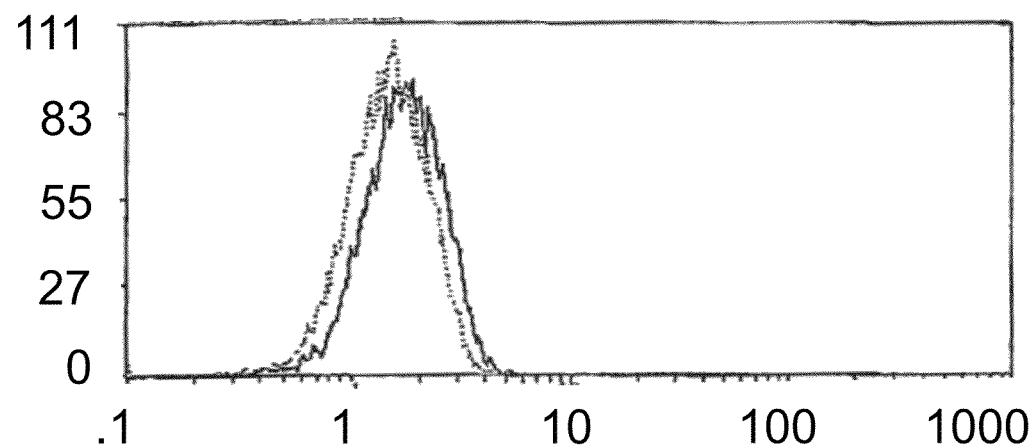
Figure 7D:
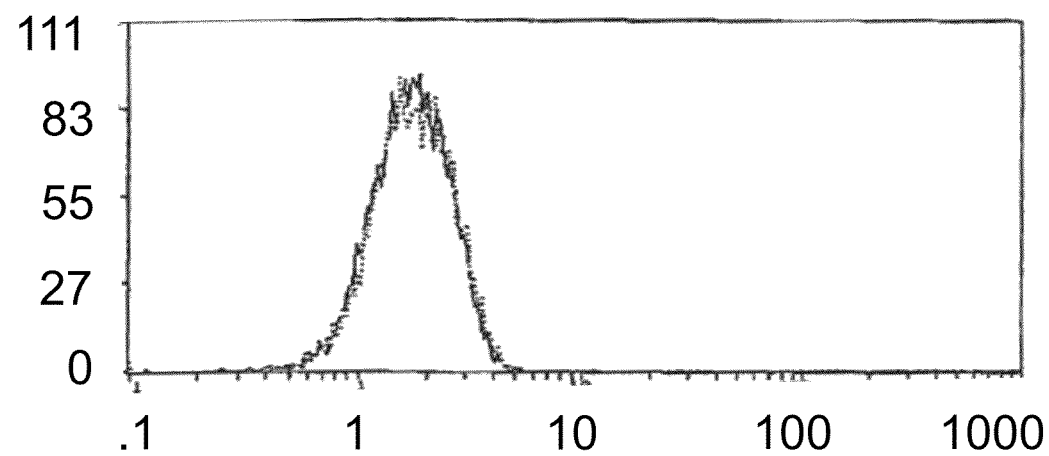
Figure 8A:
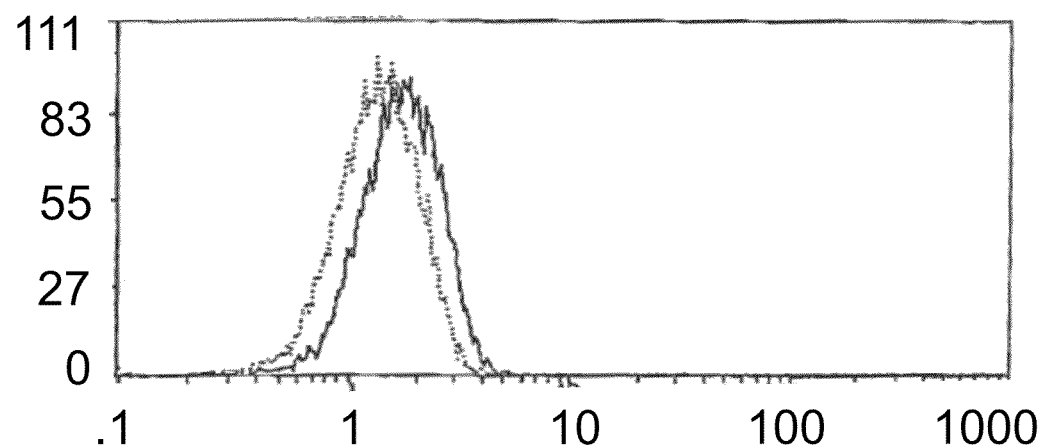
Figure 8B:
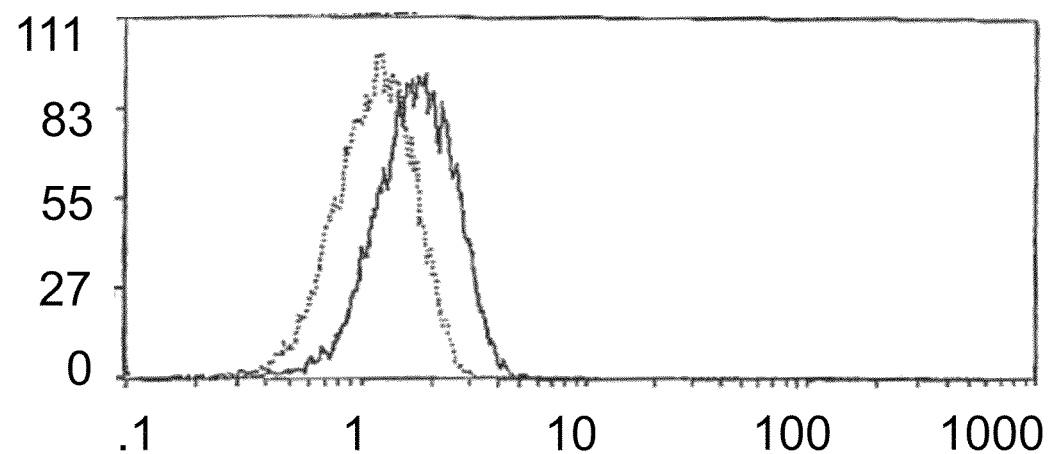
Figure 8C:
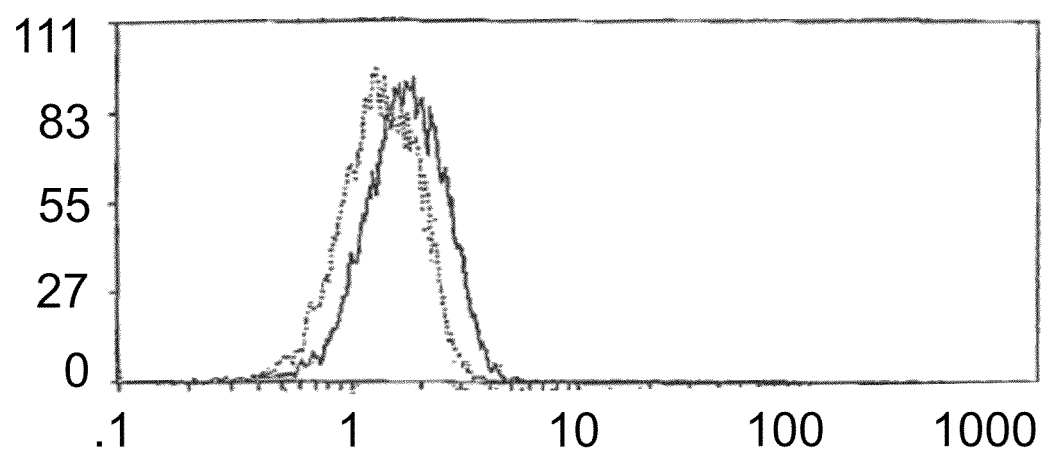
Figure 8D:
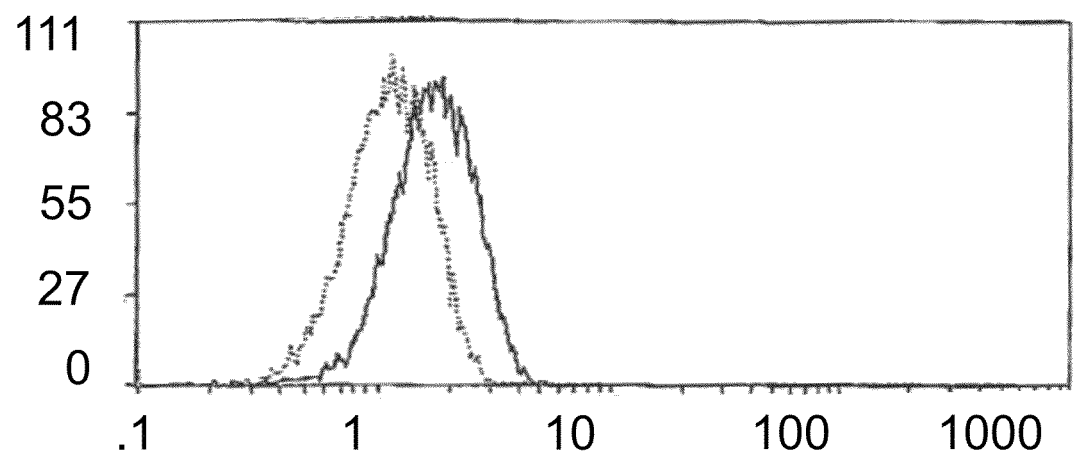

Results:

According to FACS analysis with biotin-labeled αMSH, unstimulated THP-1 cells express significant amounts of binding sites which are specific for αMSH compared with control mixtures incubated only with FITC-streptavidin. The concentration of αMSH employed in this experiment was $10^{-10}$ M (see FIG. 5).

In order to determine whether THF-1 cells express one of the known melanocortin receptors (MC), RT-PCR was carried out with MC-1-, MC-2-, MC-3- and MC-4-specific primers. Total RNA was obtained from THP-1 cells. A PCR product specific for MC-1 with an expected length of 416 bp was detected (Rajora et al., 1996, J. Leuk. Biol., 59, 248). PCR products specific for MC-2, MC-3 or MC-4 were not detected. The results show that THP-1 cells express MC-1 which, in contrast to other melanocortin receptors, is specific for αMSH and ACTH.

In order to investigate whether the binding sites expressed on THP-1 are specific for αMSH, competition experiments were carried out with αMSH or KPV or KPT.

The specific binding was measured by incubating THP-1 cells with biotin-labeled αMSH ($10^{-10}$ M) and various concentrations of unlabeled αMSH or peptides. Unlabeled αMSH in a concentration of $10^{-6}$ significantly suppressed αMSH binding. No significant suppression was observable when αMSH was employed in concentrations of $10^{-6}$M, $10^{-10}$ M or $10^{-12}$M (FIGS. 6a to 6d)

When unlabeled KPV was employed, a significant inhibition was observable only at a concentration of $10^{-6}$ M (see FIGS. 7a to 7d).

In the case of the peptide KPT, a significant inhibition of αMSH binding was observable at each of the tested concentrations. ($10^{-6}$ to $10^{-12}$M, see FIGS. 8a to 8d).

These results show that the KPT peptide binds to the melanocortin receptor on THP-1 cells which is specific for αMSH, which indicates that αMSH and KPT have a common binding site. However, since KPT shows competition for receptor even at very low concentrations, it is probable that this peptide in fact has a higher affinity for MC-1 receptor than MSH.

EXAMPLE 4

Material and Methods:

Human dermal microvascular endothelial cells (HDMEC) and the cell line HMEC-1 (human microvascular endothelial cell line 1) were treated either with TNFα or LPS in the presence or absence of one of the peptides. The cells were harvested for RNA isolation after 3 and after 6 hours after treatment or harvested either for adhesion molecule ETA or FACS analysis 3, 6, 16 or 24 hours after treatment. RNA underwent reverse transcription, and samples were subjected to a PCR for E selectin, ICAM-1, VCAM or for β-actin as housekeeping gene in order to carry out a semiquantitative determination. For the lymphocyte adhesion assay, the endothelial cells were seeded in dishes and incubated with $^{51}$Cr-labeled lymphocytes. After a washing step, the amount of remaining lymphocytes bound to the EC layer was determined by measuring the radioactivity in the samples.
Results:

Treatment of the endothelial cells with αMSH or KPT inhibited the LPS- or TNFα-induced expression of adhesion molecules. This effect was observed in a concentration range from $10^{-6}$ to $10^{-12}$M αMSH or peptide. The peptide KPT had the strongest effect on the expression of adhesion molecule mRNA.

Figure 9A:
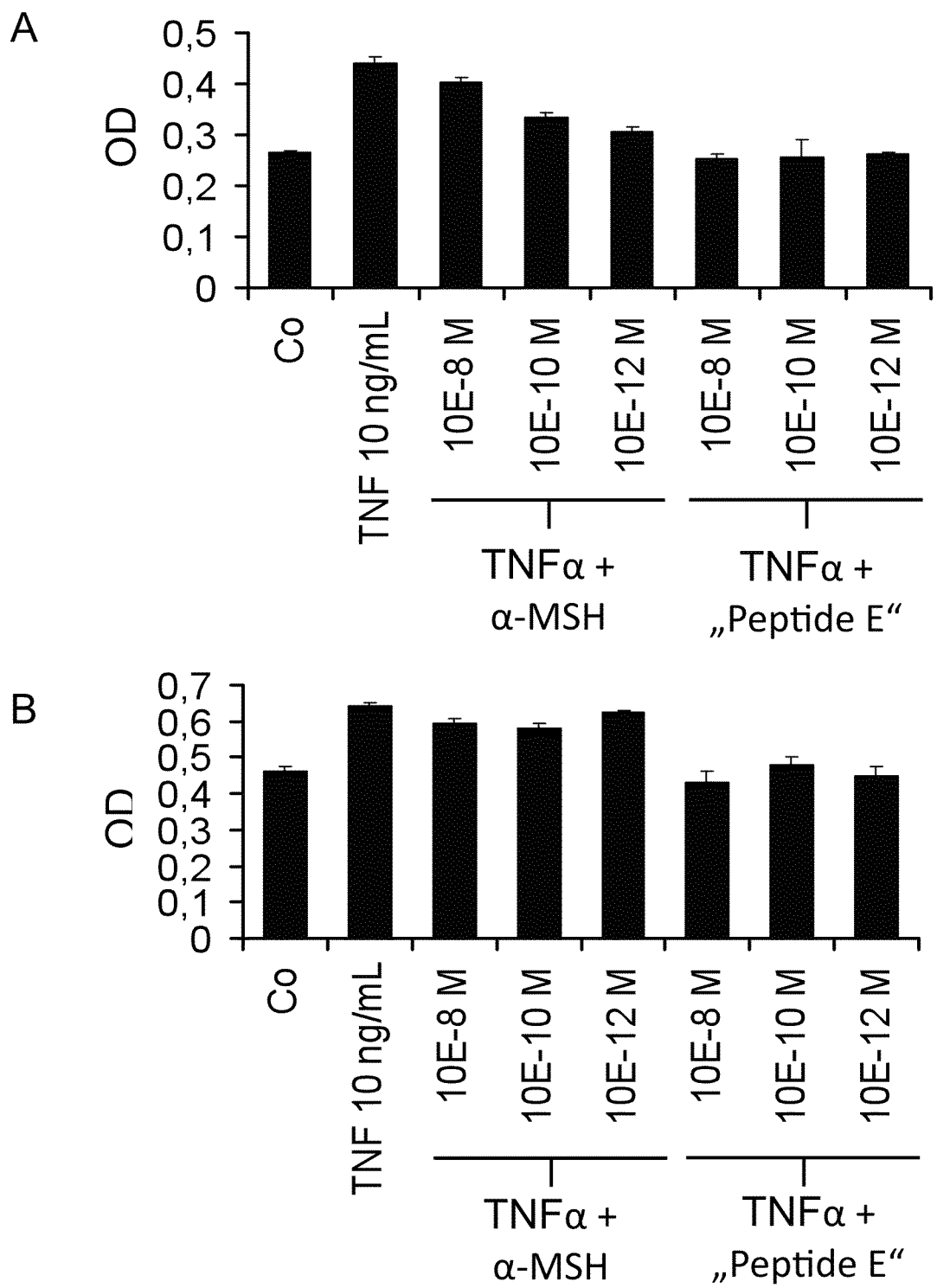
FIG. 9a shows the expression of cell adhesion molecules (CAMS) on the surface of HMEC-1 cells 24 hours after treatment by TNFα+αMSH or TNFα+KPT.
Figure 9B:
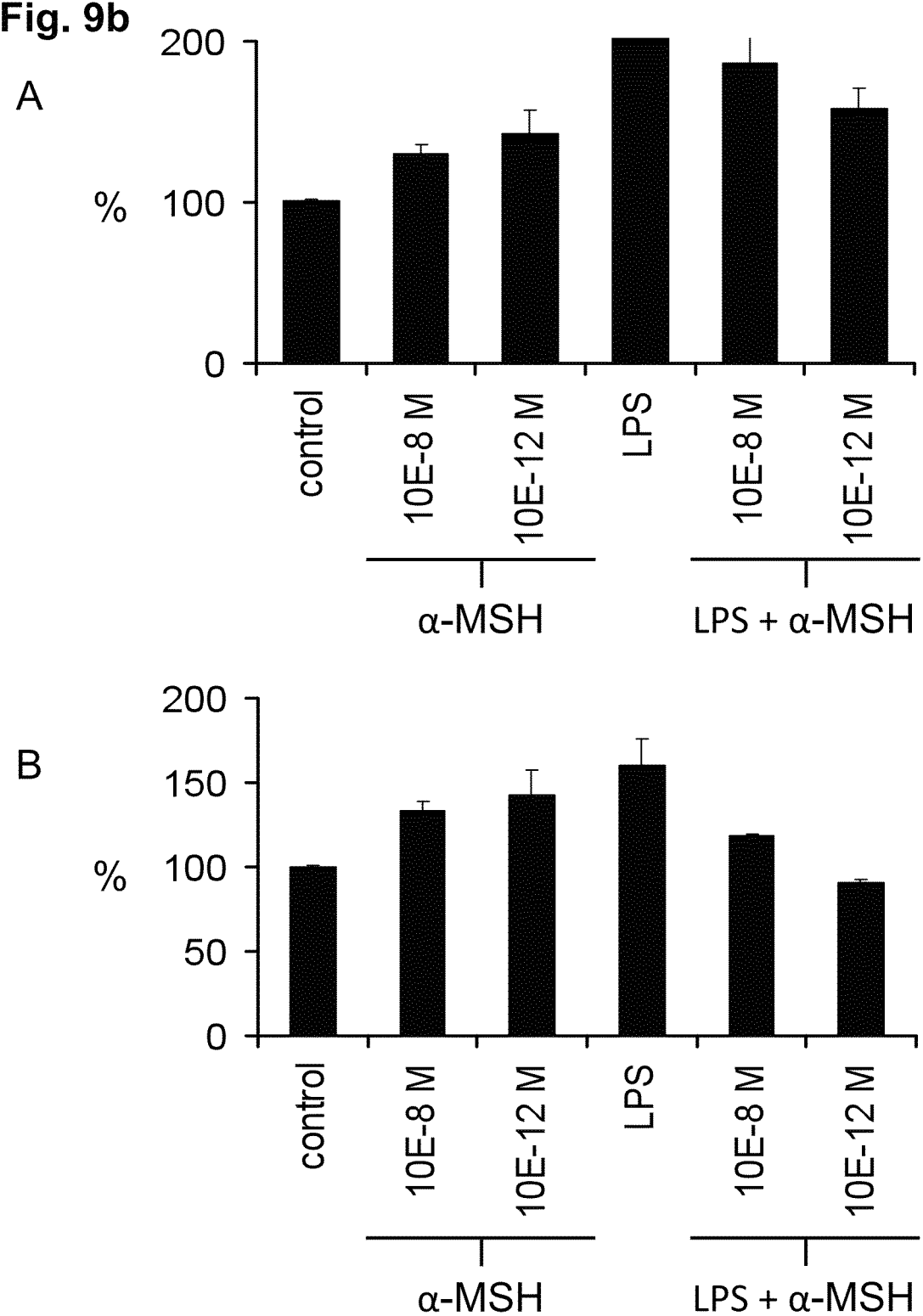
FIG. 9b shows the adhesion of lymphocytes to HDMEC (chromium release assay). A: molt4 T lymphocytes; B: JY B lymphocytes.

The LPS- or TNFα-induced surface expression of adhesion molecules was reduced to, a small extent by all the agonists. These data were obtained both by EIA, in which case whole cells were employed, and by FACS with specific antibodies (see. FIG. 9a, which shows EIA data).

αMSH significantly reduces the binding of T and B cells to LPS- or TNF-αMSH-treated EC layers (see FIG. 9b). Taken together, these results show that αMSH has an effect on the adhesion of lymphocytes to EC and thus also reduces the extravasation of lymphocytes in conditions of tissue inflammation. This is supported by the in vivo data on localized vasculitis.

EXAMPLE 5

Figure 10:
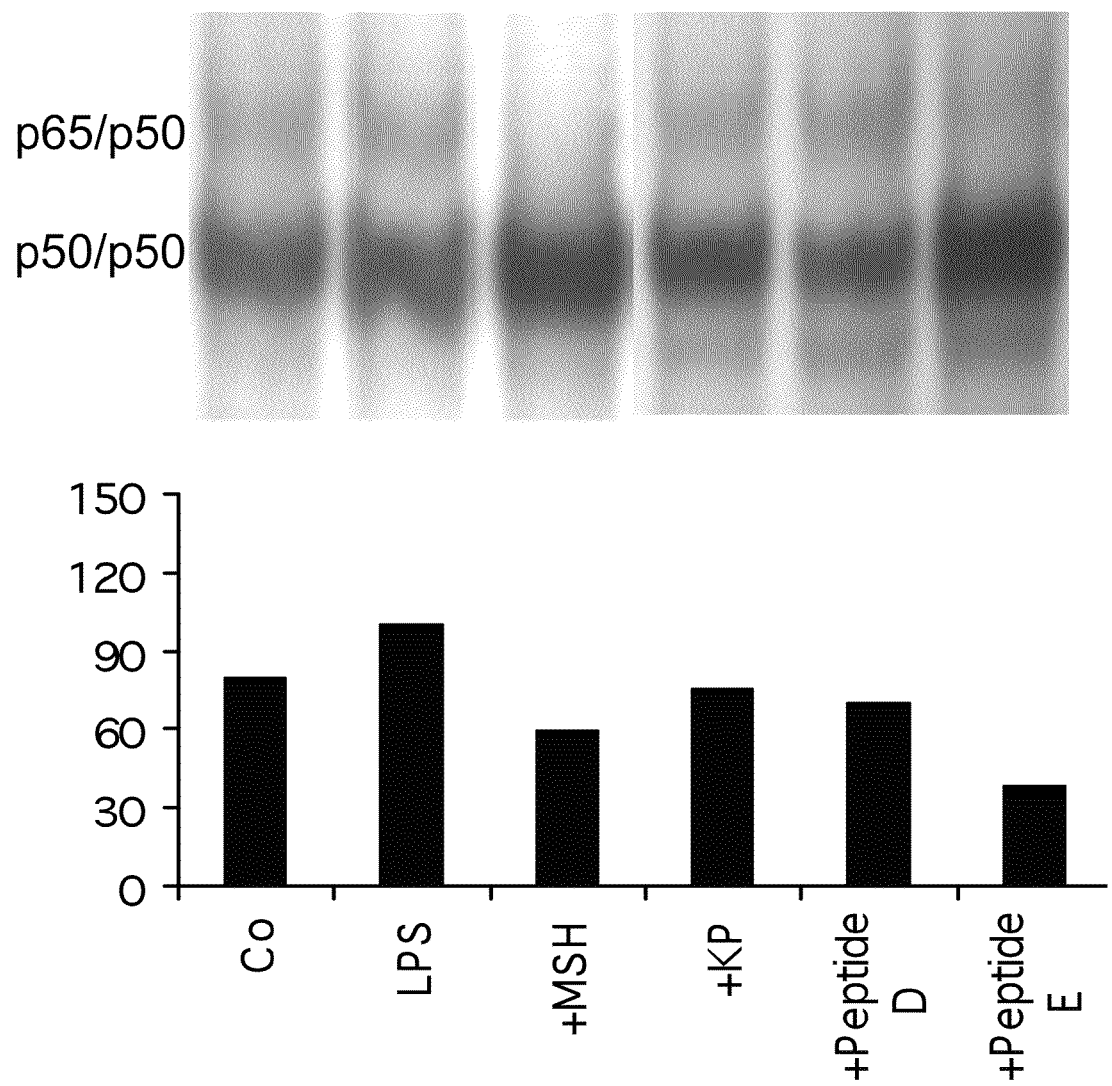
FIG. 10 shows the effect of αMSH, KP, KPV or KPT on NF-κB activation in LPS-treated HMEC-1 cells.
Figure 13A:
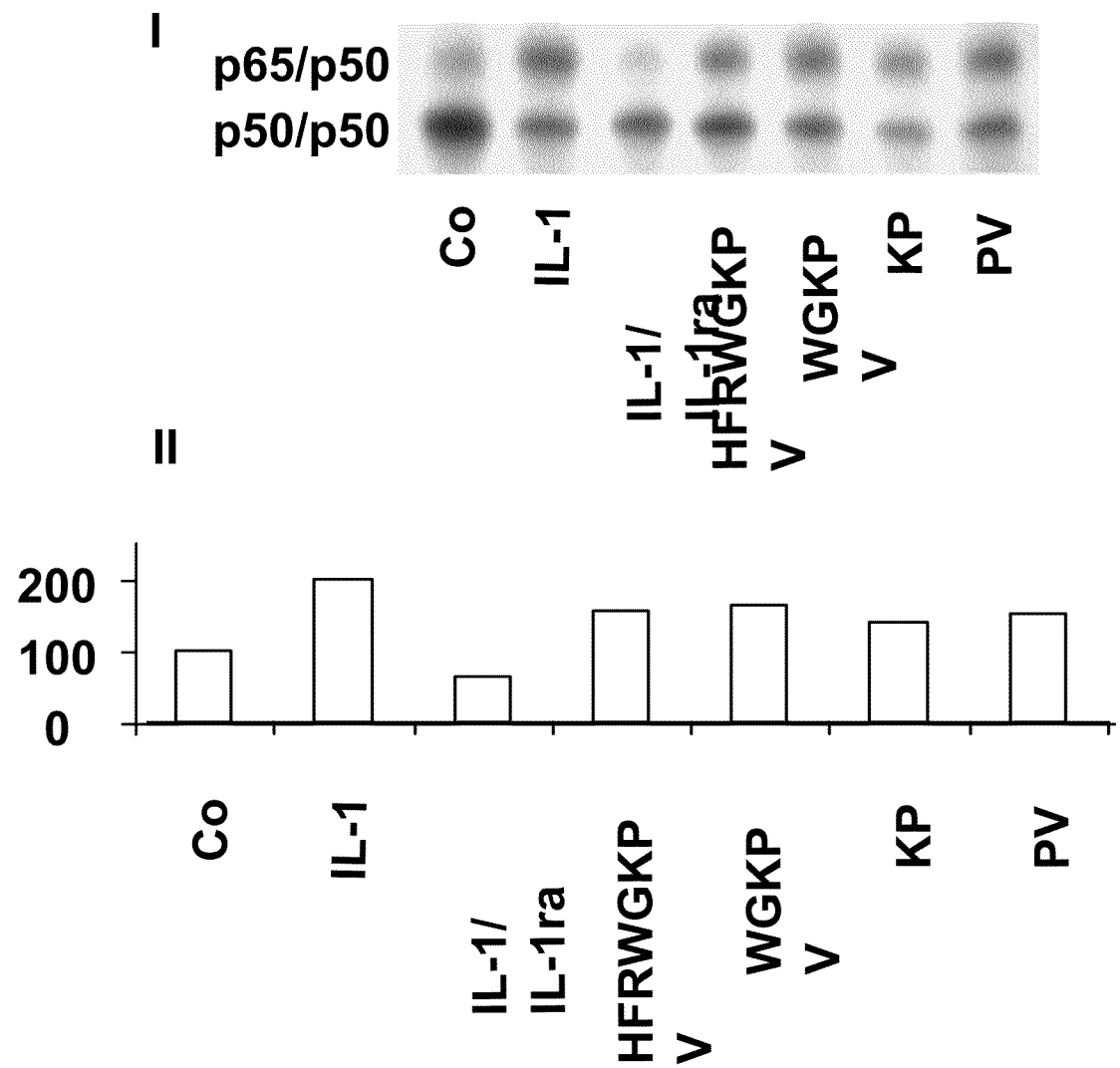
FIG. 13a shows that in an NF-κB band shift assay the intensity of the NF-κB p65/p50 heterodimer band is reduced by various αMSH-derived peptides.
Figure 13:
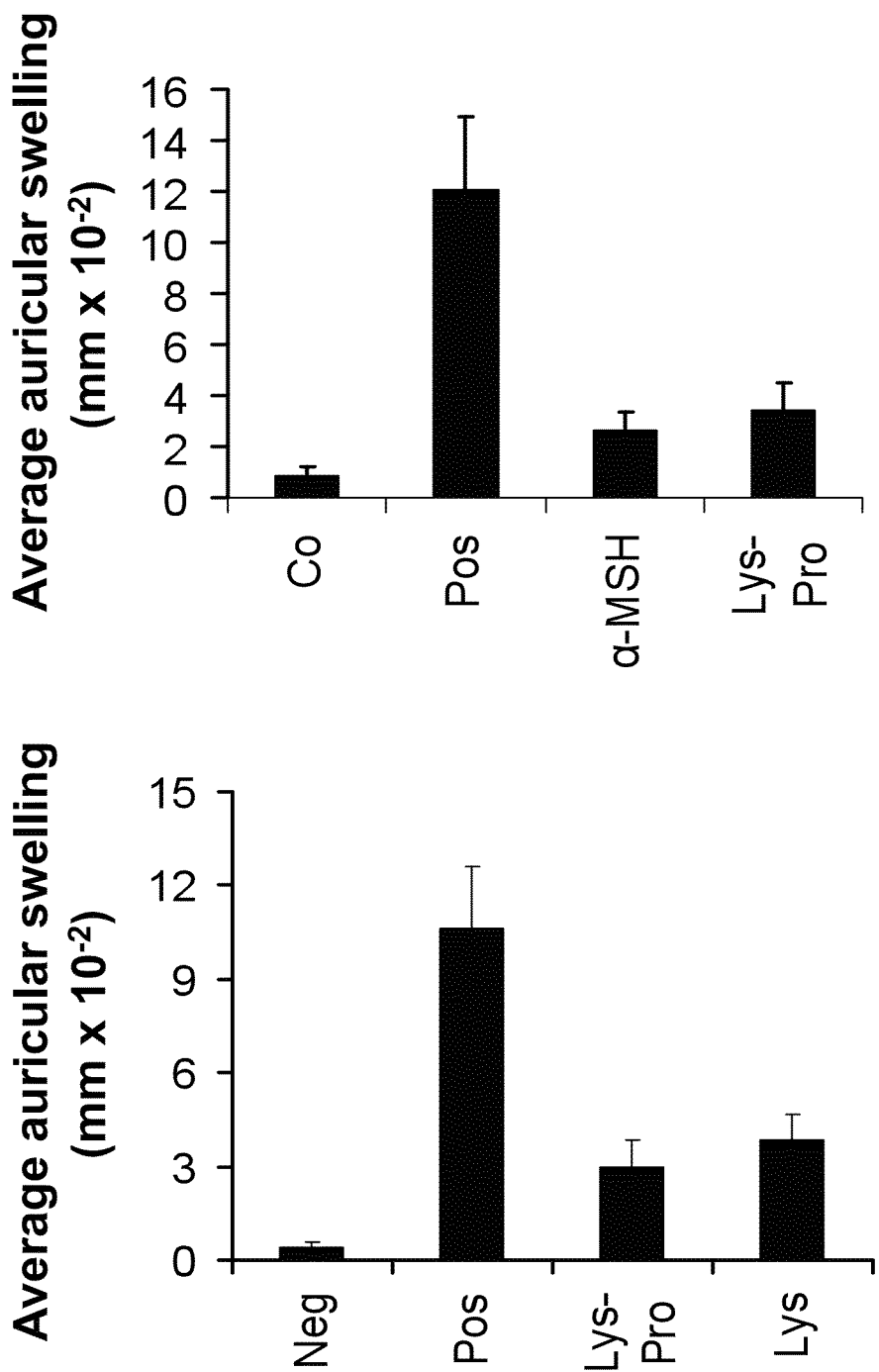
FIG. 13b shows the effect of αMSH, KP or K on the CHS reaction and the effect of αMSH or KP on the induction of tolerance in BalbC mice.
Figure 13:
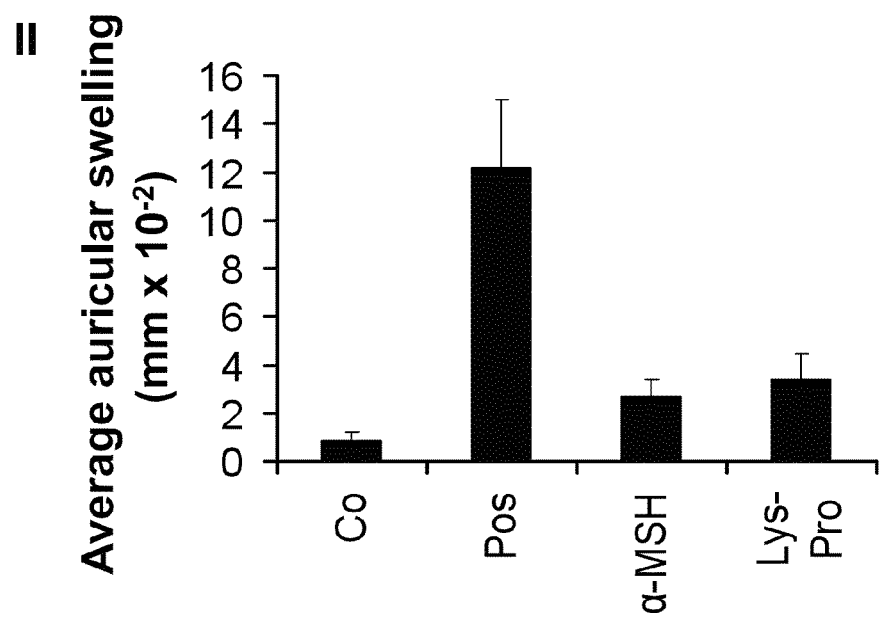

Material and Methods:

Epidermal cells (ECs) or normal human keratinocytes (HNK) were treated with IL-1, LPS or TNFα in the presence or absence of peptides. After 15 or 30 minutes, the nuclear proteins were obtained and subjected to an electrophoretic mobility shift assay (EMSA) with radiolabeled oligonucleotide with NF-κB-specific binding sequence. Unlabeled oligonucleotide was used as competitor. In some experiments, antibodies against the p65 or p50 chain of NF-κB were used in order to confirm the identity of the detected bands as either p50 homodimer or p50/p65 heterodimer.
Result:

Addition of the peptides in TNFα- or LPS-treated ECs and in IL-1-treated HNKs leads to a reduced activation of the transcription factor NF-κB (see FIGS. 10 and 13a). This in turn leads to a diminution in the transcription of the genes for numerous proinflammatory mediators (cytokines, chemokines, adhesion molecules, etc.). The identity of the observed bands in the EMSA as NP-κB heterodimer was confirmed by using anti-p65 antibody.

EXAMPLE 6

Figure 11:
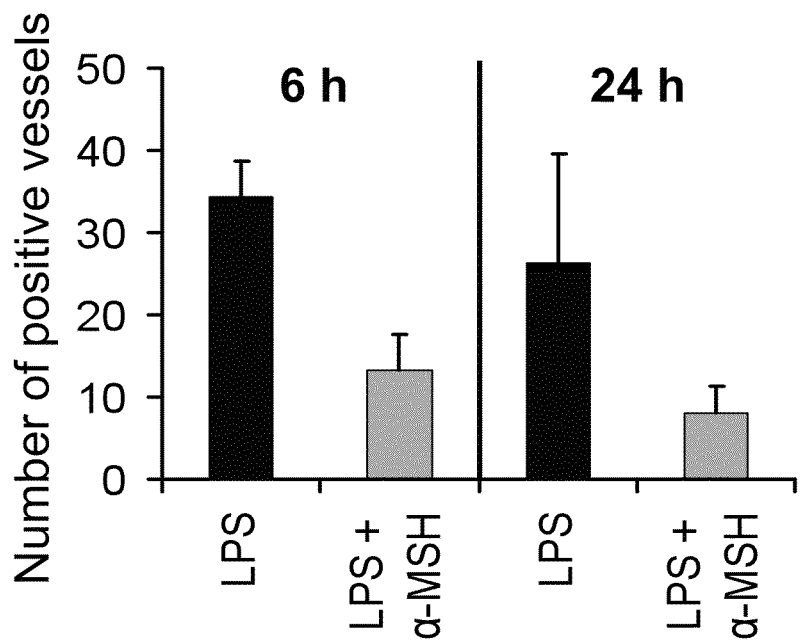
FIG. 11a shows that the number of E selectin-expressing vessels in tissue sections is reduced by αMSH treatment.
FIG. 11b shows that the number of petechial lesions on the ears of LPS-treated mice is reduced by αMSH treatment.

Material and Methods:

Mice were treated with LPS by s.c. injection on one ear. This preparatory injection induces a long-lasting rise in E selectin expression at the site of the LPS injection. 24 hours later, a second LPS dose was injected i.p. (challenge). This second LPS injection leads to rapid vessel necrolysis and to the formation of petechial lesions which are easily measurable because of their size and number. αMSH (25 µg) was administered at the time of the preparatory LPS injection.
Result:

Injection of αMSH at the time of the preparatory LPS administration inhibits the induction of local E selectin expression in the ear (see FIG. 11a) and significantly reduces the number and size of the petechial lesions formed after the challenge injection of LPS (see FIG. 11b).

EXAMPLE 7

Material and Methods:

Bone marrow dendritic cells (BMDC) were isolated from the femoral bones of mice and treated with IL-4 and GMCSF for 6 or 9 days. On day 6 or 9, the cells were treated with αMSH ($2\times10^{-11}$ M) or the peptide KP ($2\times10^{-6}$M) 3 hours and 2.5 hours before reinjection into naive mice with the same genetic background. 2 hours before reinjection, the cells were treated with hapten (1 mM DNBS, the water-soluble form of DNFB). Immediately before the reinjection, the cells were washed 2× with PBS. $5\times10^{-5}$ cells were injected i.v. into each animal. Control cells were treated either with DNBS alone or with αMSH alone or were left untreated. 5 days after injection, the animals were contacted with DNFB on the ear, and the ear thickness was measured the next day. 2 weeks later, the animals were resensitized with DNFB and again recontacted on the ear 5 days later. Finally, the auricular swelling was measured.
Results:

Recipient animals injected with untreated cells or αMSH-treated cells showed no immune response after the first challenge, as expected. Recipient animals injected with DNBS-treated BMDC showed an appropriate CHS reaction at the time of the first challenge. This reaction was suppressed in animals injected with cells previously treated with TNBS and αMSH or TNBS and KP in vitro. Thus, contact of DCs with αMSH or peptide is sufficient to induce inhibition of CHS (see FIG. 12).

Figure 12:
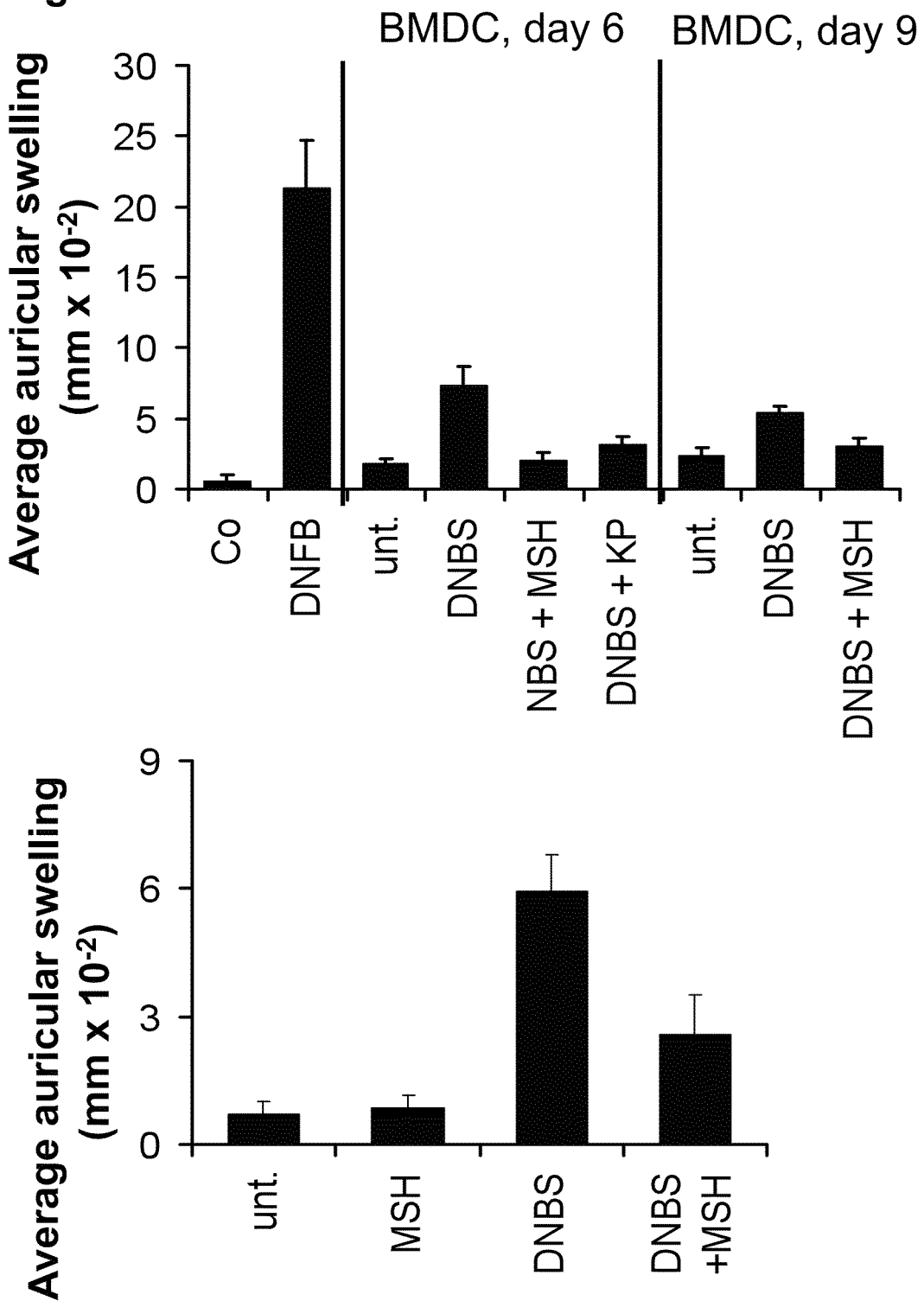
FIG. 12 shows that in vitro treatment of BMDC with αMSH or KP suppresses CHS and can induce tolerance.

At the time of the second challenge and of the corresponding resensitization, animals again injected with DNBS-treated cells showed no immune response, whereas animals injected with DNBS/αMSH-treated cells showed no immune response, which indicates that the αMSH-induced tolerance is likewise mediated by DC (see FIG. 12).

EXAMPLE 8

Immunotherapy with αMSH or αMSH-derivative-treated Dendritic Cells or T Cells

Dendritic cells (DC) were isolated (from blood, bone marrow or tissue). It is, however, also possible to use cell mixtures containing DC (e.g. epidermal cell mixtures) and cultivated in the presence of GM-CSF and IL-4 (preferably: 250-1000µ/ml for each of the substances).

After a maturation period (preferably 6-9 days), the cells are loaded with antigen (concentration depends on the particular antigen, likewise period) and treated with αMSH or derivatives thereof. The derivatives correspond at least to amino acids 12 and 13 of αMSH (Lys-Pro), with preference for Lys-Pro-Val-containing derivatives. D and L configurations of the AA are possible, likewise conservative AA exchanges. This leads inter alia to the possibility also of using Lys-Pro-Thr which is derived from IL-1β, and derivatives thereof with N-terminal extensions. Derivatives with C-terminal extensions can also be employed. Addition of the peptide can take place before addition of the antigen, at the same time, later, once or more than once (the preferred dose depends on the particular peptide, for αMSH e.g. $10^{-8}$ M to $10^{-14}$ M).

The cells treated in this way are then injected i.v. into the recipient organism (i.p. or s.c. would also be possible); mouse: $2 \times 10^5$ cells approximate lower limit. Depending on the antigen, it is sufficient to undertake a single injection or necessary to undertake a plurality of injections in this case. It is also possible that the injections need to be repeated after lengthy periods (no data yet available on this).

Figure 14:
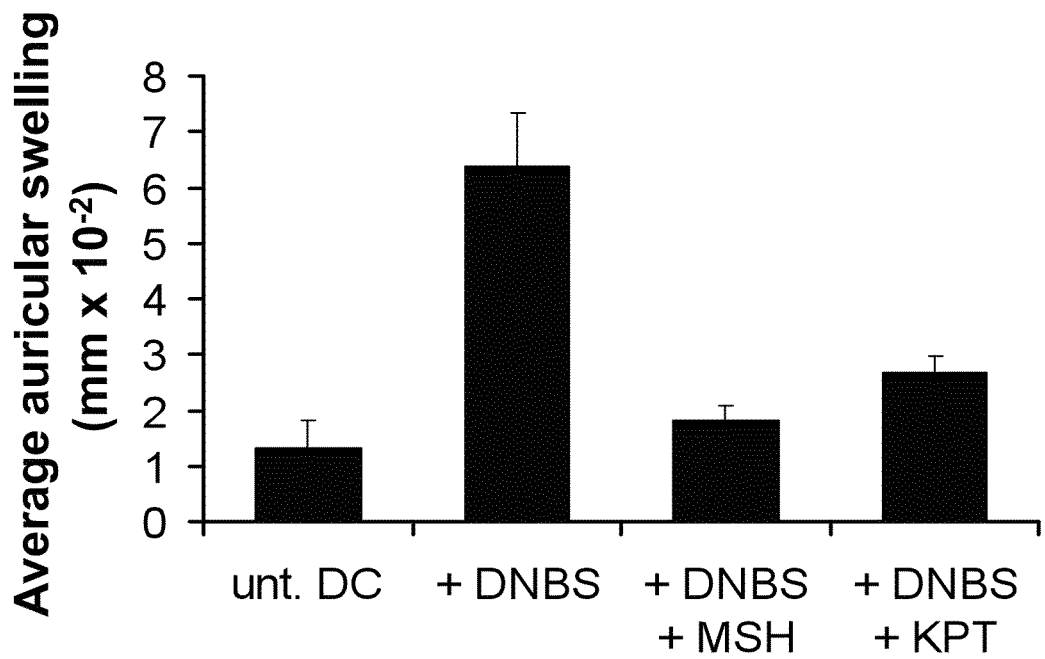
FIG. 14 shows the suppression of CHS by T cells which have been contacted in vitro with antigen-loaded and αMSH or derivative-treated DC.
Figure 15:
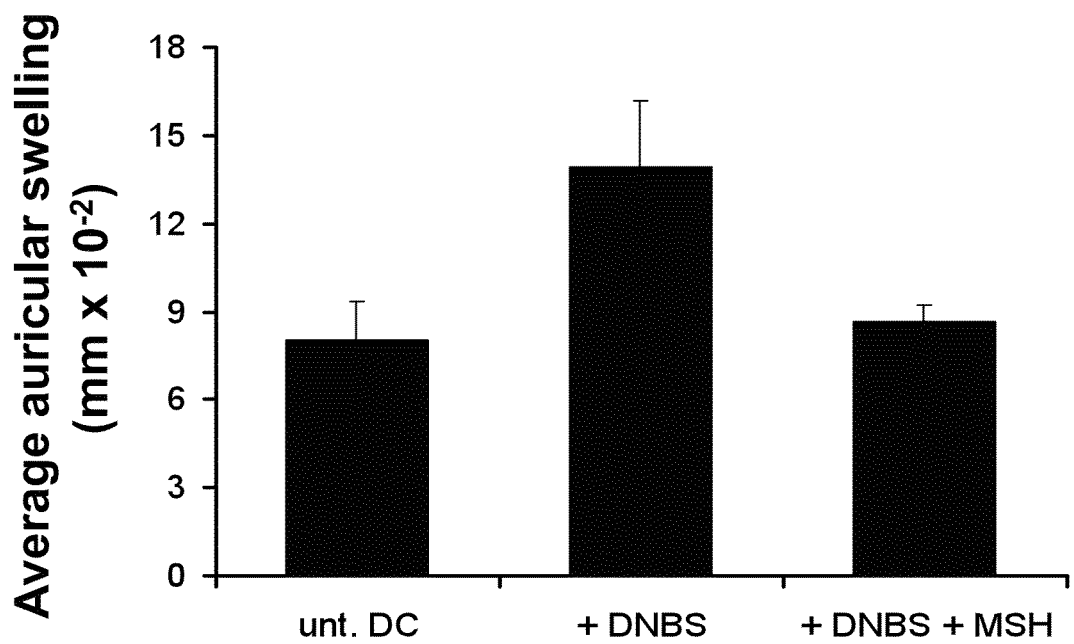
FIG. 15 shows the induction of tolerance by T cells which have been contacted in vitro with antigen-loaded and αMSH DC.

An alternative possibility is to bring DC into contact with T cells outside the body and then to inject the mixture or the T cells. In this case, the antigen loading of the DC can take place before the contact with the T cells or during it. The T cells may moreover originate from individuals which have already been sensitized to the particular antigen. The lower limit in the mouse is about 1 million T cells, with more cells being preferred (FIGS. 14 and 15).

Advantages of such a mode of use are the prevention of every type of unwanted immune response, which are antigen-specific and in which antigen-specific lymphocytes (B or T cells) play a pathogenetic part.

These include inter alia allergies, autoimmune diseases, chronic inflammations or implantations. A cure of preexistent disorders is also possible if sufficiently large numbers of cells are employed.

The surprising results can, without wishing to be bound to one theory, be regarded as the fact that αMSH is a potent immunomodulator and has numerous antiinflammatory properties. These include inter alia its property of reducing the expression of costimulatory molecules on DC. Similar properties are also shown by the αMSH derivatives of the invention, including the C-terminal tripeptide and the dipeptide Lys-Pro. Derivatives with a different amino acid composition (conservative AA exchanges) also have comparable properties, and these include in particular the Lys-Pro-Thr derived from IL-1β (so that it is to be presumed that N-terminally (analogous to αMSH) extended peptides with sequence colinear to IL-1β have the same effect).

αMSH, as well as the derivatives, are able to induce hapten-specific tolerance in vivo. DC are professionally antigen-presenting cells which are able to induce numerous types of immune responses and which also determine the course of such responses. These immune responses include in particular the T-cell-mediated immune responses.

It has now been possible to show that in vitro treatment of DC or DC/T cell mixtures with an antigen in the presence of αMSH or derivatives leads to the cells likewise inducing hapten-specific tolerance after injection into an organism.

The mechanism in this case appears to be that the antigen presentation by the DC is modulated by αMSH or derivatives in such a way that suppressor T cells are generated. It was thus possible to show that T cells in appropriate mixtures show high expression of CTLA-4 (FIG. 16). This is one of the surface molecules which characterize suppressor T cells.

It is possible with DC or T cells generated in this way to preventively impede autoimmune diseases, chronic inflammations or allergies. A cure of a preexistent pathological condition is also conceivable if sufficiently large numbers of cells are used.

The compounds of the invention can also be used for tumor treatment by means of an in situ activation of dendritic cells. It is also possible that this method can be used for tolerization in the presence of the peptides of the invention.

EXAMPLE 9

Therapeutic Treatment of Colitis Using K(D)PT

Colitis in C57BL/6 mice was induced using dextrane sodium sulfate (2% DSS in drinking water for 5 days); 1st set-up: i.p. application of 10 µg K(D)PT beginning on day 4 of DSS application; 2nd set-up: rectal application of 10 µg K(D)PT beginning one day prior to DSS application; control animals were treated with PBS; and observed parameters were body weight, histology, IL-1β expression.

In another study of chronic CD45RB high transfer-colitis using Rag2-deficient mice (n=5); transfer of $1 \times 10^6$ colitogenic T-cells; Daily application of 10 µg KDPT i.p from day 23 after cell transfer; Control animals were treated with PBS; parameters measured were body weight, histology, IL-1β expression.

Figure 17:
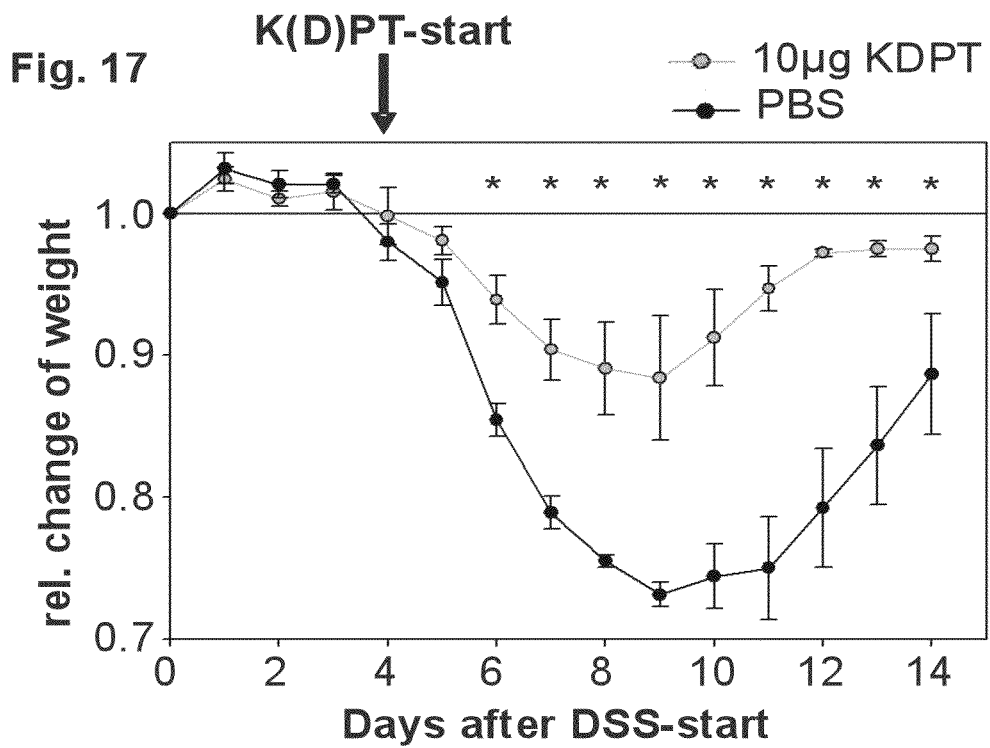
FIG. 17 shows the effect of K(D)PT in the therapeutic treatment of DSS-Colitis.

As shown in FIG. 17, K(D)PT was shown to be effective in therapeutic treatment of DSS-colitis. Colitis was induced by DSS application on day 0. On day 4 of DSS feeding all animals showed clinical signs of colitis including weight loss. In the following days weight loss was significantly more pronounced in PBS-treated mice, reaching a maximum on day 9, with 26.9%±1.1% vs. 11.6%±4.4% in K(D)PT treated mice. On day 12 after DSS-start K(D)PT-treated animals had regained 97.2%±0.26% of initial weight, PBS-treated animals only 79.3%±4.2%. Mucosal expression of IL-1βmRNA in K(D)PT-treated animals was 65% lower (4.14±1.2 fold induction) than in PBS-treated mice (11.2±1.7 fold induction (p<0.01)).

Figure 18:
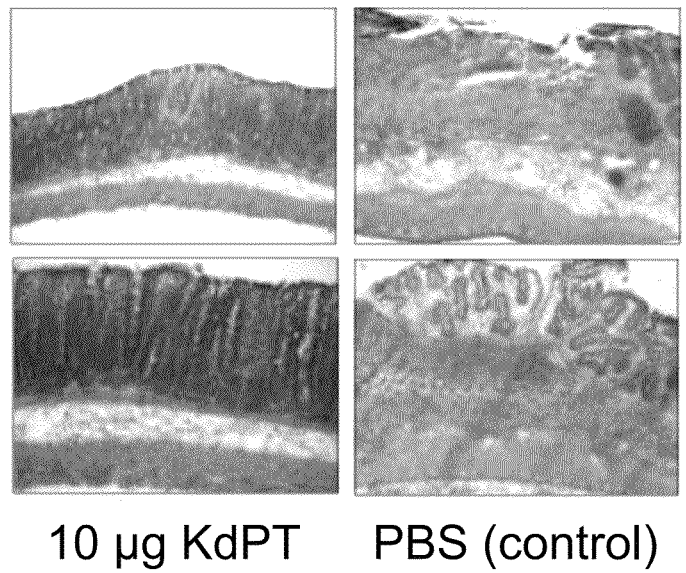
FIG. 18 shows significant reduction of histological signs of inflammation by K(D)PT.

As shown in FIG. 18, significant reduction of histological signs of inflammation by K(D)PT was observed. Histological analysis of colonic tissue revealed reduced inflammation in K(D)PT treated mice. K(D)PT-treated animals showed fewer ulcerations, less epithelial denudations, leukocyte infiltration and submucosal edema, as well as a significantly lower inflammatory score of 7.25±4.42, as compared to PBS treated (25.0±2.81 (p<0.001)).

Figure 19:
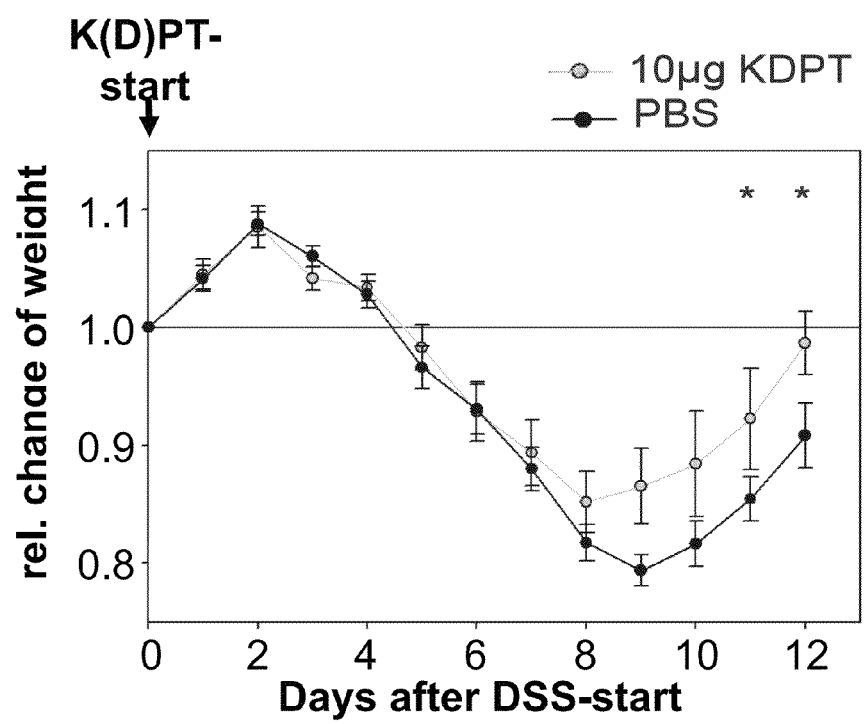
FIG. 19 shows significant therapeutic effects of rectally applied K(D)PT.

As shown in FIG. 19, significant therapeutic effects of rectally applied K(D)PT was observed. Colitis was induced by DSS application on day 0. Treatment with K(D)PT was started one day prior to DSS-treatment. Maximum weight loss in the K(D)PT-treated group was 14.8%±2.6 vs. 20.6%±3.6 in the PBS-treated group. K(D)PT-treated animals quickly regained weight and at the end of the observation period had a body weight of 98.7%±2.7 of the initial weight, while PBS-treated animals reached only 90.8%±2.8 (p<0.02) of initial weight.

Figure 20:
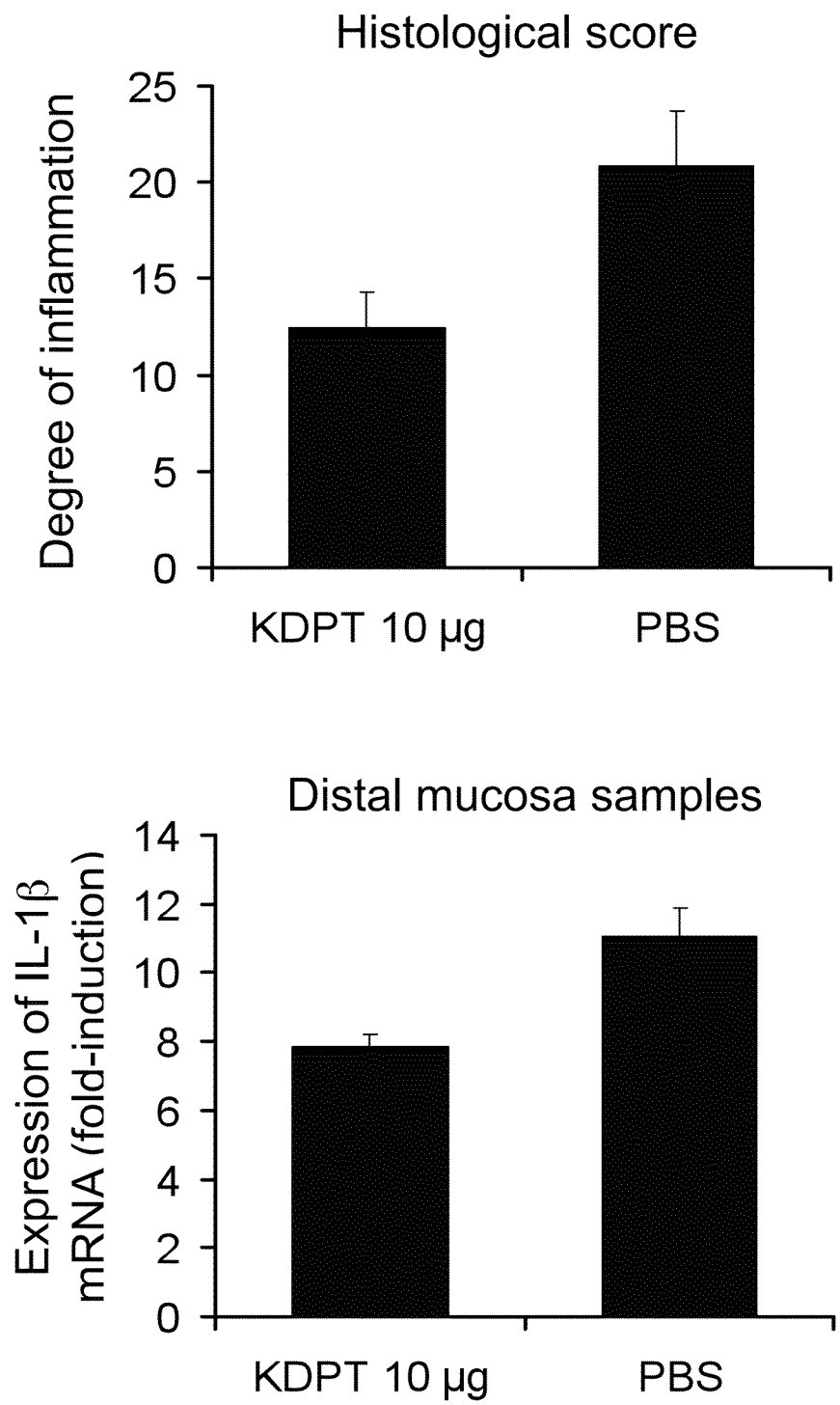
FIG. 20 significant reduction of histological score and mucosal IL-1β expression in K(D)PT-treated animals.

As shown in FIG. 20, significant reduction of histological score and mucosal IL-1β expression in K(D)PT-treated animals was observed. Histological evaluation of the distal colon third showed an inflammatory score of 12.4±1.83 for K(D)PT-treated animals and of 20.4±2.93 for PBS-treated animals (p<0.04). Mucosal expression of IL-1βmRNA in the distal third of the colon of K(D)PT-treated animals was reduced significantly (p<0.002).

Figure 21:
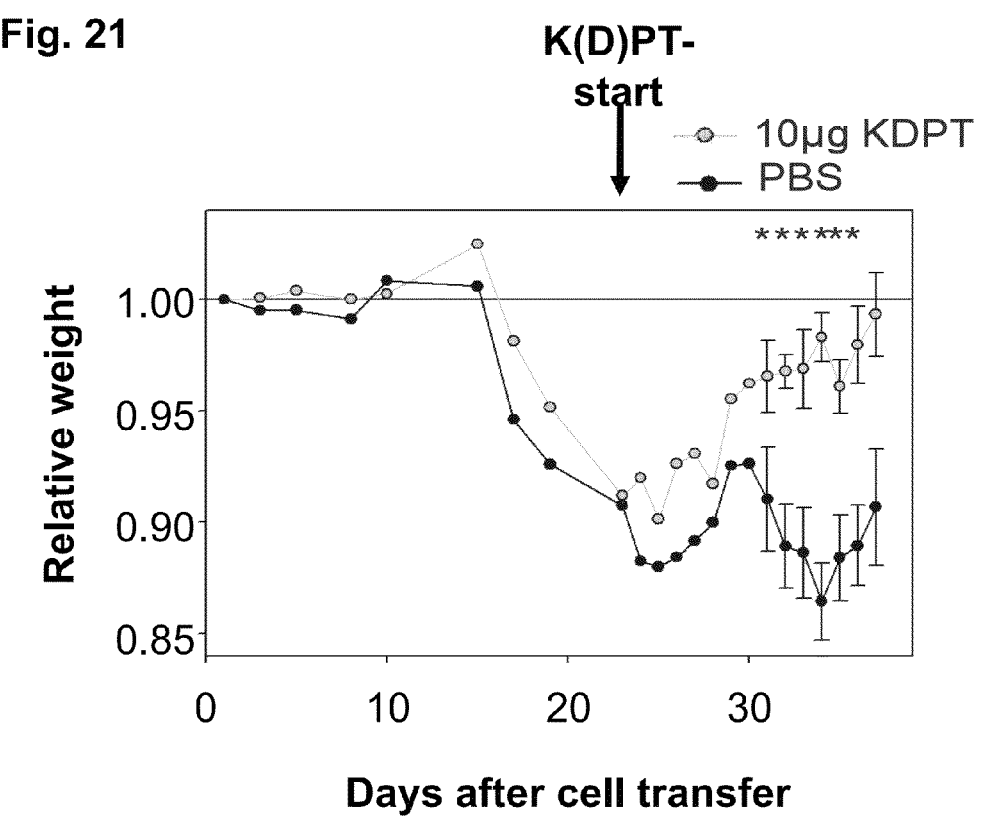
FIG. 21 shows that clinical signs of CD45RBhigh-transfer colitis are significantly reduced by K(D)PT-treatment.

As shown in FIG. 21, clinical signs of CD45RBhigh-transfer colitis are significantly reduced by K(D)PT-treatment. In the CD45RBhigh-transfer colitis model K(D)PT-treated animals recovered significantly faster and gained weight almost immediately after start of treatment (on day 23 after cell transfer), while PBS-treated animals further lost weight. From day 31 after cell transfer until the end of the observation period the K(D)PT group showed significantly higher weight (p<0.05). At the end of the experiment K(D)PT-treated animals had regained 99.3%±1.9 of their initial body weight, PBS-treated animals only 90.7%±2.6. Histological analysis confirmed these result, showing significantly higher inflammatory activity in control group animals.

EXAMPLE 10

IL-10 Deficient Colitis

Interleukin (IL)-10-/- mice spontaneously develop intestinal inflammation characterized by discontinuous transmural lesions affecting the small and large intestine and by dysregulated production of proinflammatory cytokines. (Rennick, Donna M., and Madeline M. Fort. Lessons From Genetically Engineered Animal Models. XII. IL-10-deficient (IL-102/2) mice and intestinal inflammation. Am JPhysiol Gastrointest Liver Physiol 278: G829-G833, 2000. See also Rennick, Donna M., Madeline M. Fort and Natalie L\J. Davidson. Studies with IL-10-/- mice: an overview J of Leukocyte Biology, Vol. 61, 389-396: 1997; both references of which are herein incorporated by reference in their entireties.)

The uncontrolled generation of IFN-γ-producing CD41 T cells (Th1 type) has been shown to play a causal role in the development of enterocolitis affecting these mutants. These genetically engineered mutants exhibit distinct pathological changes and cytokine profiles that have been associated with either Crohn's disease (CD) or ulcerative colitis (UC) in humans. These experiments using animal models of animal models of inflammatory bowel disease (IBD), Crohn's disease (CD) or ulcerative colitis (UC) demonstrate the efficacy of the inflammatory compounds of the present invention in the treatment of Inflammatory bowel disease, Crohn's disease, and ulcerative colitis.

Inflammatory bowel disease (IBD) describes two distinct idiopathic inflammatory disorders of the intestine, ulcerative colitis and Crohn's disease. Ulcerative colitis is characterized by periods of active and inactive disease, a pattern observed in 80-90% of patients with this disease. Crohn's disease is also typified by repetitive cycles of active and quiescent disease with clinical patterns that vary according to disease location and clinical manifestations (inflammatory, fibrostenotic, and fistulizing). The primary goal of treatment is to induce and maintain remission in a safe and efficacious fashion. Currently the armamentarium of agents used to treat IBD includes derivatives of 5-aminosalicylic acid (5-ASA), corticosteroids, immune modulators such as azathioprine (AZA) or 6-mercaptopurine (6-MP) and methotrexate, cyclosporine (CyA), antitumor necrosis factor (TNF) antibodies such as infliximab, adalimumab or certolizumab pegol, and monoclonal antibodies against the cellular adhesion molecule α4-integrin like natalizumab. The instant specification demonstrates that upon administration of KdPT in the IL-10 deficient mice (FIG. 22), weight loss and inflammation were significantly reduced in KdPT treated animals.

Animals

Homologous IL-10 gene-deficient mice were purchased from Jackson Laboratories (strain name: C3Bir.129P2(B6)-I110tm1Cgn/Lt; Bar Harbor, Me., USA). Experiments described here were performed with 8-9 weeks old female mice. All animals were kept under pathogen-free conditions at 24° C. with a controlled 12 h day-night cycle and had free access to standard diet and drinking water. The animal studies were approved by the local animal subjects committee, University of Münster.

Induction of Colitis in IL-10-/- Mice

The targeted disruption of the IL-10 gene in mice leads to spontaneous development of a chronic enterocolitis. In order to aggravate the developing colitis piroxicam was given from day 1 until day 7 and from day 15 until 22 at a dose of 60 mg/250 g of food and 80 mg/250 g, respectively. Piroxicam was mixed with rodent-chow. PBS-diluted KdPT was given daily by oral administration beginning from day 0 before start of piroxicam administration until the end of the experiment. Control mice received PBS only. Disease activity was monitored daily by body weight measurement. At the end of experiment mice were sacrificed and the colons removed. Colons were opened, embedded in O.C.T. and kept frozen at -80° C. until further use. Sections (5 μm) were stained with H&E and analysed by two blinded investigators.

KdPT Attenuates Colitis in NSAID-treated IL-10-deficient Mice

IL-10-deficient mice are known to develop a spontaneous colitis that can be aggravated by oral administration of a non-steroidal drug such as piroxicam (see supra). Accordingly, IL-10-deficient mice received an effective oral dose of KdPT (100 μg daily) beginning from day 0 after administration of piroxicam until the end of the experiment on day 31 while control animals received PBS. Immediately after starting the first piroxicam treatment all placebo-treated animals showed a progressive weight loss up to 19.9±3.8% on day 27. However, the KdPT-treated group exhibited a significantly less pronounced loss of body weight of 8.4±2.9% (p<0.05) on day 27 confirming the protective effect of KdPT regarding intestinal inflammation.

Histologic examination on day 31 after starting KdPT application revealed less severe inflammation with reduced involvement of the submucosa and a lower number of crypt abscesses in KdPT-treated animals than in controls. Histological scoring according to Berg et al confirmed a significantly higher score in control mice (13.6±3.2) vs. KdPT-treated animals (4.8±1.5; p<0.01).

FIG. 22 shows the effect of KdPT on colitis in IL-10 deficient mice. 8-9 week old IL-10 deficient mice were fed with chow containing Piroxicam (day 1 to 7, 60 mg/250 g chow and day 15 to 22, 80 mg/250 g chow), in order to amplify the spontaneous enterocolitis observed in these animals. PBS or KdPT in PBS (100 μg/animal/day, p.o.), respectively, were given from day 0 until the end of the experiment. Disease activity was observed by daily weighing; at the end of the experiment the colon was explanted and subjected to histological evaluation (scale according to Berg et al.). Weight loss and inflammation were significantly reduced in KdPT treated animals.

EXAMPLE 11

Effect of KdPT on Imiquimod-induced Psoriasis-like Disease in Mice

Figure 23:
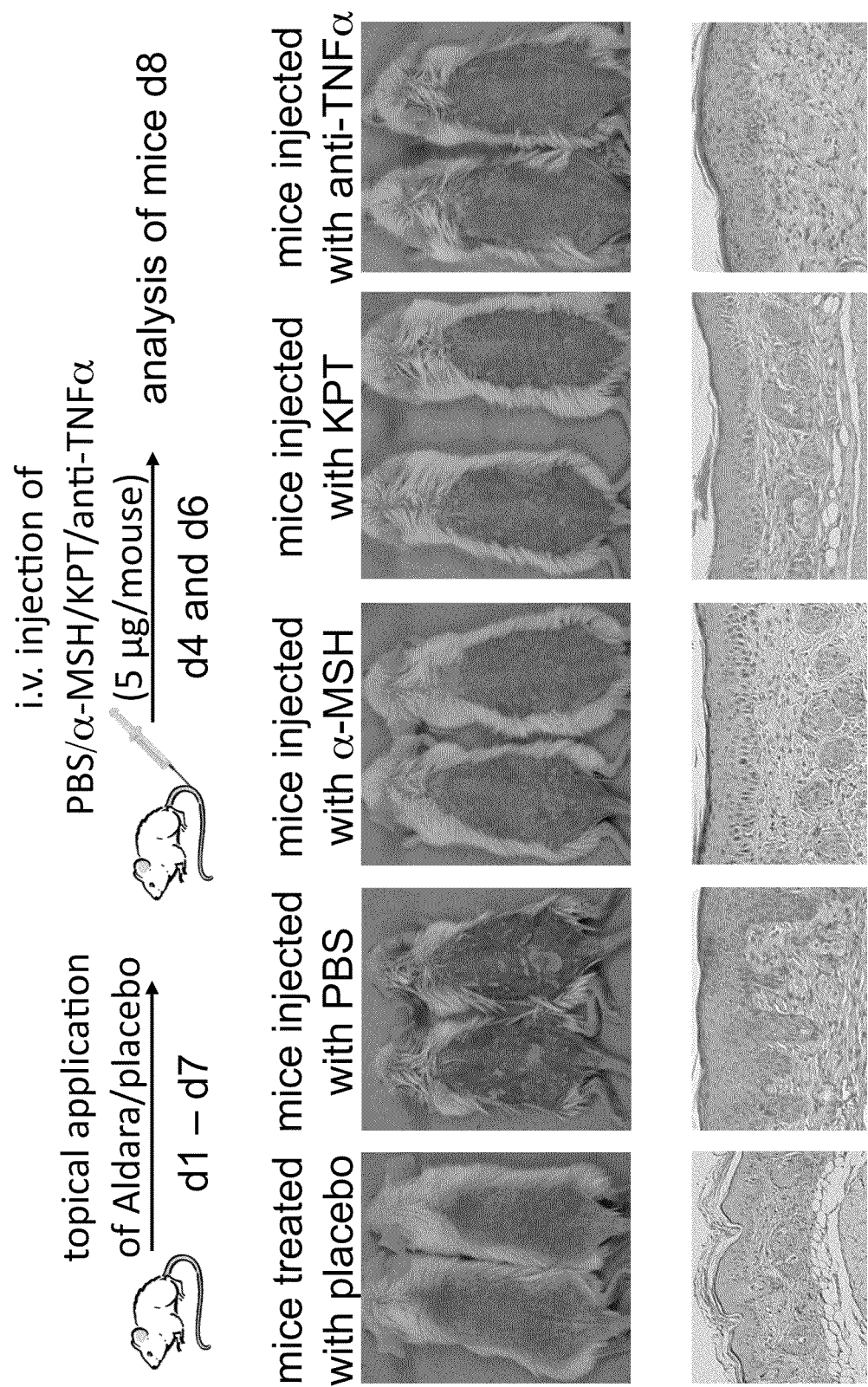
FIG. 23 shows the effect of KdPT on Imiquimod-induced Psoriasis-like disease in mice.

The experiment was conducted as indicated in FIG. 23 and clearly reduced skin reddening and—scaling are visible as well as a histologically clearly reduced epidermal thickness. KdPT is roughly equipotent to an anti-TNFα-antibody.

EXAMPLE 12

Effect of KdPT on Psoriasis in a Transplant Model

Figure 24:
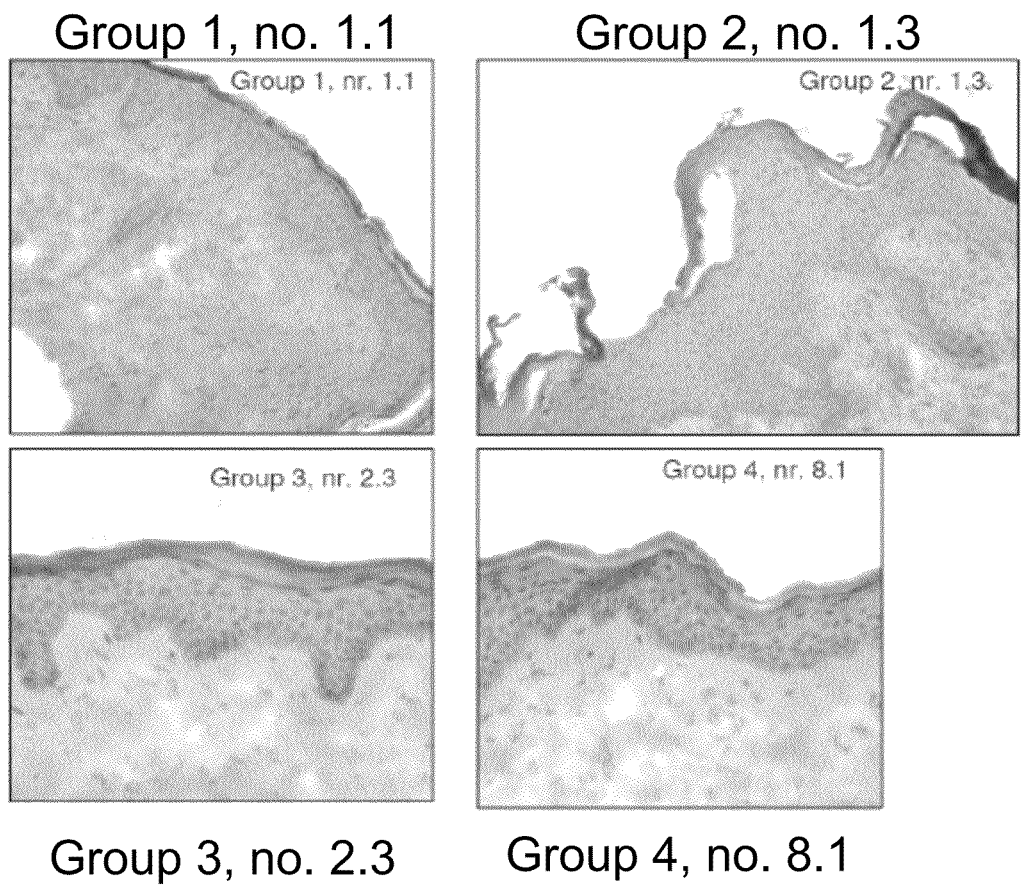
FIG. 24 shows the effect of KdPT on Psoriasis in a transplant model.
Figure 25:
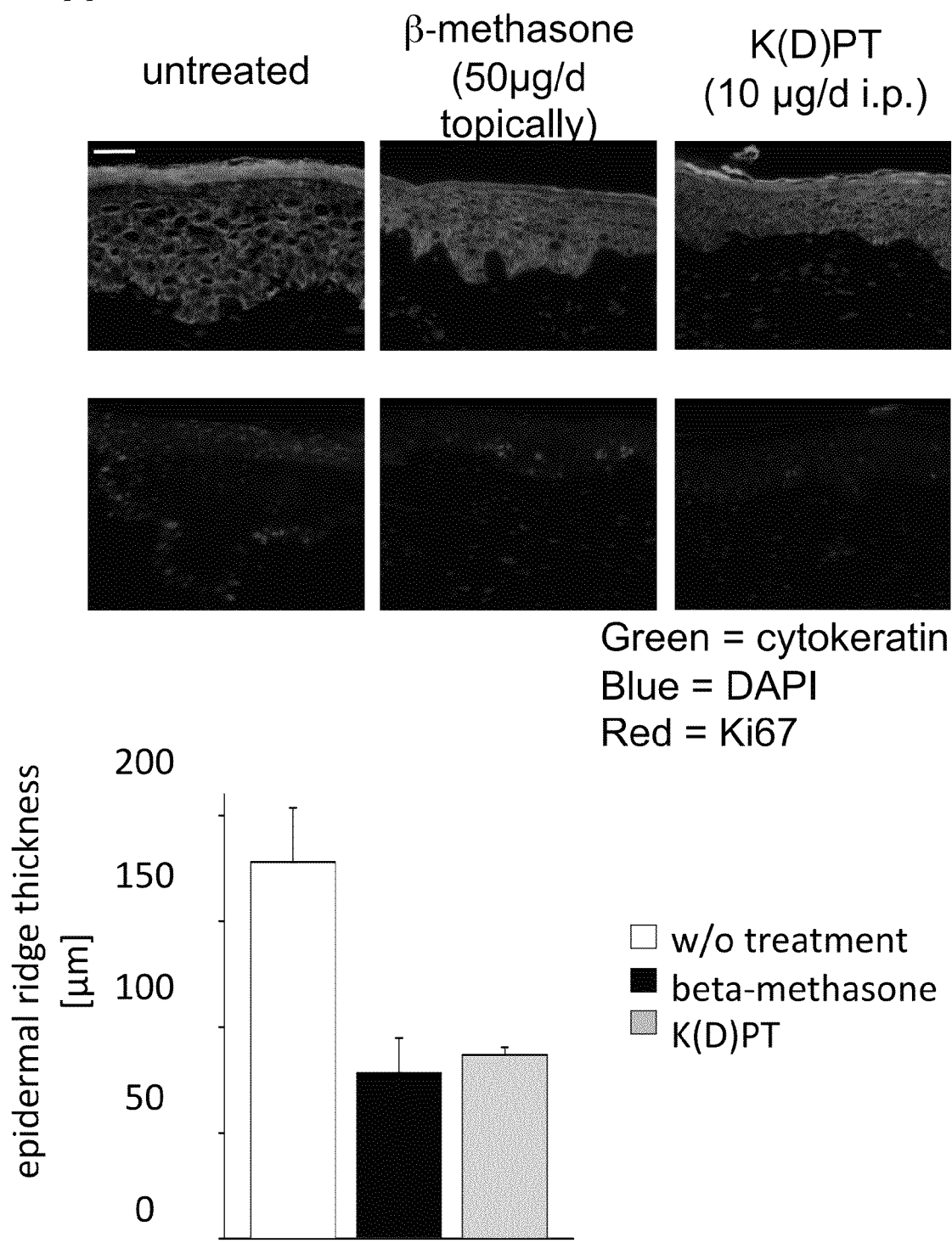
FIG. 25 further illustrates the effect of KdPT on Psoriasis in a transplant model.
Figure 25:
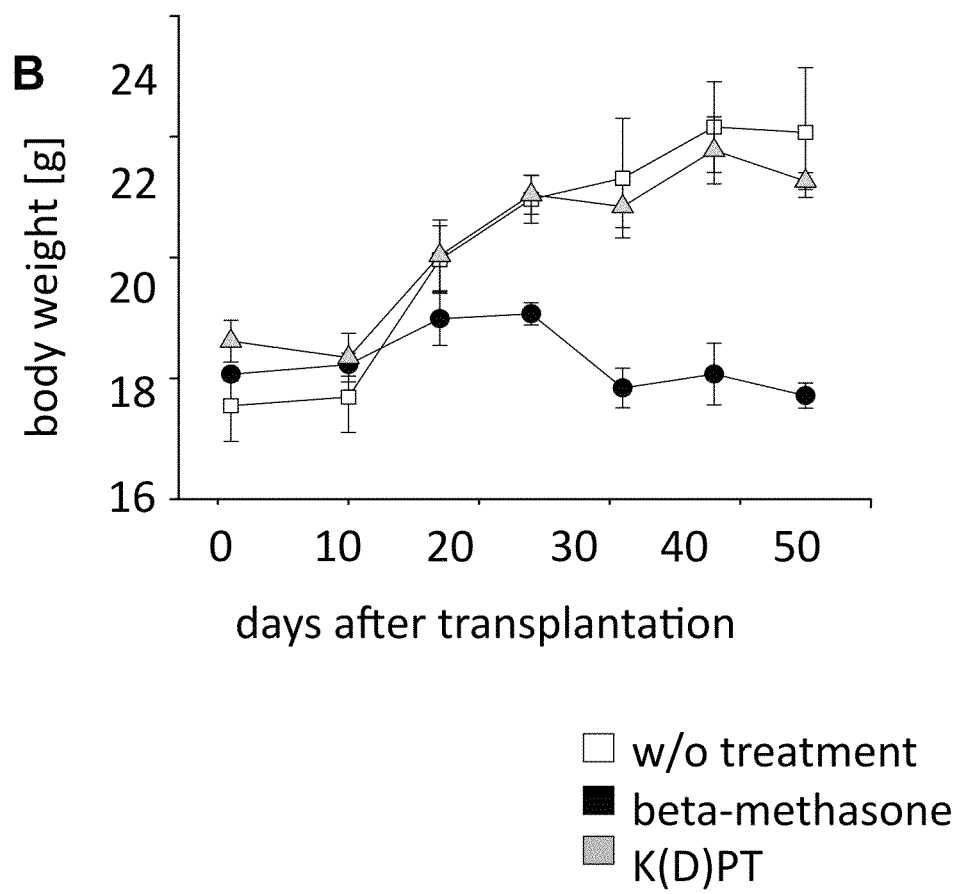

Immunodeficient mice (BNX mice) were transplanted with skin from psoriatic human donors. Animals with viable transplant were injected with PBMCs from the same donor, resulting in appearance of a psoriatic phenotype within the transplant. Animals were treated as follows:
Group 1: Betamethasone, topically, 2× daily, Group 2: Vehicle, i.p. 100 μL/d, Group 3: KdPT i.p. 1 μg/d, Group 4: KdPT i.p. 10 μg/d, all treatments were kept up for three weeks. As shown in FIG. 24:
A) Clear reduction of epidermal thickness by KdPT.
B) Significant reduction of Ki67-expression by KdPT As shown in FIG. 25, immunodeficient mice (BNX mice) were transplanted with skin from psoriatic donors. Animals with viable transplant were injected with PBMCs from the same donor, resulting in appearance of a psoriatic phenotype within the transplant. Animals were treated as follows:
Group 1: Vehicle, i.p. 100 μL/d, Group 2: Betamethasone, topically, 2× daily, Group 3: KdPT i.p. 10 μg/d, all treatments were kept up for three weeks.
A) Clear reduction of epidermal thickness and Ki67-expression by KdPT.
B) Treatment with KdPT does not result in weight loss as compared to treatment with betamethasone.

EXAMPLE 13

Effect of KdPT on the Number of Regulatory CD4+CD25+ Foxp3+-T-cells (as Measured by Flow Cytometry, A), as Well as on the Expression of IL-10, IFNγ and TNFα (qRT-PCR, B)

Figure 26:
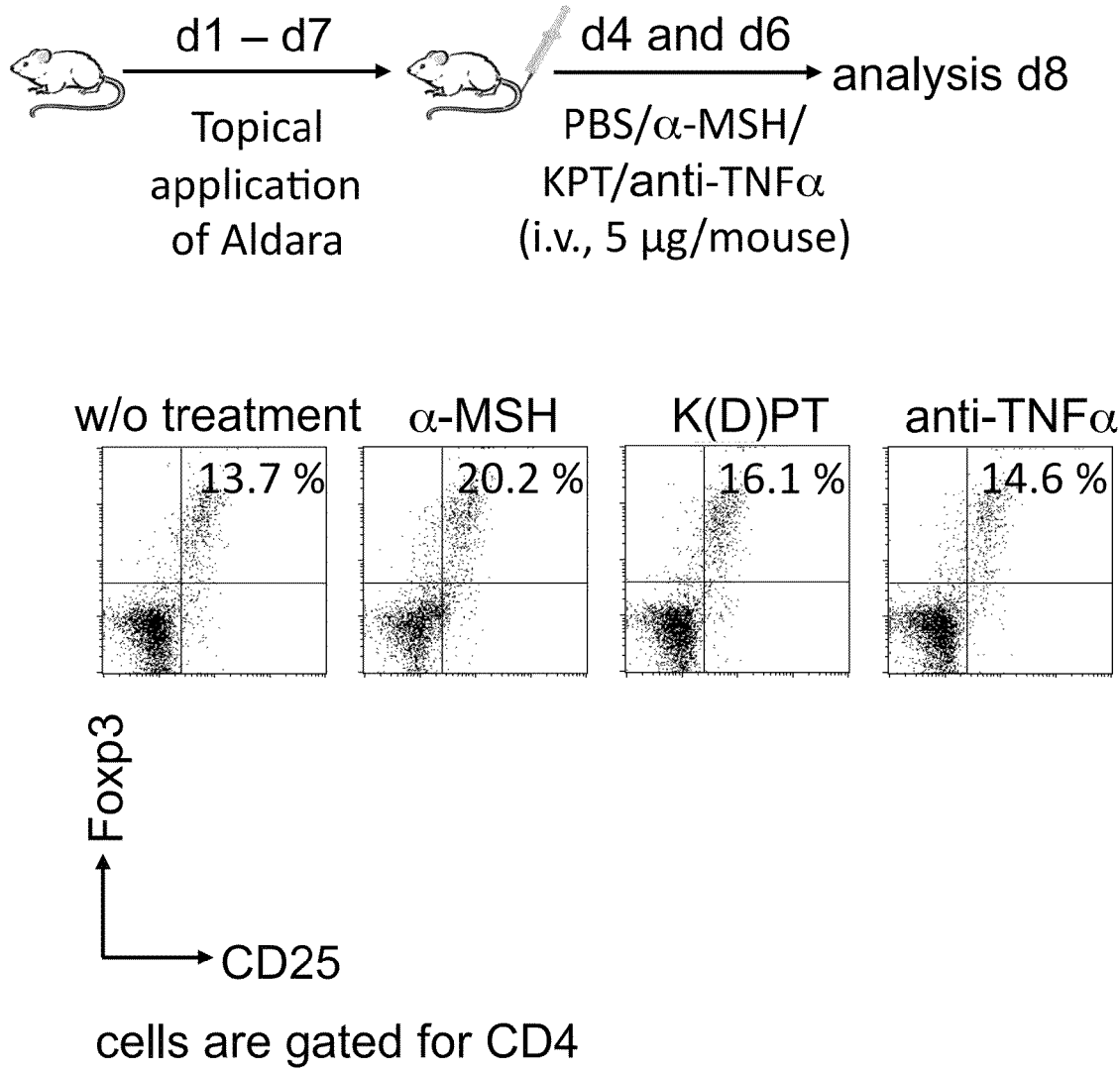
FIG. 26 shows the effect of Effect of KdPT on the number of regulatory CD4+CD25+Foxp3+-T-cells (as measured by flow cytometry, A), as well as on the expression of Foxp3, IL-10, IFNγ and TNFα (qRT-PCR, B).
Figure 26:
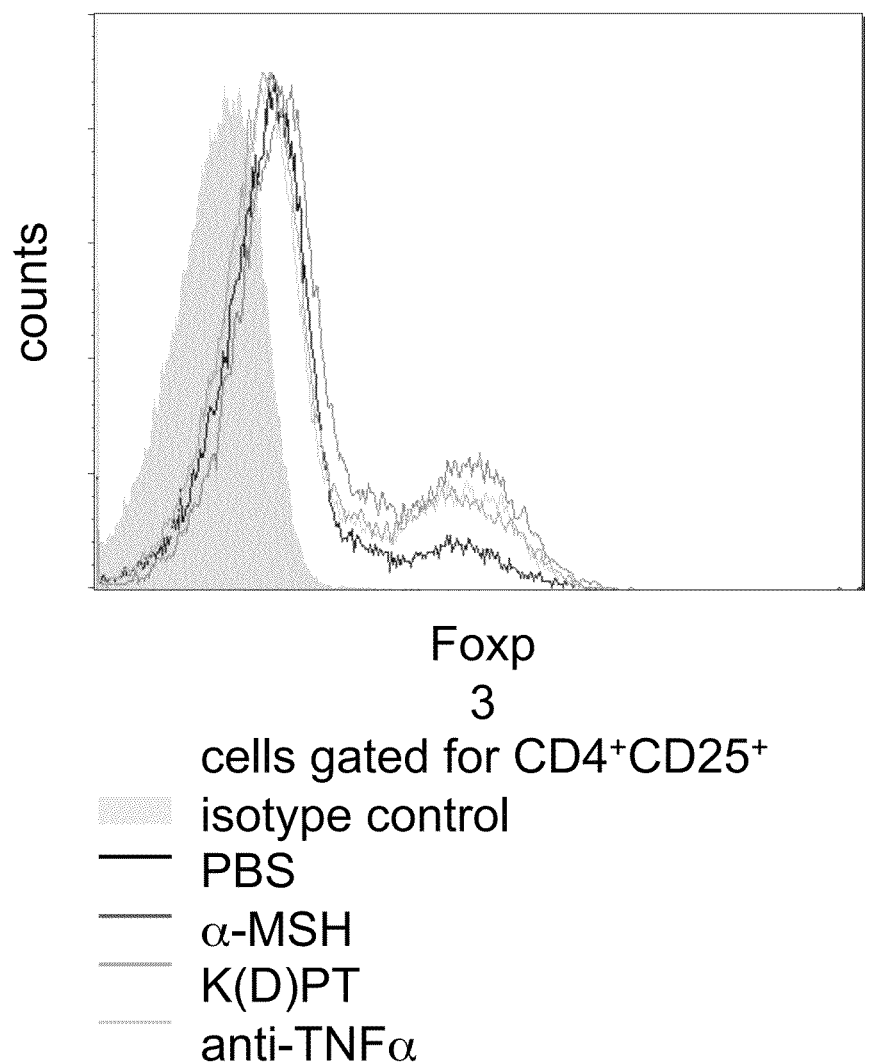
Figure 26:
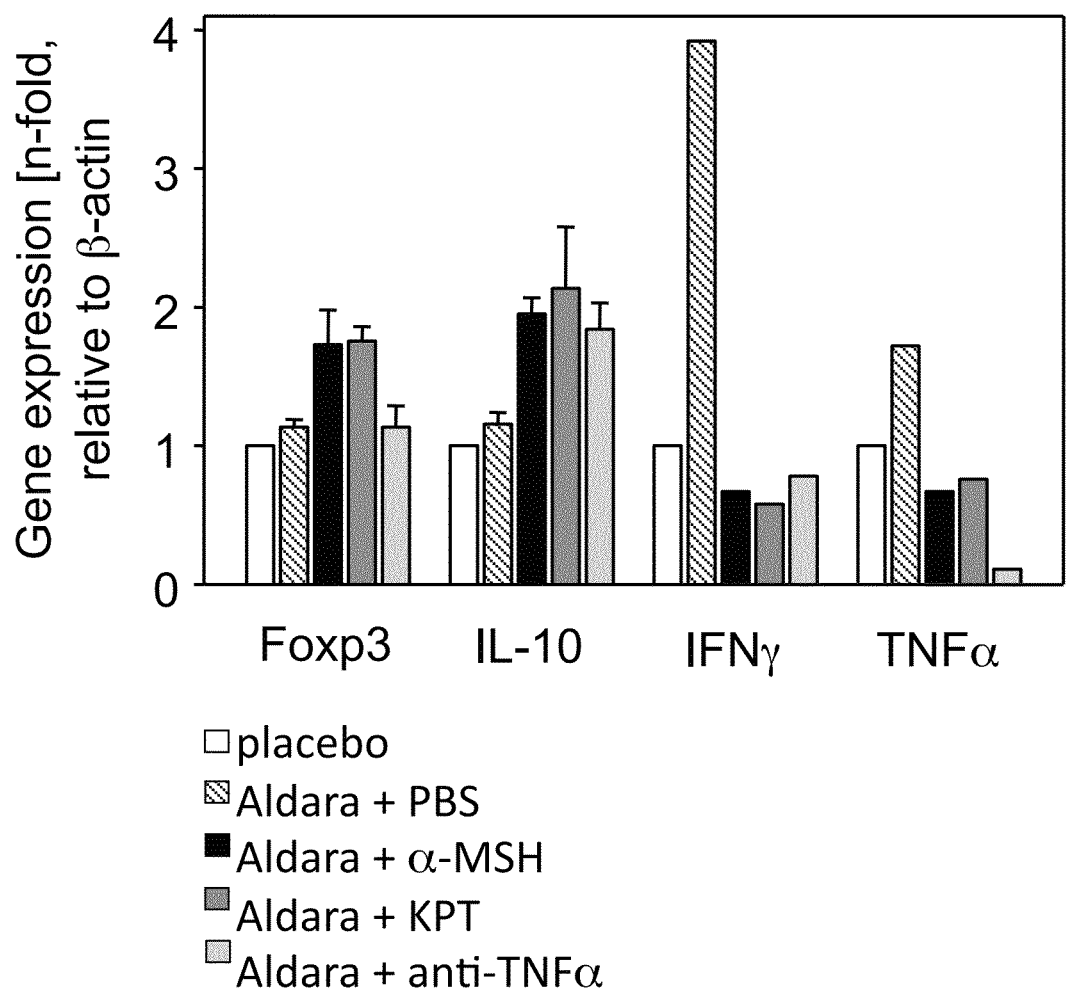

FIG. 26 (*a*) shows increased numbers of regulatory T cells in mice treated with α-MSH or K(D)PT after Imiquimod-induced psoriasis-like skin inflammation. FIG. 26 (*b*) shows increased expression of regulatory T cells markers in mice treated with α-MSH or K(D)PT after Imiquimod-induced psoriasis-like skin inflammation.

EXAMPLE 14

Effect of KdPT on CD4+CD25+Foxp3+-Treg in Blood of Psoriasis Patients.

Figure 27:
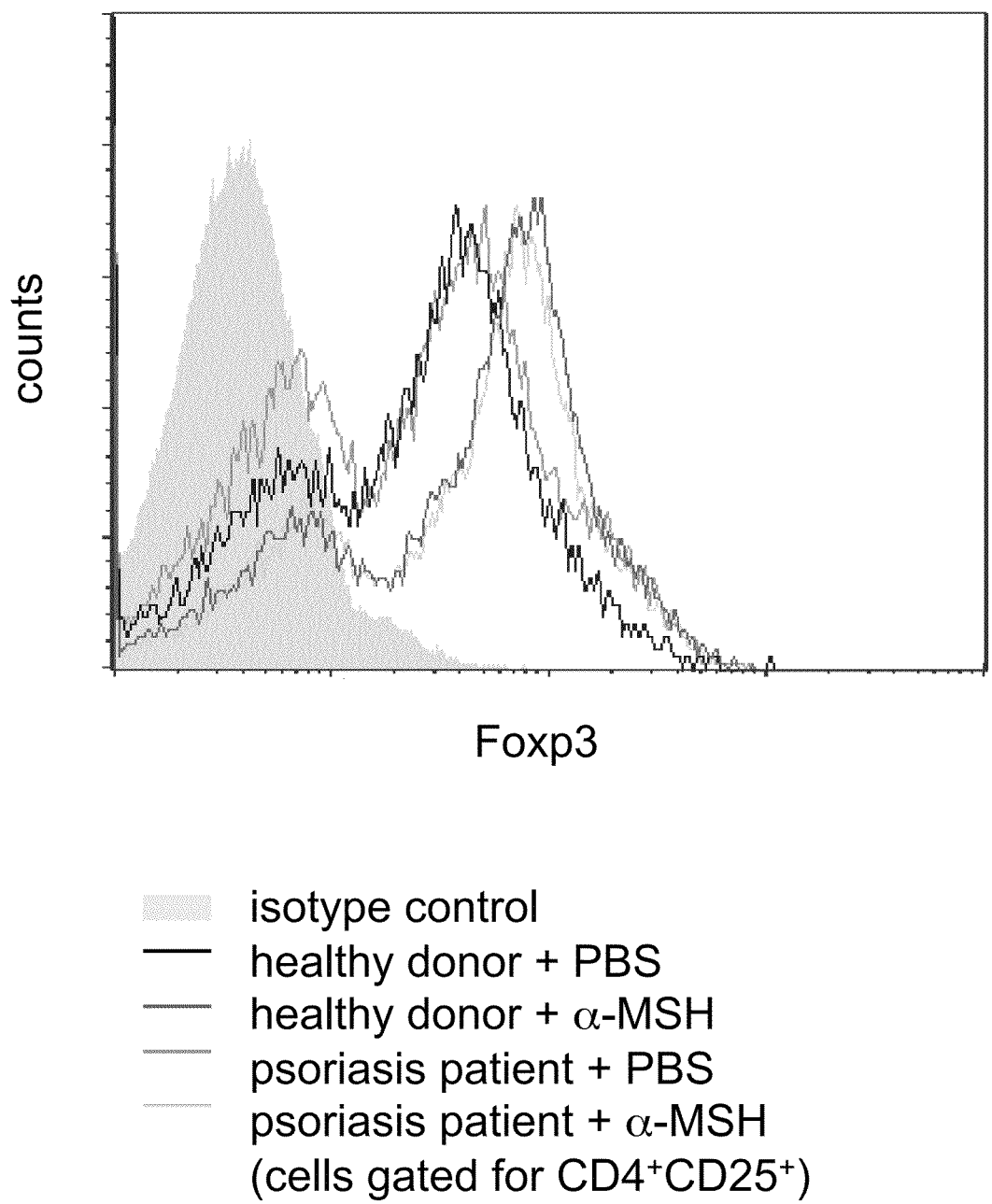
FIG. 27 shows the effect of KdPT on CD4+CD25+ Foxp3+-Treg in blood of psoriasis patients.
Figure 27:
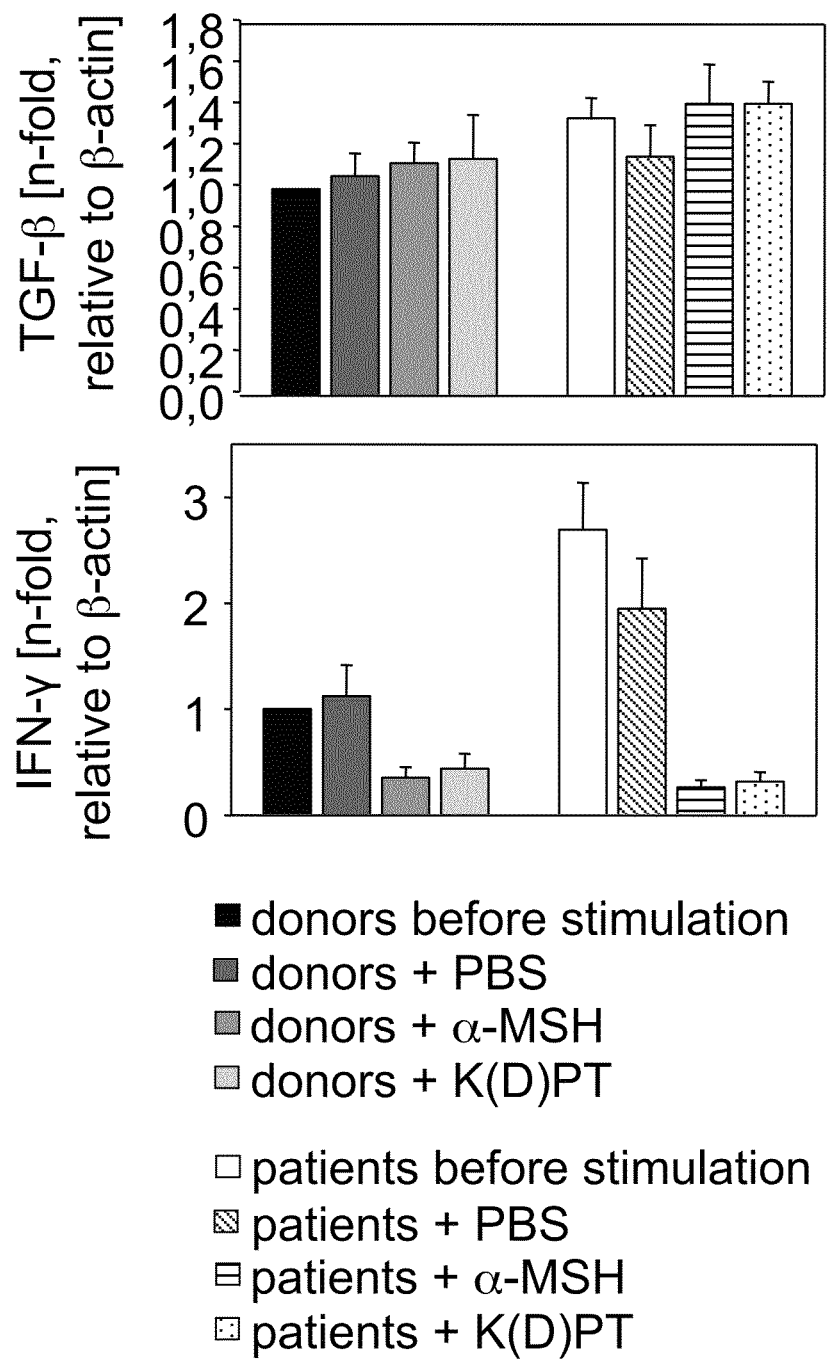

Clearly elevated numbers of CD4+CD25+Foxp3+ T-cells (A) and clearly higher expression of IL-10 as well as concomitant reduction of IFNγ expression (B). FIG. 27 (A) shows the effects of α-MSH and K(D)PT on the number of regulatory T cells from psoriasis patients. FIG. 27 (B) shows the effects of α-MSH and K(D)PT on regulatory T cells from psoriasis patients. While the expression of Foxp3 and IL-10 are upregulated the expression of IFN-γ is down-regulated substantially.

EXAMPLE 15

Suppressive Effect of CD4+CD25+Foxp3+ T-Cells after Treatment with K(D)PT.

Figure 28:
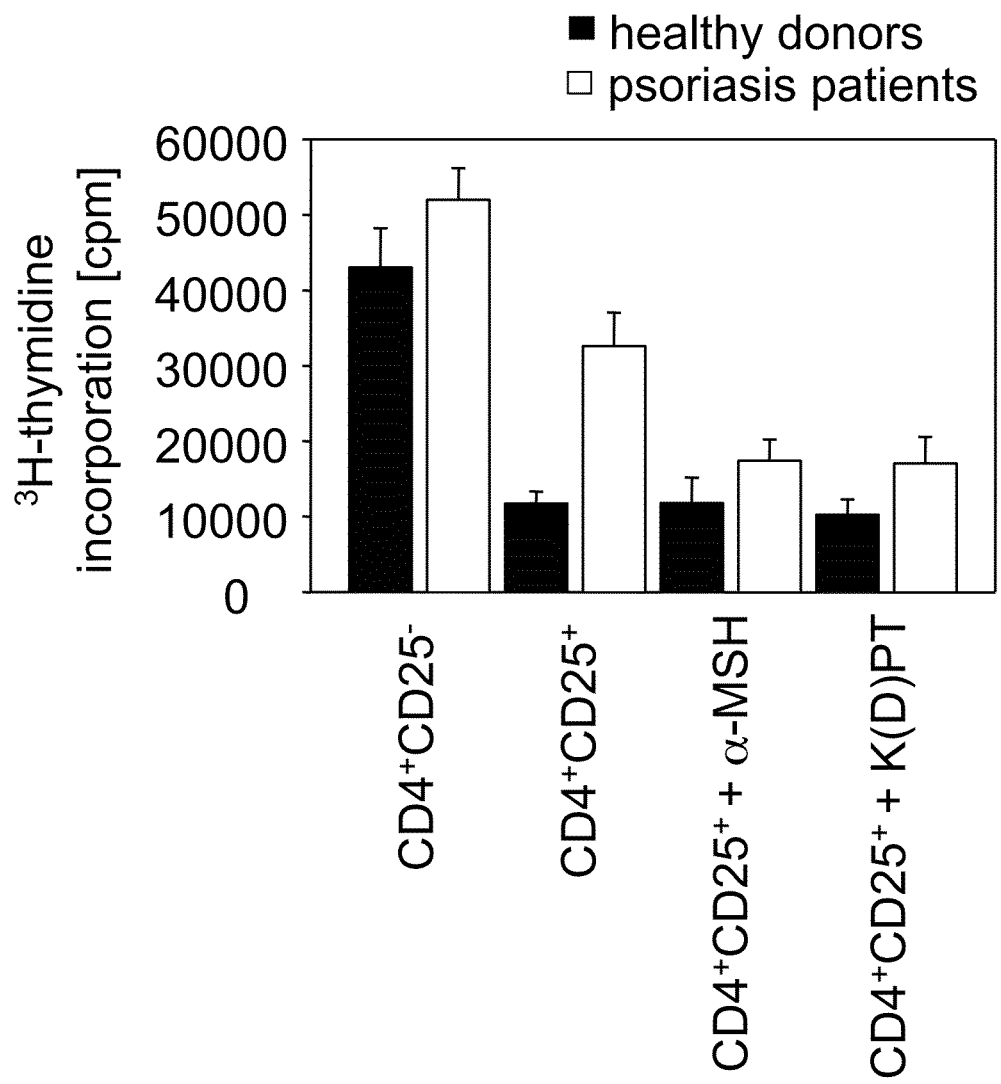
FIG. 28 shows the suppressive effect of CD4+CD25+ Foxp3+ T-cells after treatment with K(D)PT.
Figure 28:
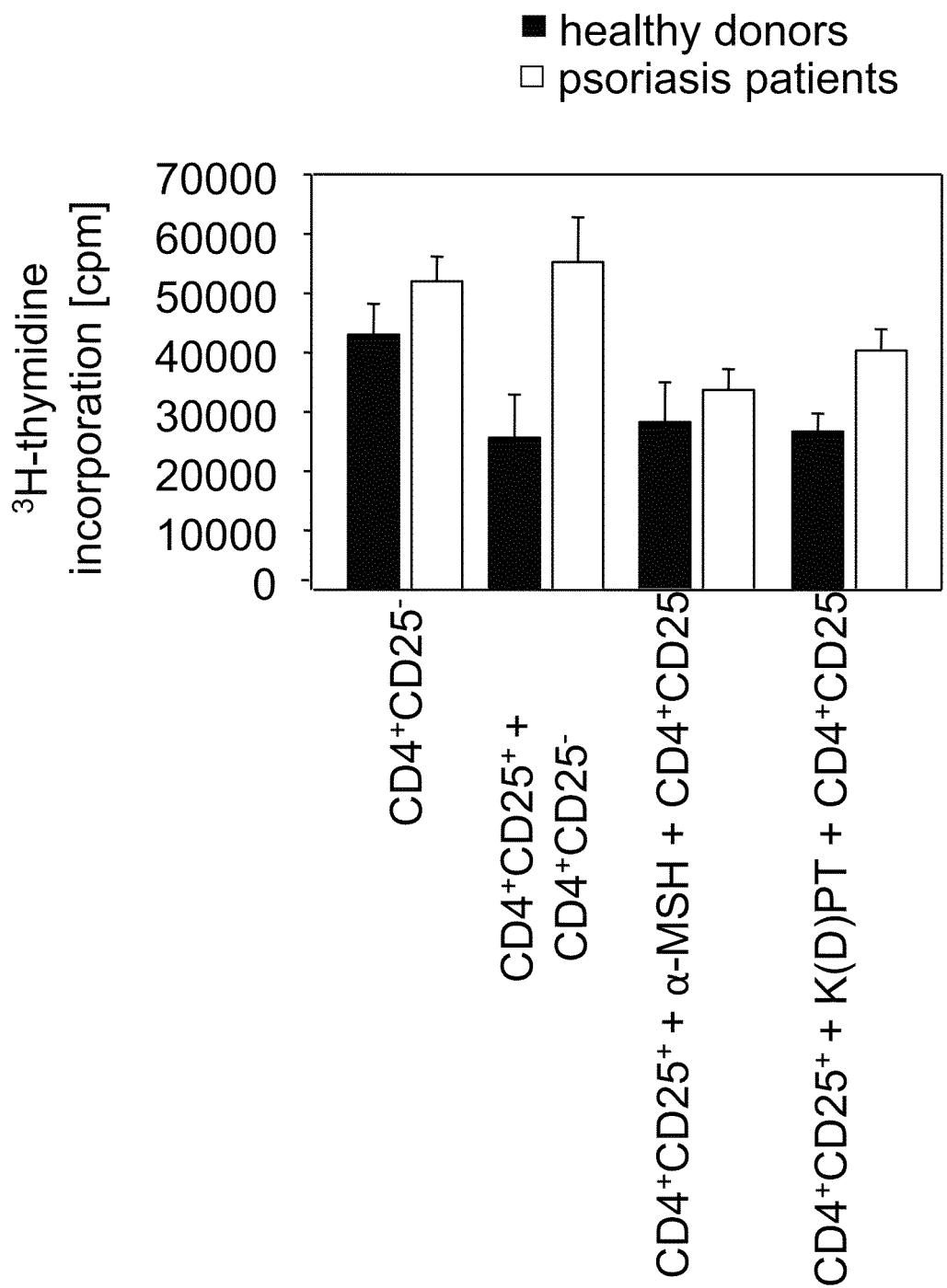

In FIG. 28, PBMC were isolated from peripheral blood of 3 healthy donors and 3 psoriasis patients and stimulated for 48 h with α-MSH or K(D)PT ($10^{-9}$ molar) Subsequently, CD4+ CD127-regulatory T cells were purified by magnetic cell separation and co-cultured at a 1:1 ratio with freshly isolated CD4+CD25 effector T cells from the same donor/patient.

EXAMPLE 16

Effect of KdPT on Th17-Zellen and Expression of Th17-typical Parameters

Figure 29:
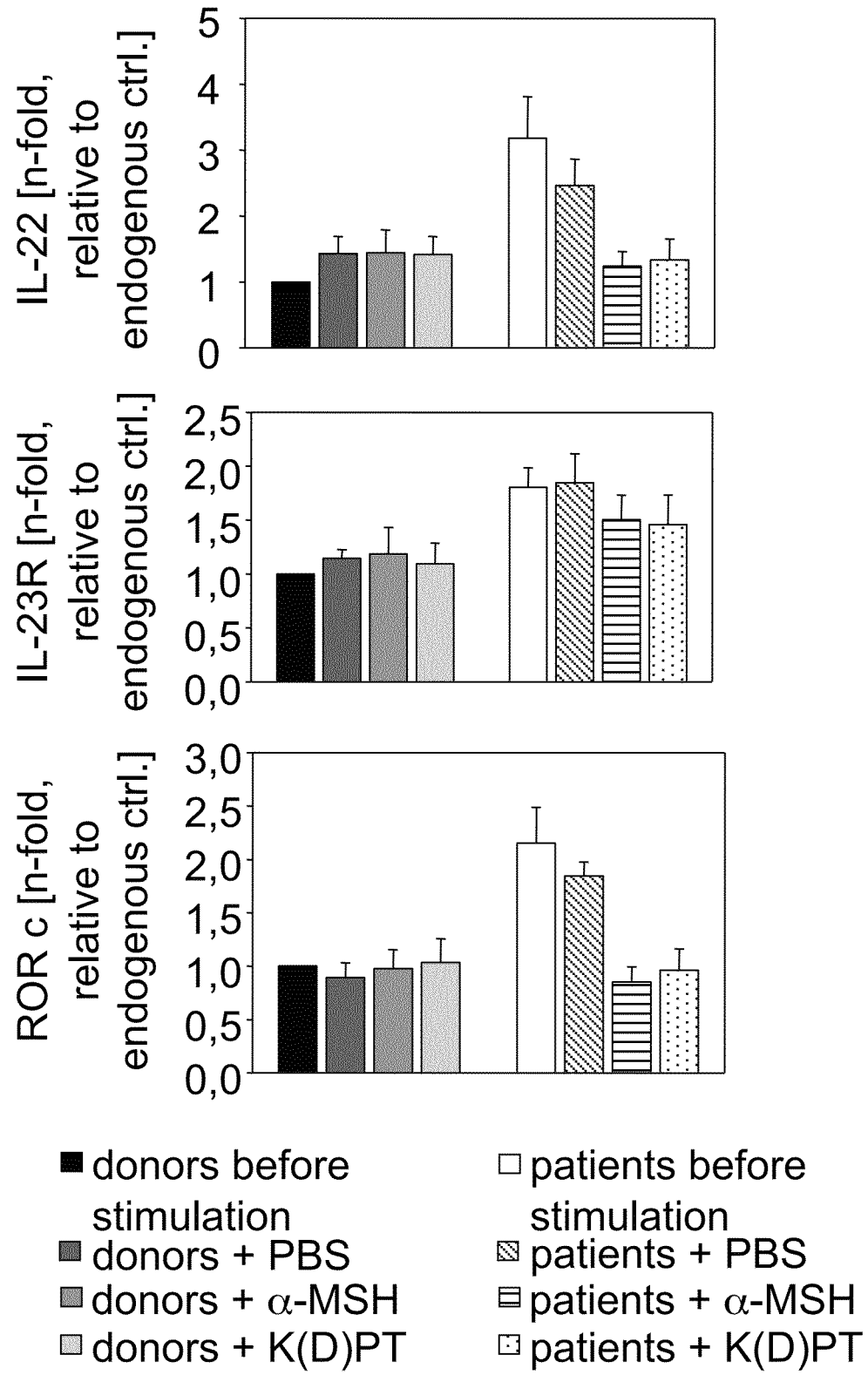
FIG. 29 shows the effect of KdPT on human Th17-cells and expression of Th17-typical parameters.

In FIG. 29, PMBC were isolated from peripheral blood of 8 healthy donors and 8 psoriasis patients and stimulated for 48 h with α-MSH or K(D)PT (10-9 molar). Subsequently, CD4+ T cells were purified by magnetic cell separation and subjected to RNA-isolation and reverse transcription. The expression of IL-17, IL-21, IL-22, IL-23R, as well as RORc was quantified by realtime-PCR. FIG. 29 (A) shows the effects of α-MSH and K(D)PT on Th-17 cells from psoriasis patients. FIG. 29 (B) shows the expression of Th-17 associated genes in CD4+ T cells from psoriasis patients and healthy donors after stimulation with α-MSH or K(D)PT.

EXAMPLE 17

Effect of KdPT on the Expression of Th17-typical Parameters

FIG. 30 (A) Results from quantitative RT-PCR for several Th17 markers; murine RORγt is equivalent to human RORc. Reduced Expression of Th17 markers in mice treated with α-MSH or K(D)PT after Imiquimod-induced psoriasis-like skin inflammation. FIG. 30 (B) Cytokine expression by post-experiment harvested and purified CD4+-T-cells points to suppression of Th17 phenotype while showing increased level for anti-inflammatory IL.-10.

EXAMPLE 18

Effect of KdPT on Dendritic Cells

Figure 31:
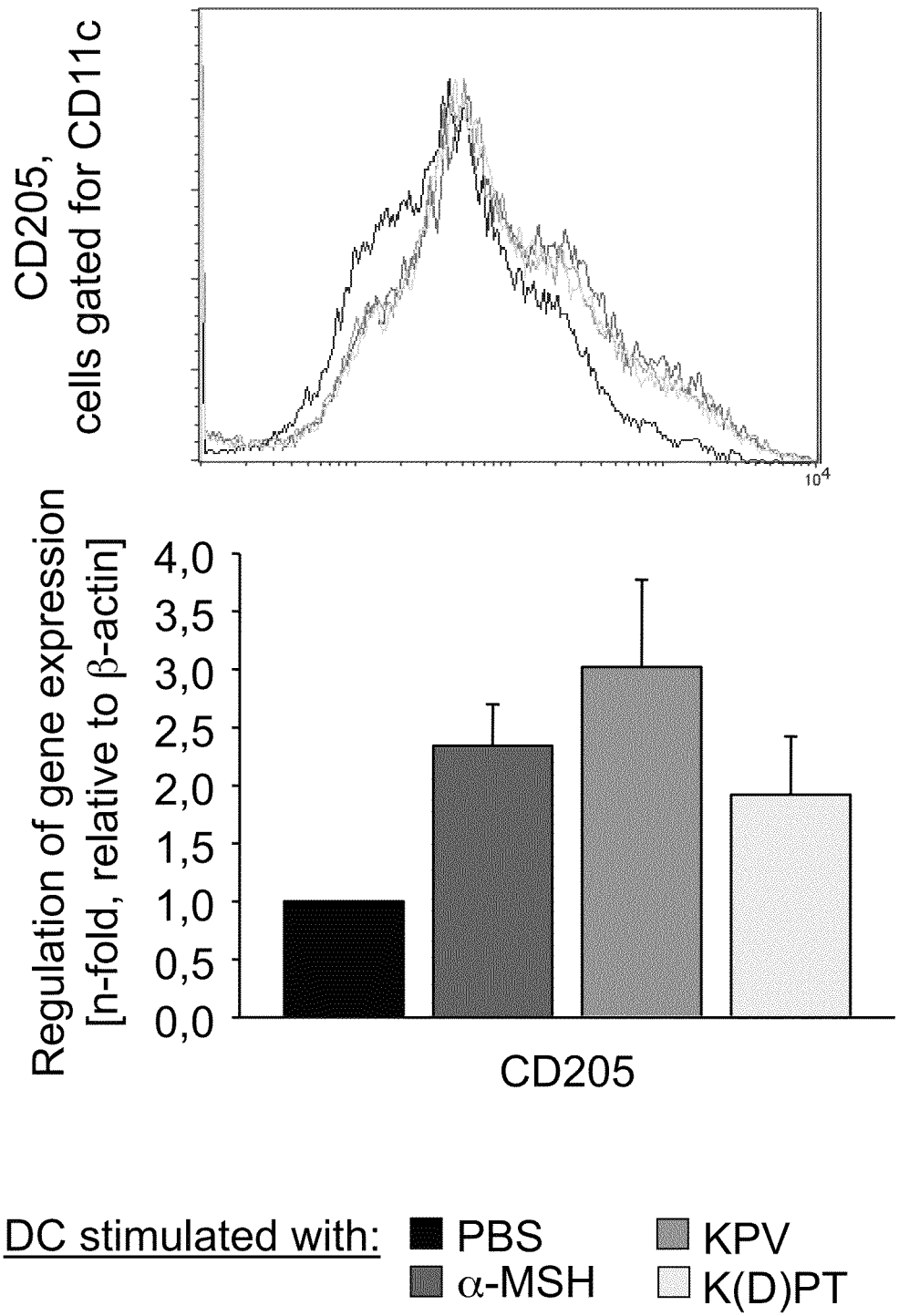
FIG. 31 shows the effect of KdPT on dendritic cells.

In FIG. 31, KdPT treated DC displayed elevated levels of parameters, which stand for a tolerizing dendritic cell phenotype. Among these are the cell surface protein CD205 as well as the cytokines IL-6 and IL-10. Expression of surface molecules involved in antigen presentation, namely CD80, CD86 and MHC class II, on the other hand is down-regulated.

EXAMPLE 19

Effect of KdPT-treated DC on CD4+-T-cells

Figure 32:
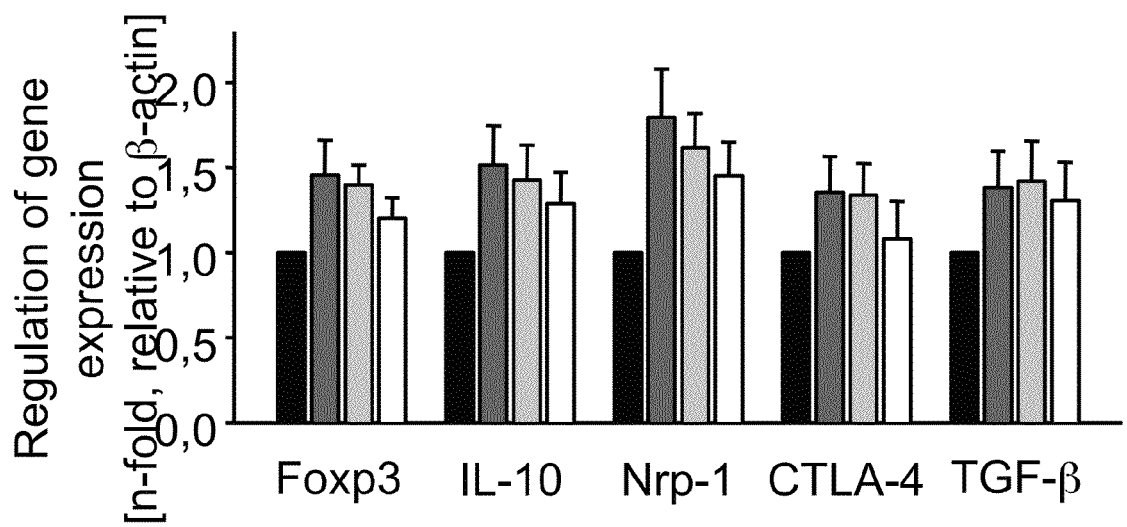
FIG. 32 shows the effect of KdPT-treated DC on CD4+-T-cells.

In FIG. 32, after treatment with KdPT-treated dendritic cells CD4+-T-cells show elevated levels of regulatory markers.

EXAMPLE 20

Figure 33:
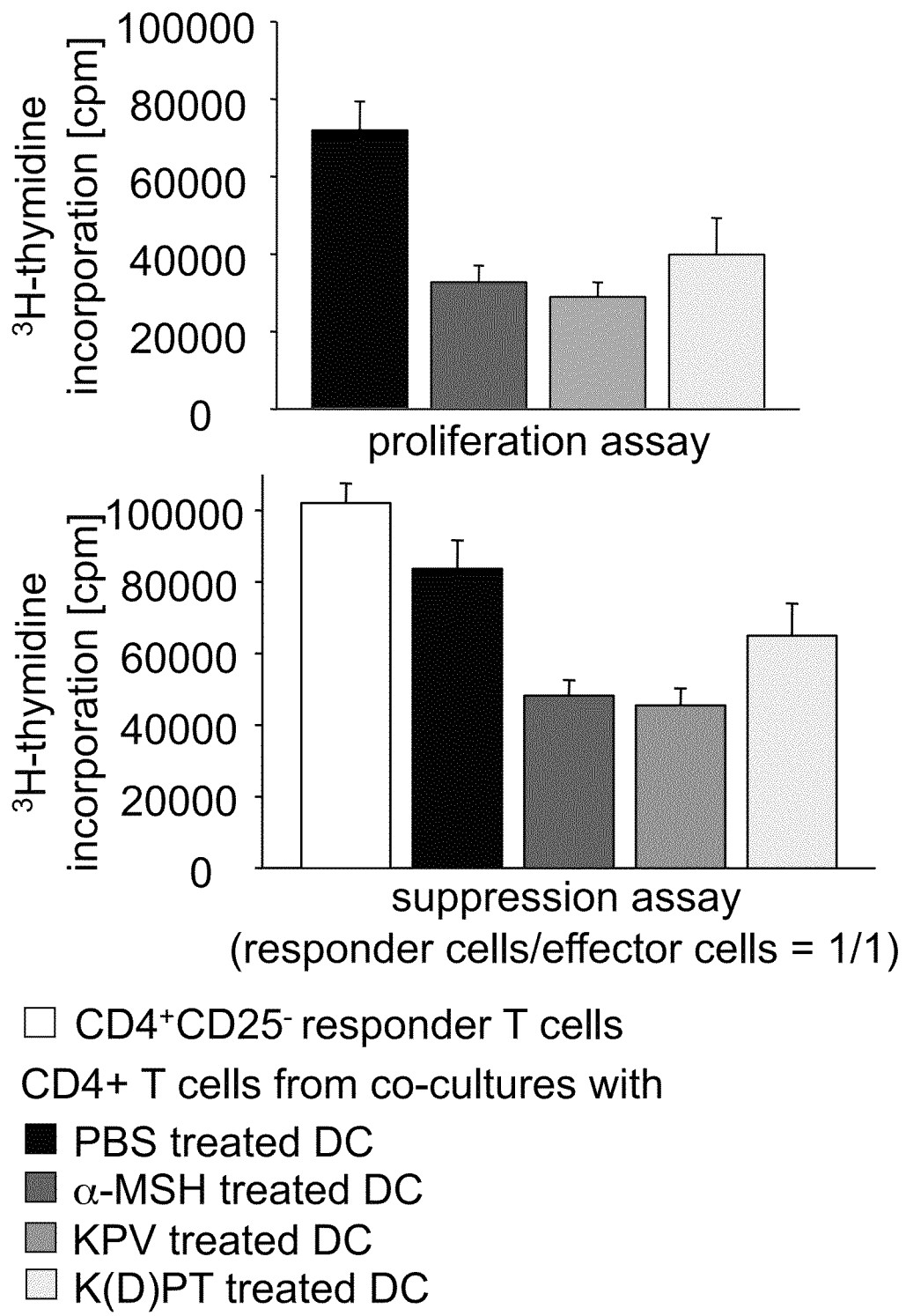
FIG. 33 shows that CD4+-T-cells display suppressive properties in vitro and in vivo after treatment with KdPT-treated DC.
Figure 33:
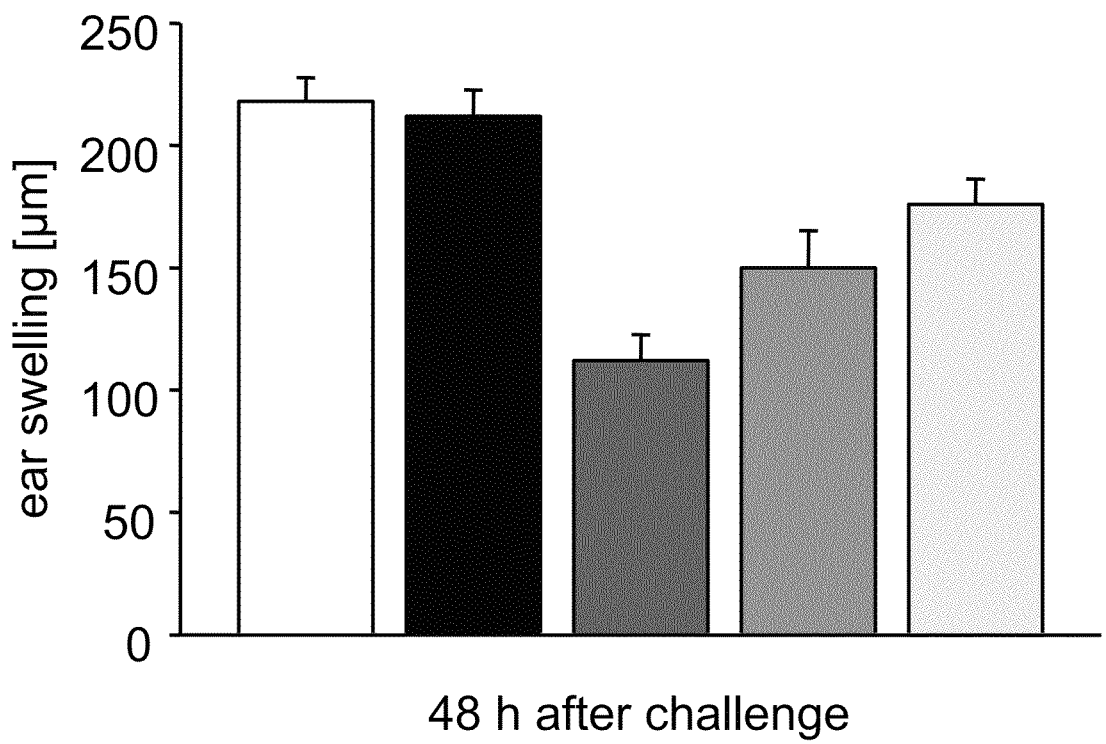

CD4+-T-cells Display Suppressive Properties after Treatment with KdPT-treated DC FIG. 33 shows that CD4+-T-cells after co-culture with α-MSH, KPV or KdPT become anergic and exert a suppressive effect on the proliferation of CD4+CD25-responder T-cells. Also in FIG. 33 it is shown that CD4+-T-cells ($1\times10^6$ cells), contacted in vitro with α-MSH, KPV or KdPT-treated DC, upon reinjection into sensitised recipient mice (Hapten: DNFB) show a suppressive effect on contact allergy.

EXAMPLE 21

Figure 34:
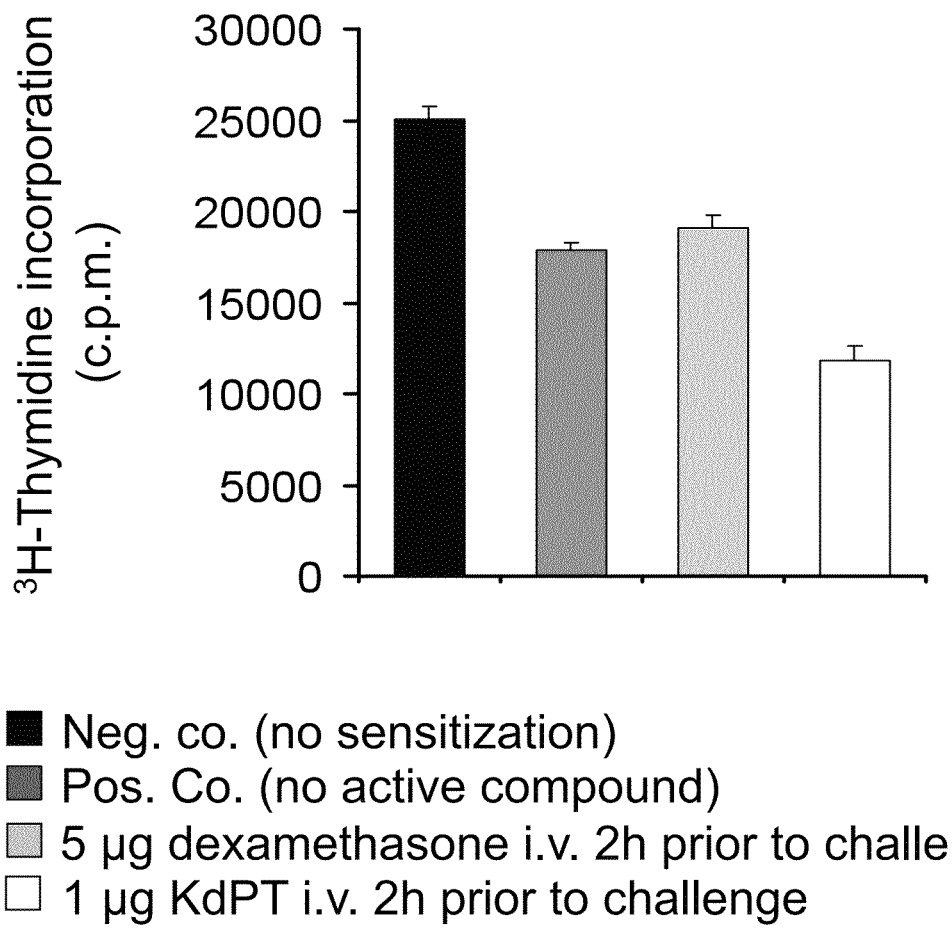
FIG. 34 shows the effect of KdPT on CD8+-T-cells from DNFB-sensitised mice/contact allergy experiment.
Figure 34:
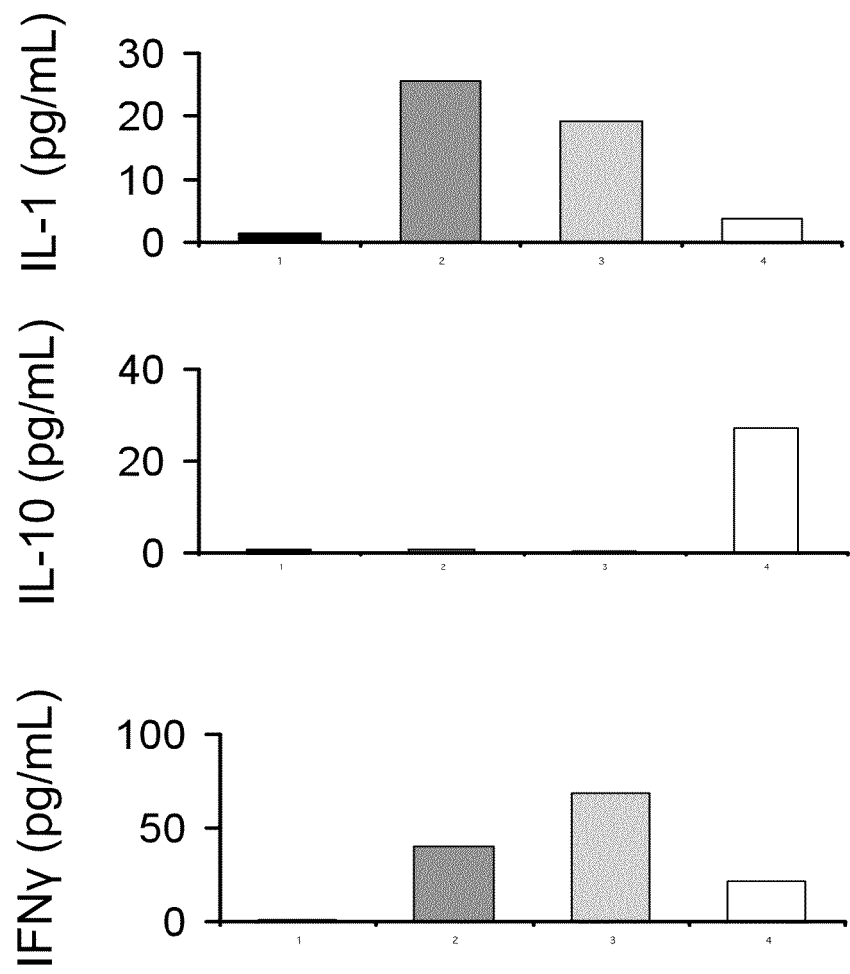
Figure 34:
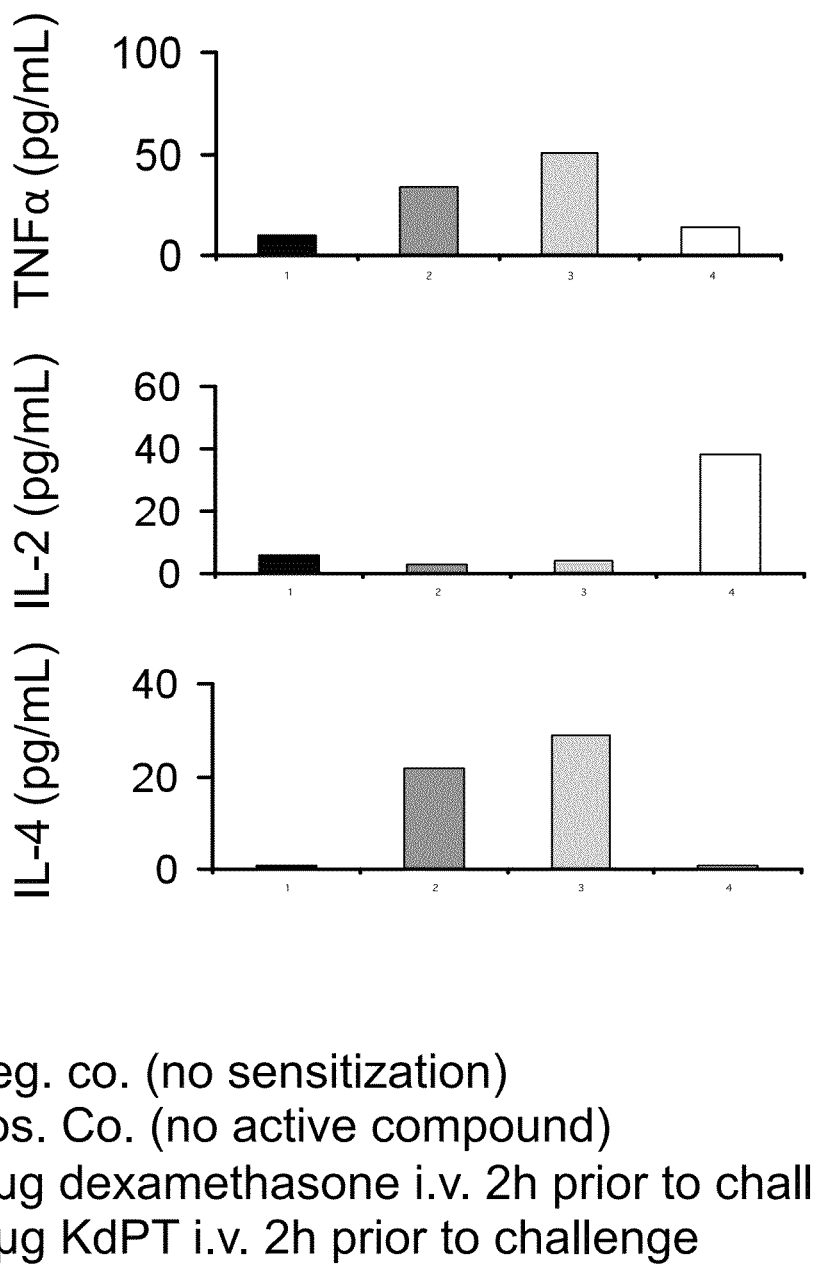

Effect of KdPT on CD8+-T-cells from DNFB-sensitised Mice/Contact Allergy Experiment In FIG. 34, C57BL/6 mice were sensitised with DNFB in vivo and treated either with KdPT or Dexamethasone. At the end of the experiments CD8+-T-cells were isolated and characterised. CD8+-T-cells from KdPT treated animals proliferated more slowly and secrete lower amounts of Th1-type cytokines, without a shift to the Th2-type, as can be deduced from the although suppressed secretion of IL-4. The clearly enhanced expression of IL-10 additionally indicates that the obtained T-cells mediate an altogether dampening effect in this allergic reaction.

EXAMPLE 22

Figure 35:
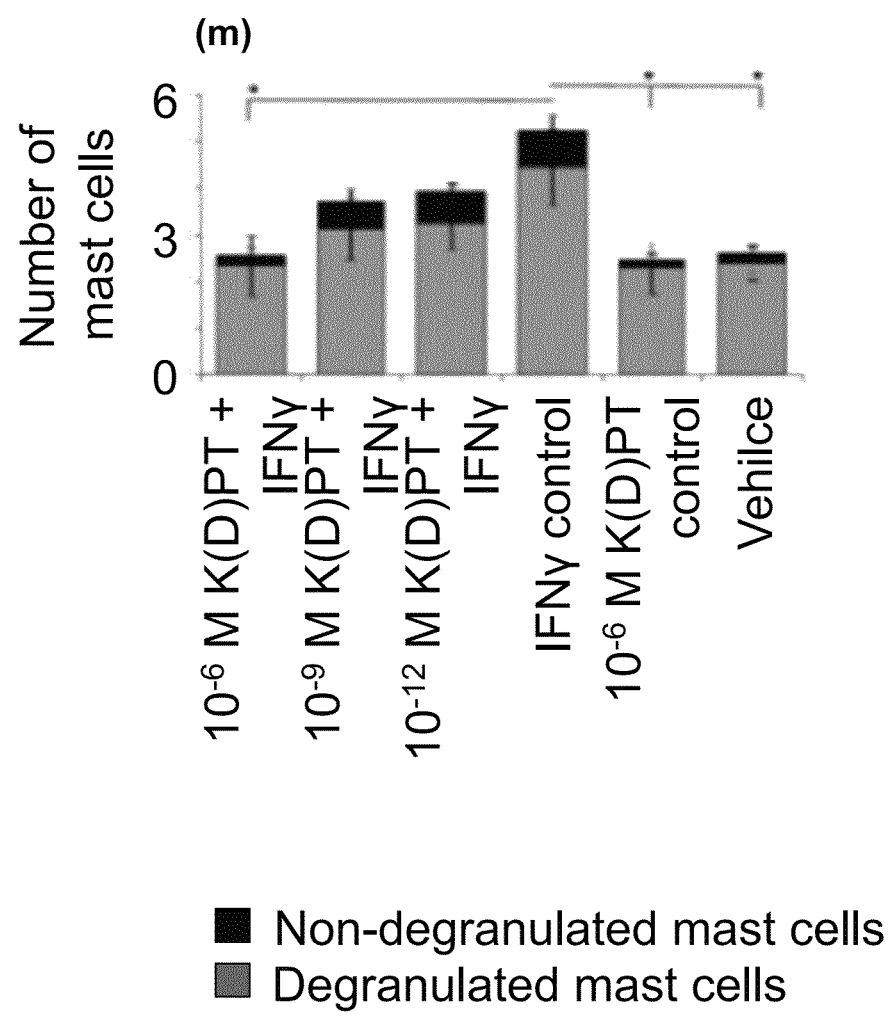
FIG. 35 shows the effect of KdPT on number and degranulation of human mast cells in the hair follicle.
Figure 35:
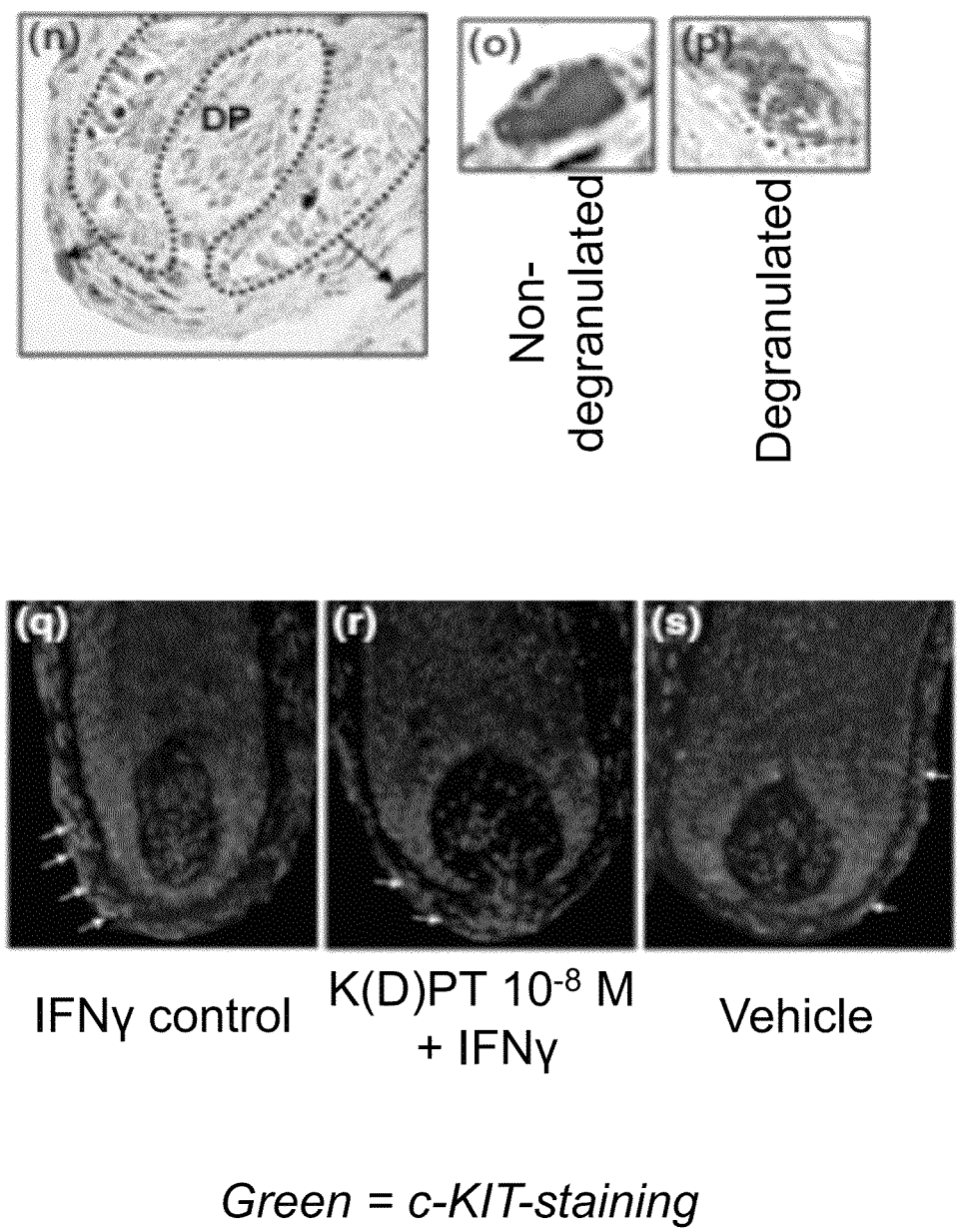

Effect of KdPT on Number and Degranulation of Human Mast Cells in the Hair Follicle In FIG. 35, (m) Each Leder esterase-stained hair follicle was quantitatively analyzed regarding its number of mast cells (nondegranulated/degranulated) and mena was calculated. Representative experiment of protection assay, n=10-18 hair follicles per group, data are mean±SEM *p<0.05. (n-p) Representative photodocument of a Leder esterase stained hair follicle (cytoplasmic mast cell granules stained red, green counterstain); (o) nondegranulated mast cell, (p) degranulated mast cell (original magnification ×400) (q-s) Representative photodocument of c-KIT staining (green signal/flourescein isothiocyanate) (original magnification ×200).

The results of these experiments clearly demonstrate the efficacy of KdPT in treating various autoimmune disorders.
(1) KdPT is Effective in at Least Two Model Systems for Different Autoimmune Disorders.

Administration of KdPT in the IL-10 deficient mice (FIG. 22) shows that weight loss and inflammation were significantly reduced in KdPT treated animals (FIG. 1). This is an animal model of Crohn's disease.

In two models for psoriasis comparable results could be obtained. In FIG. 23, a psoriasis-like condition was induced in mice by administration of Imiquimod/Aldara. FIGS. 24 and 25 show a transplant model of psoriasis. In both cases significant effects of KdPT on skin condition and molecular parameters are evident.
(2) KdPT Increases the Number of Regulatory CD4+CD25+ Foxp3+ T Cells.

In the Imiquimod model for psoriasis it was shown that the treatment of the animals with KdPT also results in significant increase in the number of regulatory CD4+CD25+Foxp3+ T cells, as well as in a significant upregulation of IL-10. At the same time, IFNγ and TNFα expression is suppressed (FIG. 26). These changes strongly suggest that there is an effect of KdPT on the number of regulatory T cells and on the expression of cytokines which are involved in many autoimmune disorders.

In case of humans a similar situation can be found. In PBMC from the blood of psoriasis patients administration of KdPT significantly increased the number of CD4+CD25+ Foxp3+ T cells (FIG. 27). These cells express less IL-10 and less IFNγ (FIG. 27). In addition, the regulatory T cells from the blood of these patients exhibit substantial suppressive properties after treatment with KdPT (FIG. 28).

The importance of regulatory T cells of this type, and in particular of Foxp3+ for human autoimmune disorders and the maintenance of self-tolerance has been discussed for several years in scientific journals (e.g. Sakaguchi et al. 2006 Immunol Rev 212:8-27; Valencia et al. 2007 Nat Clin Pract Rheum 3:619-626; Buckner J H 2010 Nat Rev 10:849-859). For various autoimmune disorders either reduced numbers of Treg cells or a reduced Treg activity is observed. Both things are obviously corrected by KdPT. The number of CD4+ CD25+Foxp3+ T cells is increased and due to the increase in IL-10 production an increase in activity can be assumed. In addition, KdPT-induced CD4+CD25+Foxp3+ T cells show a substantial suppressive phenotype.
(3) KdPT Reduces the Number of Th17 Cells.

Apart from the regulatory T cells, Th17 cells which have only recently been identified as a distinct cell population, have been discussed as playing a role in autoimmune disorders and also in allergic disorders in transplant rejection (e.g. Wang et al. 2011 Rheumatol Int January 11 epub; Tokura et al. 2010 J UOEH 32:317-328, Oh et al. 2011 Eur J Immunol 41:392-402, Shilling et al. 2011 Semin Immunpathol February 1 epub, Jadidi-Niaragh et al. 2011 Scand J Immunol doi: 10.1111/j.1365-3083.2011.02536.x. epub, Korn et al. 2009 Annu Rev Immunol 27:485-517, Lee et al. 2010 J Invest Dermatol 130:2540-2, Di Cesare et al. 2009 J Invest Dermatol 1339-50, Mesquita et al. Braz J Med Biol Res 42:476-486.).

With a view to Th17 cells it could be shown in samples from psoriasis patients that in the blood of these patients an increased number of Th17 cells could be reduced to the normal level of healthy individuals by KdPT (FIG. 29). Also on a molecular level this effect could be observed. Central cytokines such as IL-17 but also IL-21, IL-22 and IL-23 as well as transcription factor RORc were produced at reduced levels due to the influence of KdPT on CD4+ T cells (FIG. 29). Comparable data could be generated in the murine Imiquimod psoriasis model (FIG. 30).

The observed reduction on IL-17 expression alone suggests that KdPT, similar to the anti-IL-17 antibody AIN457 currently under development (Hueber et al. 2010 Science Translat Med 2(52):52-72) would have a broad effect in the treatment of autoimmune disorders. In addition it could be found that KdPT mediates its effect via a broader mechanism than only the isolated inhibition of IL-17 expression, as demonstrated by the attached data.

Of particular interest is also the relatedness of Th17 cells and regulatory T cells which allows an interplay between both cells types (Korn et al. 2009 Annu Rev Immunol 27:485-517 Mai et al. 2010 Front Biosci 15:986-1006). This can be derived also from the data shown here, see in particular direct comparison of FIG. 27 and FIG. 29 for the human case; as well as comparison of FIG. 26 and FIG. 30 for the murine model.
(4) KdPT Induces Tolerance.

In addition to the data on regulatory T cells and Th17 cells in animals and in the blood of psoriasis patients it should be mentioned that the effect of KdPT is mediated via an interaction with dendritic cells (DC) which represent the central type of antigen presenting cells. Treatment of DC with KdPT results in formation of a tolerating phenotype which elicits the above-described phenomena in interaction with T cells.

Dendritic cells generated in vitro by KdPT treatment express less co-stimulatory molecules (CD80, CD86), less molecules of the MHC II complex and more CD205 and IL-10 (FIG. 31).

CD4+ T cells which are contacted with these dendritic cells show a higher expression of regulatory molecules, such as Foxp3, Neuropilin-1(Nrp-1), IL-10 and CTLA-4 (FIG. 32) and act suppressive in proliferation assays (FIG. 32). Also in vivo these T cells are capable of acting suppressively (FIG. 33).

(5) Further Effects

With a view to allergic disorders it could be shown that KdPT has a direct effect on CD8+ T cells. CD8+ T cells which were isolated from in vivo sensitized and KdPT treated mice do proliferate less strongly than T cells from naïve mice, from only sensitized animals or sensitized and Dexamethason treated animals (FIG. 34).

Besides that, KdPT further appears to have an effect on mast cells, as shown on the basis of explanted hair follicles. In IFNγ stimulated hair follicles more and in particular more degranulated mast cells can be found than in hair follicles which have been stimulated with IFNγ and KdPT (Meyer et al. 2009 Br J Dermatol 161:1399-1424) (FIG. 35). These data represent a further link to the anti-allergic effect of KdPT already shown in the parent application.

In summary, ample experimental evidence strongly indicate that the peptides KP and KdPT are effective in the treatment of multiple autoimmune disorders and allergic reactions. This was shown by way of model systems for two specific autoimmune disorders. It is further supported by data regarding regulating T cells and Th17 cells. This supports the view that this effect can be observed in many inflammatory autoimmune disorders and allergic reaction.

The invention claimed is:

1. A method for treatment of Crohn's disease comprising the step of administering to a patient in need of such treatment, a pharmaceutical composition comprising a therapeutically effective amount of a compound selected from the group consisting of Lys-(D)Pro-Thr[K(D)PT] (KPT), N-acyl Lys-(D)Pro-Thr, C-amide Lys-(D)Pro-Thr, and C-esters of Lys-(D)Pro-Thr; or a pharmaceutically acceptable salt of said compound, wherein said therapeutically effective amount is in the range from 20 µg/kg of body weight to 10 mg/kg of body weight.

2. The method according to claim 1, wherein said pharmaceutical composition is in the form of an ointment or cream.

3. The method according to claim 2, wherein said compound is present in the ointment or cream in a concentration of 1 µM to 1 mM.

4. The method according to claim 1 wherein said pharmaceutical composition is formulated for intraperitoneal, intravenous or oral administration.

5. The method according to claim 1, wherein said pharmaceutical composition comprises at least two different compounds selected from the group consisting of Lys-(D)Pro-Thr [K(D)PT] (KPT), N-acyl Lys-(D)Pro-Thr, C-amide Lys-(D) Pro-Thr, and C-esters of Lys-(D)Pro-Thr.

6. The method of claim 1, wherein said therapeutically effective amount of the compound is 20 µg/kg of body weight to 10 mg/kg of body weight.

7. The method of claim 1, wherein said compound is the tripeptide Lys-(D) Pro-Thr.

8. The method of claim 1, wherein said compound is any one of N-acyl Lys-(D)Pro-Thr, C-amide Lys-(D)Pro-Thr, or C-esters of Lys-(D)Pro-Thr.

* * * * *